US011150242B2

(12) United States Patent
Ali et al.

(10) Patent No.: US 11,150,242 B2
(45) Date of Patent: Oct. 19, 2021

(54) IMMUNE CELL TRAPPING DEVICES AND METHODS FOR MAKING AND USING THE SAME

(71) Applicant: President and Fellows of Harvard College, Cambridge, MA (US)

(72) Inventors: Omar Abdel-Rahman Ali, Oakland, CA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 424 days.

(21) Appl. No.: 15/564,905

(22) PCT Filed: Apr. 8, 2016

(86) PCT No.: PCT/US2016/026617
§ 371 (c)(1),
(2) Date: Oct. 6, 2017

(87) PCT Pub. No.: WO2016/164705
PCT Pub. Date: Oct. 13, 2016

(65) Prior Publication Data
US 2018/0164298 A1 Jun. 14, 2018

Related U.S. Application Data

(60) Provisional application No. 62/146,205, filed on Apr. 10, 2015.

(51) Int. Cl.
*G01N 33/545* (2006.01)
*A61K 35/17* (2015.01)
(Continued)

(52) U.S. Cl.
CPC .......... *G01N 33/545* (2013.01); *A61K 35/15* (2013.01); *A61K 35/17* (2013.01); *A61L 31/06* (2013.01); *A61L 31/146* (2013.01); *A61L 31/16* (2013.01); *C08J 9/0004* (2013.01); *C08J 9/122* (2013.01); *C08J 9/26* (2013.01); *G01N 33/56972* (2013.01); *A61L 2300/438* (2013.01); *A61L 2300/62* (2013.01); *C08J 2201/032* (2013.01); *C08J 2201/0422* (2013.01); *C08J 2201/0446* (2013.01); *C08J 2203/06* (2013.01); *C08J 2203/08* (2013.01); *C08J 2205/044* (2013.01); *C08J 2205/05* (2013.01); *C08J 2207/10* (2013.01); *C08J 2305/00* (2013.01); *C08J 2305/04* (2013.01); *C08J 2305/08* (2013.01); *C08J 2305/12* (2013.01); *C08J 2325/04* (2013.01); *C08J 2329/04* (2013.01); *C08J 2333/04* (2013.01); *C08J 2339/00* (2013.01);
(Continued)

(58) Field of Classification Search
CPC ............. G01N 33/545; G01N 33/5743; G01N 2800/042; G01N 33/56972; A61K 35/15; A61K 35/17; A61L 2300/438; A61L 31/06; A61L 31/146; A61L 31/16; A61L 2300/62; C08J 2201/0422; C08J 2201/0446; C08J 2207/10; C08J 2367/04; C08J 9/0004; C08J 9/122; C08J 9/26; C08J 2339/06; C08J 2205/05; C08J 2329/04; C08J 2389/04; C08J 2201/032; C08J 2305/04; C08J 2205/044; C08J 2305/12; C08J 2367/00; C08J 2385/02; C08J 2325/04; C08J 2389/00; A61P 3/10; A61P 37/06; A61P 37/04; A61P 35/02; A61P 35/00; A61P 33/02; A61P 33/00; A61P 31/12; A61P 31/10; A61P 31/04; A61P 29/00; A61P 25/28; A61P 19/02; A61P 1/04
See application file for complete search history.

(56) References Cited

U.S. PATENT DOCUMENTS 3,773,919 A  11/1973  Boswell et al.
4,522,811 A   6/1985  Eppstein et al.
(Continued)

FOREIGN PATENT DOCUMENTS

AU  2018201930 A1  4/2018
CN      1757662 A   4/2006
(Continued)

OTHER PUBLICATIONS

John et al., J Immunol 2004; 172:5222-5229 (Year: 2004).*
(Continued)

*Primary Examiner* — Robert S Cabral
(74) *Attorney, Agent, or Firm* — McCarter & English, LLP; Maria Laccotripe Zacharakis; Maneesh Gulati, Esq.

(57) ABSTRACT

Embodiments herein described provide devices for identifying and collecting rare cells or cells which occur at low frequency in the body of a subject, such as, antigen-specific cells or disease-specific cells. More specifically, the devices are useful for trapping immune cells and the devices contain a physiologically-compatible porous polymer scaffold, a plurality of antigens, and an immune cell-recruiting agent, wherein the plurality of antigens and the immune cell recruiting agent attract and trap the immune cell in the device. Also provided are pharmaceutical compositions, kits, and packages containing such devices. Additional embodiments relate to methods for making the devices, compositions, and kits/packages. Further embodiments relate to methods for using the devices, compositions, and/or kits in the diagnosis or therapy of diseases such as autoimmune diseases or cancers.

27 Claims, 11 Drawing Sheets

(51) Int. Cl.

| | | |
|---|---|---|
| C08J 9/00 | (2006.01) | |
| C08J 9/12 | (2006.01) | |
| C08J 9/26 | (2006.01) | |
| A61L 31/14 | (2006.01) | |
| A61L 31/16 | (2006.01) | |
| A61K 35/15 | (2015.01) | |
| A61L 31/06 | (2006.01) | |
| G01N 33/569 | (2006.01) | |
| G01N 33/574 | (2006.01) | |

(52) U.S. Cl.
CPC ........ *C08J 2339/06* (2013.01); *C08J 2367/00* (2013.01); *C08J 2367/04* (2013.01); *C08J 2371/02* (2013.01); *C08J 2385/02* (2013.01); *C08J 2389/00* (2013.01); *C08J 2389/04* (2013.01); *G01N 33/5743* (2013.01); *G01N 2800/042* (2013.01); *Y02A 50/30* (2018.01)

(56) References Cited

U.S. PATENT DOCUMENTS

| | | | |
|---|---|---|---|
| 4,946,778 | A | 8/1990 | Ladner et al. |
| 5,091,513 | A | 2/1992 | Huston et al. |
| 5,132,405 | A | 7/1992 | Huston et al. |
| 5,885,829 | A | 3/1999 | Mooney et al. |
| 5,888,987 | A | 3/1999 | Haynes et al. |
| 5,906,826 | A | 5/1999 | Emery et al. |
| 5,951,976 | A | 9/1999 | Segal |
| 6,129,716 | A | 10/2000 | Steer |
| 6,160,084 | A | 12/2000 | Langer et al. |
| 6,193,970 | B1 | 2/2001 | Pardoll et al. |
| 6,251,396 | B1 | 6/2001 | Gaur et al. |
| 6,281,256 | B1 | 8/2001 | Harris et al. |
| 6,334,968 | B1 | 1/2002 | Shapiro et al. |
| 6,352,694 | B1 | 3/2002 | June et al. |
| 6,403,374 | B1 | 6/2002 | Tsien et al. |
| 6,429,199 | B1 | 8/2002 | Krieg et al. |
| 6,511,511 | B1 | 1/2003 | Slivka et al. |
| 6,511,650 | B1 | 1/2003 | Eiselt et al. |
| 6,541,022 | B1 | 4/2003 | Murphy et al. |
| 6,642,363 | B1 | 11/2003 | Mooney et al. |
| 6,685,963 | B1 | 2/2004 | Taupin et al. |
| 6,748,954 | B2 | 6/2004 | Lee et al. |
| 6,767,928 | B1 | 7/2004 | Murphy et al. |
| 6,783,712 | B2 | 8/2004 | Slivka et al. |
| 6,790,840 | B1 | 9/2004 | Lee et al. |
| 6,797,738 | B2 | 9/2004 | Harris et al. |
| 6,800,733 | B2 | 10/2004 | Tsien et al. |
| 6,858,222 | B2 | 2/2005 | Nelson et al. |
| 6,974,698 | B1 | 12/2005 | Miller et al. |
| 7,015,205 | B1 | 3/2006 | Wallack et al. |
| 7,157,566 | B2 | 1/2007 | Tsien et al. |
| 7,186,413 | B2 | 3/2007 | Bouhadir et al. |
| 7,192,693 | B2 | 3/2007 | Bryant et al. |
| 7,244,714 | B1 | 7/2007 | Gonda et al. |
| 7,410,953 | B2 | 8/2008 | Kawasaki |
| 7,427,602 | B1 | 9/2008 | Shea et al. |
| 7,569,850 | B2 | 8/2009 | Noy et al. |
| 7,575,759 | B2 | 8/2009 | Murphy et al. |
| 7,687,241 | B2 | 3/2010 | Chen |
| 7,709,458 | B2 | 5/2010 | Karaolis et al. |
| 7,790,699 | B2 | 9/2010 | Melvik et al. |
| 8,067,237 | B2 | 11/2011 | Mooney et al. |
| 8,188,058 | B2 | 5/2012 | Hackam et al. |
| 8,273,373 | B2 | 9/2012 | Alsberg et al. |
| 8,354,119 | B2 | 1/2013 | Geistlich et al. |
| 8,367,628 | B2 | 2/2013 | Goodwin et al. |
| 8,535,719 | B2 | 9/2013 | Badylak et al. |
| 8,709,464 | B2 | 4/2014 | Ma et al. |
| 8,728,456 | B2 | 5/2014 | Sands et al. |
| 8,883,308 | B2 | 11/2014 | Polshettiwar et al. |
| 8,932,583 | B2 | 1/2015 | Mooney et al. |
| 9,012,399 | B2 | 4/2015 | Cao et al. |
| 9,132,210 | B2 | 9/2015 | Mooney et al. |
| 9,139,809 | B2 | 9/2015 | Porcelli et al. |
| 9,150,631 | B2 | 10/2015 | Super et al. |
| 9,370,558 | B2 | 6/2016 | Ali et al. |
| 9,381,235 | B2 | 7/2016 | Sands et al. |
| 9,446,107 | B2 | 9/2016 | Mooney et al. |
| 9,486,512 | B2 | 11/2016 | Kim et al. |
| 9,591,360 | B2 | 3/2017 | Jennings et al. |
| 9,675,561 | B2 | 6/2017 | Bencherif et al. |
| 9,770,535 | B2 * | 9/2017 | Mooney ............ A61L 27/50 |
| 9,821,045 | B2 | 11/2017 | Ali et al. |
| 9,937,249 | B2 | 4/2018 | Kim et al. |
| 10,045,947 | B2 | 8/2018 | Bencherif et al. |
| 10,080,789 | B2 | 9/2018 | Sands et al. |
| 10,137,184 | B2 | 11/2018 | Mooney et al. |
| 10,149,897 | B2 | 12/2018 | Mooney et al. |
| 10,258,677 | B2 | 4/2019 | Mooney et al. |
| 10,328,133 | B2 | 6/2019 | Mooney et al. |
| 2002/0045672 | A1 | 4/2002 | Harris et al. |
| 2002/0131853 | A1 | 9/2002 | Nagasawa |
| 2002/0131953 | A1 | 9/2002 | Takashima et al. |
| 2002/0150604 | A1 | 10/2002 | Yi et al. |
| 2003/0075822 | A1 | 4/2003 | Slivka et al. |
| 2003/0082806 | A1 | 5/2003 | Berenson et al. |
| 2003/0095994 | A1 | 5/2003 | Geistlich et al. |
| 2003/0100527 | A1 | 5/2003 | Krieg et al. |
| 2003/0194397 | A1 | 10/2003 | Mishra |
| 2003/0232895 | A1 | 12/2003 | Omidian et al. |
| 2004/0028745 | A1 | 2/2004 | Bouhadir et al. |
| 2004/0043034 | A1 | 3/2004 | Jensenius et al. |
| 2004/0058883 | A1 | 3/2004 | Phillips et al. |
| 2004/0063206 | A1 | 4/2004 | Rowley et al. |
| 2004/0136968 | A1 | 7/2004 | Zheng et al. |
| 2004/0151764 | A1 | 8/2004 | Zamora |
| 2004/0213795 | A1 | 10/2004 | Collins et al. |
| 2004/0220111 | A1 | 11/2004 | Kleinman et al. |
| 2004/0228858 | A1 | 11/2004 | Hanson et al. |
| 2004/0242469 | A1 | 12/2004 | Lee et al. |
| 2004/0242482 | A1 | 12/2004 | Gehring et al. |
| 2005/0002915 | A1 | 1/2005 | Atala et al. |
| 2005/0037330 | A1 | 2/2005 | Fischer et al. |
| 2005/0053667 | A1 | 3/2005 | Irvine et al. |
| 2005/0079159 | A1 | 4/2005 | Shastri et al. |
| 2005/0090008 | A1 | 4/2005 | Segura et al. |
| 2005/0106211 | A1 | 5/2005 | Nelson et al. |
| 2005/0154376 | A1 | 7/2005 | Riviere et al. |
| 2005/0177249 | A1 | 8/2005 | Kladakis et al. |
| 2005/0202394 | A1 | 9/2005 | Dobson |
| 2006/0083712 | A1 | 4/2006 | Anversa |
| 2006/0141018 | A1 | 6/2006 | Cochrum et al. |
| 2006/0264380 | A1 | 11/2006 | Hellstrom et al. |
| 2006/0292134 | A1 | 12/2006 | Stohs |
| 2007/0003595 | A1 | 1/2007 | Wang et al. |
| 2007/0020232 | A1 | 1/2007 | Rossignol et al. |
| 2007/0026518 | A1 | 2/2007 | Healy et al. |
| 2007/0081972 | A1 | 4/2007 | Sandler et al. |
| 2007/0116680 | A1 | 5/2007 | Stegemann et al. |
| 2007/0178159 | A1 | 8/2007 | Chen et al. |
| 2007/0190646 | A1 | 8/2007 | Engler et al. |
| 2008/0044900 | A1 | 2/2008 | Mooney et al. |
| 2008/0044990 | A1 | 2/2008 | Lee |
| 2008/0051490 | A1 | 2/2008 | Williams et al. |
| 2008/0113929 | A1 | 5/2008 | Lipford et al. |
| 2008/0138416 | A1 | 6/2008 | Rauh et al. |
| 2008/0152624 | A1 | 6/2008 | Paludan et al. |
| 2008/0206308 | A1 | 8/2008 | Jabbari et al. |
| 2008/0233181 | A1 | 9/2008 | Nagy et al. |
| 2008/0268019 | A1 | 10/2008 | Badylak et al. |
| 2008/0268052 | A1 | 10/2008 | Voytik-Harbin et al. |
| 2009/0017096 | A1 | 1/2009 | Lowman et al. |
| 2009/0192079 | A1 | 7/2009 | Santos et al. |
| 2009/0238853 | A1 | 9/2009 | Liu et al. |
| 2009/0252752 | A1 | 10/2009 | Tahara et al. |
| 2009/0297579 | A1 | 12/2009 | Semino et al. |
| 2009/0305983 | A1 | 12/2009 | Ying et al. |
| 2010/0015709 | A1 | 1/2010 | Rehfeldt et al. |
| 2010/0055102 | A1 | 3/2010 | Langermann |
| 2010/0055186 | A1 | 3/2010 | Dadsetan et al. |
| 2010/0080816 | A1 | 4/2010 | Hadeiba et al. |
| 2010/0129422 | A1 | 5/2010 | Han et al. |

(56) References Cited

U.S. PATENT DOCUMENTS

| | | |
|---|---|---|
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0008443 A1 | 1/2011 | Alsberg et al. |
| 2011/0020216 A1* | 1/2011 | Mooney ............ A61L 27/50 424/1.11 |
| 2011/0117170 A1 | 5/2011 | Cao et al. |
| 2011/0207166 A1 | 8/2011 | Vaiselbuh |
| 2011/0223255 A1 | 9/2011 | Thiesen et al. |
| 2011/0253643 A1 | 10/2011 | Polshettiwar et al. |
| 2011/0256184 A1 | 10/2011 | Lei et al. |
| 2011/0300186 A1 | 12/2011 | Hellstrom et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0294888 A1 | 11/2012 | Kishimoto et al. |
| 2012/0329791 A1 | 12/2012 | Ashwell et al. |
| 2013/0029030 A1 | 1/2013 | Larsen |
| 2013/0035283 A1 | 2/2013 | Super et al. |
| 2013/0045246 A1 | 2/2013 | Edwards et al. |
| 2013/0052117 A1 | 2/2013 | Imai et al. |
| 2013/0072547 A1 | 3/2013 | Hackam et al. |
| 2013/0145488 A1 | 6/2013 | Wang et al. |
| 2013/0177536 A1 | 7/2013 | Mooney et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0072510 A1 | 3/2014 | Shea et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0227723 A1 | 8/2014 | Ingber et al. |
| 2014/0234423 A1 | 8/2014 | Sands et al. |
| 2015/0024026 A1 | 1/2015 | Mooney et al. |
| 2015/0030669 A1 | 1/2015 | Platscher et al. |
| 2015/0072009 A1 | 3/2015 | Kim et al. |
| 2015/0359928 A1 | 12/2015 | Gu et al. |
| 2015/0366956 A1 | 12/2015 | Mooney et al. |
| 2016/0033511 A1 | 2/2016 | Pannell et al. |
| 2016/0220668 A1 | 8/2016 | Mooney et al. |
| 2016/0228543 A1 | 8/2016 | Mooney et al. |
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0042995 A1 | 2/2017 | Ali et al. |
| 2017/0182138 A1 | 6/2017 | Kim et al. |
| 2017/0246281 A1 | 8/2017 | Super et al. |
| 2017/0362307 A1 | 12/2017 | Ingber et al. |
| 2018/0021253 A1 | 1/2018 | Sandeep et al. |
| 2018/0117171 A1 | 5/2018 | Mooney et al. |
| 2018/0243231 A1 | 8/2018 | Bencherif et al. |
| 2018/0289789 A1 | 10/2018 | Ali et al. |
| 2018/0320157 A1 | 11/2018 | Super et al. |
| 2018/0344821 A1 | 12/2018 | Kim et al. |
| 2018/0371058 A1 | 12/2018 | Waiters et al. |
| 2019/0060525 A1 | 2/2019 | Shah et al. |
| 2019/0076373 A1 | 3/2019 | Bencherif et al. |
| 2019/0125849 A1 | 5/2019 | Mooney et al. |
| 2019/0183992 A1 | 6/2019 | Sands et al. |
| 2019/0216910 A1 | 7/2019 | Mooney et al. |
| 2019/0292517 A1* | 9/2019 | Cheung ............ A61K 38/1841 |

FOREIGN PATENT DOCUMENTS

| | | |
|---|---|---|
| CN | 101655611 A | 2/2010 |
| EP | 0562862 A1 | 9/1993 |
| EP | 1452191 A2 | 9/2004 |
| EP | 1561481 A2 | 8/2005 |
| EP | 1712238 A1 | 10/2006 |
| EP | 1975230 A1 | 10/2008 |
| JP | 2000-503884 A | 4/2000 |
| JP | 2001-524136 A | 11/2001 |
| JP | 2003-506401 A | 2/2003 |
| JP | 2003-180815 A | 7/2003 |
| JP | 2004-159849 A | 6/2004 |
| JP | 2004-520043 A | 7/2004 |
| JP | 2005-160669 A | 6/2005 |
| JP | 2005-170816 A | 6/2005 |
| JP | 2005-528401 A | 9/2005 |
| JP | 2007-500673 A | 1/2007 |
| JP | 2007-503881 A | 3/2007 |
| JP | 2007-505827 A | 3/2007 |
| JP | 2007-528848 A | 10/2007 |
| JP | 2008-515503 A | 5/2008 |
| JP | 2008-528114 A | 7/2008 |
| JP | 2009-519042 A | 5/2009 |
| JP | 2009-521406 A | 6/2009 |
| JP | 2009-540921 A | 11/2009 |
| JP | 2010-502824 A | 1/2010 |
| JP | 2010-508976 A | 3/2010 |
| JP | 2010-227012 A | 10/2010 |
| JP | 2011-511684 A | 4/2011 |
| JP | 2011-511834 A | 4/2011 |
| JP | 2013-531043 A | 8/2013 |
| WO | WO-1996/02555 A1 | 2/1996 |
| WO | WO-1996/16086 A1 | 5/1996 |
| WO | WO-1998/12228 A1 | 3/1998 |
| WO | WO-1998/16266 A1 | 4/1998 |
| WO | WO-1999/44583 A2 | 9/1999 |
| WO | WO-1999/51259 A2 | 10/1999 |
| WO | WO-2000/50006 A2 | 8/2000 |
| WO | WO-2001/10421 A1 | 2/2001 |
| WO | WO-2001/35932 A2 | 5/2001 |
| WO | WO-2001/37810 A2 | 5/2001 |
| WO | WO-2002/16557 A2 | 2/2002 |
| WO | WO-2002/40071 A1 | 5/2002 |
| WO | WO-2002/058723 A2 | 8/2002 |
| WO | WO-2002/092054 A2 | 11/2002 |
| WO | WO-2003/020161 A2 | 3/2003 |
| WO | WO-2003/020884 A2 | 3/2003 |
| WO | WO-2003/088905 A2 | 10/2003 |
| WO | WO-2004/006990 A2 | 1/2004 |
| WO | WO-2004/029230 A2 | 4/2004 |
| WO | WO-2004/030706 A2 | 4/2004 |
| WO | WO-2004/031371 A2 | 4/2004 |
| WO | WO-2004/089413 A1 | 10/2004 |
| WO | WO-2005/013896 A2 | 2/2005 |
| WO | WO-2005/013933 A1 | 2/2005 |
| WO | WO-2005/020849 A2 | 3/2005 |
| WO | WO-2005/025614 A2 | 3/2005 |
| WO | WO-2005/026318 A2 | 3/2005 |
| WO | WO-2005/037190 A2 | 4/2005 |
| WO | WO-2005/037293 A1 | 4/2005 |
| WO | WO-2005/046748 A1 | 5/2005 |
| WO | WO-2005/072088 A2 | 8/2005 |
| WO | WO-2005/104755 A2 | 11/2005 |
| WO | WO-2006/039045 A2 | 4/2006 |
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | 2007/001332 A2 | 1/2007 |
| WO | WO-2007/030901 A1 | 3/2007 |
| WO | WO-2007/039150 A2 | 4/2007 |
| WO | WO-2007/042554 A2 | 4/2007 |
| WO | 2007/051120 A2 | 5/2007 |
| WO | 2007/068489 A2 | 6/2007 |
| WO | WO-2007/063075 A1 | 6/2007 |
| WO | WO-2007/064152 A1 | 6/2007 |
| WO | WO-2007/070660 A2 | 6/2007 |
| WO | WO-2007/078196 A1 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |

(56) References Cited

FOREIGN PATENT DOCUMENTS

| | | |
|---|---|---|
| WO | WO-2007/150020 A1 | 12/2007 |
| WO | WO-2008/008266 A2 | 1/2008 |
| WO | WO-2008/018707 A1 | 2/2008 |
| WO | WO-2008/031525 A1 | 3/2008 |
| WO | WO-2008/043157 A1 | 4/2008 |
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A1 | 12/2008 |
| WO | WO-2008/157394 A2 | 12/2008 |
| WO | WO-2009/002401 A2 | 12/2008 |
| WO | WO-2009/005769 A2 | 1/2009 |
| WO | 2009/024775 A1 | 2/2009 |
| WO | WO-2009/018500 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009/102465 A2 | 8/2009 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | WO-2011/043834 A1 | 4/2011 |
| WO | WO-2011/043835 A1 | 4/2011 |
| WO | WO-2011/063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A2 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | WO-2013/012924 A2 | 1/2013 |
| WO | WO-2013/106852 A1 | 7/2013 |
| WO | WO-2013/158673 A1 | 10/2013 |
| WO | 2013/172967 A1 | 11/2013 |
| WO | WO-2013/190555 A1 | 12/2013 |
| WO | WO-2014/063128 A1 | 4/2014 |
| WO | 2014/190229 A1 | 11/2014 |
| WO | WO-2014/189805 A1 | 11/2014 |
| WO | WO-2015/066535 A1 | 5/2015 |
| WO | WO-2015/154078 A1 | 10/2015 |
| WO | WO-2015/168379 A2 | 11/2015 |
| WO | 2016/004068 A1 | 1/2016 |
| WO | WO-2016/123573 A1 | 8/2016 |
| WO | WO-2016/161372 A1 | 10/2016 |
| WO | WO-2017/143024 A2 | 8/2017 |
| WO | WO-2018/013797 A1 | 1/2018 |
| WO | WO-2018/026884 A1 | 2/2018 |

OTHER PUBLICATIONS

Furdui et al., Lab Chip, 2004, 4, 614-618 (Year: 2004).*
Abrahams et al., Expression and secretion of antiviral factors by trophoblast cells following stimulation by the TLR-3 agonist, Poly(I:C). Hum Reprod. Sep. 2006;21(9):2432-9.
Agache et al., Mechanical properties and Young's modulus of human skin in vivo. Arch Dermatol Res. 1980;269(3):221-32.
Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.
Aguado et al., Improving viability of stem cells during syringe needle flow through the design of hydrogel cell carriers. Tissue Eng Part A. Apr. 2012;18(7-8):806-15.
Akira et al., Pathogen recognition and innate immunity. Cell. Feb. 24, 2006;124(4):783-801.
Akira et al., Toll-like receptors: critical proteins linking innate and acquired immunity. Nat Immunol. Aug. 2001;2(8):675-80.
Akpalo et al., Fibrin-polyethylene oxide interpenetrating polymer networks: new self-supported biomaterials combining the properties of both protein gel and synthetic polymer. Acta Biomater. Jun. 2011;7(6):2418-27.
Aldhous, Print Me a Heart and a Set of Arteries. New Scientist. 2006;2547:19.
Ali et al., Biomaterial-based vaccine induces regression of established intracranial glioma in rats. Pharm Res. May 2011;28(5):1074-80.
Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.
Ali et al., Converging Cell Therapy with Biomaterials. Cell Transplantation from Laboratory to Clinic. 2006:591-609.
Ali et al., Identification of immune factors regulating antitumor immunity using polymeric vaccines with multiple adjuvants. Cancer Res. Mar. 15, 2014;74(6):1670-81.
Ali et al., In situ regulation of DC subsets and T cells mediates tumor regression in mice. Sci Transl Med. Nov. 25, 2009;1(8):8ra19, 1-10.
Ali et al., Infection-mimicking materials to program dendritic cells in situ. Nat Mater. Feb. 2009;8(2):151-8.
Ali et al., Inflammatory cytokines presented from polymer matrices differentially generate and activate DCs in situ.. Adv Funct Mater. Aug. 1, 2013;23(36):4621-4628.
Ali et al., Relationship of vaccine efficacy to the kinetics of DC and T-cell responses induced by PLG-based cancer vaccines. Biomater. 2011;1(1):66-75.
Ali et al., Sustained GM-CSF and PEI condensed pDNA presentation increases the level and duration of gene expression in dendritic cells. J Control Release. Dec. 18, 2008;132(3):273-8.
Ali et al., The efficacy of intracranial PLG-based vaccines is dependent on direct implantation into brain tissue. J Control Release. Sep. 25, 2011;154(3):249-57.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineering growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
Anderson et al., Biomaterial microarrays: rapid. microscale screening of polymer-cell interaction. Biomaterials. Aug. 2005;26(23):4892-7.
Anderson et al., Nanoliter-scale synthesis of arrayed biomaterials and application to human embryonic stem cells. Nat Biotechnol. Jul. 2004;22(7):863-6.
Anderson, A role for nitric oxide in muscle repair: nitric oxide-mediated activation of muscle satellite cells. Mol Biol Cell. May 2000;11(5):1859-74.
Annabi et al., Controlling the porosity and microarchitecture of hydrogels for tissue engineering. Tissue Eng Part B Rev. Aug. 2010;16(4):371-83.
Annual Review. 2008:122-131.
Arany et al., At the edge of translation-materials to program cells for directed differentiation. Oral Dis. Apr. 2011;17(3):241-51.
Aschner et al., Metabolic memory for vascular disease in diabetes. Diabetes Technol Ther. Jun. 2012;14 Suppl 1:S68-74.
Atala et al., Endoscopic treatment of vesicoureteral reflux with a chondrocyte-alginate suspension. J Urol. Aug. 1994;152(2 Pt 2):641-3.

(56) References Cited

OTHER PUBLICATIONS

Aubin et al., Directed 3D cell alignment and elongation in microengineered hydrogels. Biomaterials. Sep. 2010;31(27):6941-6951.
Augst et al., Alginate hydrogels as biomaterials. Macromol Biosci. Aug. 7, 2006;6(8):623-33.
Babensee et al., Host response to tissue engineered devices. Advanced Drug Delivery Reviews. Aug. 3, 1998;33(1-2):111-139.
Bachelder et al., Acid-degradable polyurethane particles for protein-based vaccines: biological evaluation and in vitro analysis of particle degradation products. Mol Pharm. Sep.-Oct. 2008;5(5):876-84.
Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007;114(5):855-9.
Balakrishna et al., Structural correlates of antibacterial and membrane-permeabilizing activities in acylpolyamines. Antimicrob Agents Chemother. Mar. 2006;50(3):852-61.
Banchereau et al., Dendritic cells and the control of immunity. Nature. Mar. 19, 1998;392(6673):245-52.
Bar-Cohen et al., Electroactive Polymer Actuators and Sensors. MRS Bullet. 2008;33(3):173-181.
Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.
Barbero et al., Growth factor supplemented matrigel improves ectopic skeletal muscle formation—a cell therapy approach. J Cell Physiol. Feb. 2001;186(2):183-92.
Barbucci et al., Hyaluronic acid hydrogel in the treatment of osteoarthritis. Biomaterials. Dec. 2002;23(23):4503-13.
Barrio et al., A two-dimensional numerical study of spatial pattern formation in interacting Turing systems. Bull Math Biol. May 1999;61(3):483-505.
Baskin et al., Copper-free click chemistry for dynamic in vivo imaging. Proc Natl Acad Sci U S A. Oct. 23, 2007;104(43):16793-7.
Bates, Improved muscle regeneration by combining VEGF with IGF1. Regen Med. Nov. 2010;5(6):853-4.
Beaucage et al., The Functionalization of Oligonucleotides via Phosphoramidite Derivatives. Tetrahedron. Mar. 5, 1993;49(10):1925-1963.
Beauchamp et al., Dynamics of myoblast transplantation reveal a discrete minority of precursors with stem cell-like properties as the myogenic source. J Cell Biol. Mar. 22, 1999;144(6):1113-22.
Becker et al., Cytological demonstration of the clonal nature of spleen colonies derived from transplanted mouse marrow cells. Nature. Feb. 2, 1963;197:452-4.
Beebe et al., Functional hydrogel structures for autonomous flow control inside microfluidic channels. Nature. Apr. 6, 2000;404(6778):588-90.
Bekiari et al., Study of poly(N,N-dimethylacrylamide)/CdS nanocomposite organic/inorganic gels. Langmuir. Sep. 14, 2004;20(19):7972-5.
Bell, Models for the specific adhesion of cells to cells. Science. May 12, 1978;200(4342):618-27.
Bencherif et al., End-group effects on the properties of PEG-co-PGA hydrogels. Acta Biomater. Jul. 2009;5(6):1872-83.
Bencherif et al., Influence of cross-linker chemistry on release kinetics of PEG-co-PGA hydrogels. J Biomed Mater Res A. Jul. 2009;90(1):142-53.
Bencherif et al., Influence of the degree of methacrylation on hyaluronic acid hydrogels properties. Biomaterials. Apr. 2008;29(12):1739-49.
Bencherif et al., Injectable preformed scaffolds with shape-memory properties. Proc Natl Acad Sci U S A. Nov. 27, 2012;109(48):19590-5.
Bencherif et al., Nanostructured hybrid hydrogels prepared by a combination of atom transfer radical polymerization and free radical polymerization. Biomaterials. Oct. 2009;30(29):5270-8.
Bencherif et al., Synthesis by AGET ATRP of degradable nanogel precursors for in situ formation of nanostructured hyaluronic acid hydrogel. Biomacromolecules. Sep. 14, 2009;10(9):2499-507.
Benton et al., Photocrosslinking of gelatin macromers to synthesize porous hydrogels that promote valvular interstitial cell function. Tissue Eng Part A. Nov. 2009;15(11):3221-30.
Berg et al., Il-10 is a central regulator of cyclooxygenase-2 expression and prostaglandin production. J Immunol. Feb. 15, 2001;166(4):2674-80.
Bergstraesser et al., Stimulation and inhibition of human mammary epithelial cell duct morphogenesis in vitro. Proc Assoc Am Physicians. Mar. 1996;108(2):140-54.
Bianco et al., The meaning, the sense and the significance: translating the science of mesenchymal stem cells into medicine. Nat Med. Jan. 2013;19(1):35-42.
Bilodeau et al., Regular Pyramid Punch Problem. J Appl Mech. 1992;59(3):519-523.
Bischoff, Proliferation of muscle satellite cells on intact myofibers in culture. Dev Biol. May 1986;115(1):129-39.
Bjork et al., Tuning the shape of mesoporous silica particles by alterations in parameter space: from rods to platelets. Langmuir. Nov. 5, 2013;29(44):13551-61.
Blumenthal et al., Polyurethane scaffolds seeded with genetically engineered skeletal myoblasts: a promising tool to regenerate myocardial function. Artif Organs. Feb. 2010;34(2):E46-54.
Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci U S A. Sep. 13, 2011;108(37):E674-80.
Bohl et al., Role of synthetic extracellular matrix in development of engineered dental pulp. J Biomater Sci Polym Ed. 1998;9(7):749-64.
Bojarova et al., Sugared biomaterial binding lectins: achievements and perspectives. Biomater Sci. Jul. 19, 2016;4(8):1142-60.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomaterials. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnol Prog. Sep.-Oct. 2001;17(5):945-50.
Bouhadir et al., Synthesis of Cross-Linked Poly(aldehyde guluronate) Hydrogels. Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromolecules. Jul.-Aug. 2003;4(4):890-5.
Brinkmann et al., Neutrophil extracellular traps kill bacteria. Science. Mar. 5, 2004;303(5663):1532-5.
Bristol-Myers Squibb, Investigational Anti-PD-1 Immunotherapy BMS-936558 Showed Clinical Activity in Phase 1 Trial of Patients

(56) References Cited

OTHER PUBLICATIONS with Previously-Treated non-Small-Cell Lung Cancer, Metastatic Melanoma adn Renal Cell Cancer. Financial Times. 3 pages, Jun. 2, 2012.
Brouwers et al., Can the growth factors PTHrP, Ihh and VEGF, together regulate the development of a long bone? J Biomech. 2006;39(15):2774-82.
Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.
Bryant et al., Photo-patterning of porous hydrogels for tissue engineering. Biomaterials. Jul. 2007;28(19):2978-86.
Buckwalter et al., Form of Antigen Dictates Immunity: Irradiated Cell vs. Whole Cell Lysate Vaccination. J Immunol. Apr. 1, 2007;178(1 Suppl):S77.
Bullard et al., Fetal wound healing: current biology. World J Surg. Jan. 2003;27(1):54-61.
Buonaguro et al., Translating tumor antigens into cancer vaccines. Clin Vaccine Immunol. Jan. 2011;18(1):23-34.
Burdick et al., Controlled degradation and mechanical behavior of photopolymerized hyaluronic acid networks. Biomacromolecules. Jan.-Feb. 2005;6(1):386-91.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9.
Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.
Bégué et al., Vaccination against human papillomavirus. Implementation and efficacy against cervical cancer control. Bull Acad Natl Med. Dec. 2007;191(9):1805-16.
Callahan et al., At the bedside: CTLA-4- and PD-1-blocking antibodies in cancer immunotherapy. J Leukoc Biol. Jul. 2013;94(1):41-53.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009;30(25):4085-93.
care.diabetesjournals.org, Standards of Medical Care in Diabetes. Diabetes Care. Jan. 2013;36(Suppl 1):S1-S2.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6):133-8.

Champion et al., Shape induced inhibition of phagocytosis of polymer particles. Pharm Res. Jan. 2009;26(1):244-9.
Chan et al., Antifibrotic effects of suramin in injured skeletal muscle after laceration. J Appl Physiol. Sep. 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.
Chang, Mouse models for studies of retinal degeneration and diseases. Methods Mol Biol. 2013;935:27-39.
Chapman, Endosomal proteases in antigen presentation. Curr Opin Immunol. Feb. 2006;18(1):78-84.
Chen et al., Adipogenic differentiation of adipose tissue-derived human mesenchymal stem cells: effect of gastric bypass surgery. Surg Endosc. Dec. 2012;26(12):3449-56.
Chen et al., Functional Human Vascular Network Generated in Photocrosslinkable Gelatin Methacrylate Hydrogels. Adv Funct Mater. May 23, 2012;22(10):2027-2039.
Chen et al., Integrated approach to designing growth factor delivery systems. FASEB J. Dec. 2007;21(14):3896-903.
Chen et al., Polymeric growth factor delivery strategies for tissue engineering. Pharm Res. Aug. 2003;20(8):1103-12.
Chen et al., Skeletal muscle stem cells. Reprod Biol Endocrinol. Nov. 13, 2003;1:101. 7 pages.
Chen et al., Spatio-temporal VEGF and PDGF delivery patterns blood vessel formation and maturation. Pharm Res. Feb. 2007;24(2):258-64.
Chiang et al., Whole tumor antigen vaccines. Semin Immunol. Jun. 2010;22(3):132-43.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001-6.
Choi, Replacement Organs, Hot Off the Press. New Scientist. 2003;177(2379):16.
Chou et al., Characterization of Photocross Linked Alginate Hydrogels for Nucleus Pulposus Cell Encapsulation. J Biomed Mater Res A. 2009;91A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al.. Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990;50(12):3487-92.
ClinicalTrials.gov, NCT00729664, Multiple Ascending Dose (MDX1105-01) (Anti-PDL1). 4 pages, Sep. 3, 2015.
ClinicalTrials.gov, NCT00730639, A Phase 1 Study of Nivolumab (BMS-936558) in Subjects with Advanced or Recurrent Malignancies (MDX1106-03). 5 pages, Mar. 24, 2016.
ClinicalTrials.gov, NCT01352884, Study to Assess the Safety, and Pharmacokinetics of AMP-224 in Patients with Advanced Cancer. 3 pages, Sep. 2, 2016.
ClinicalTrials.gov, NCT01391143, Safety Study of MGA271 in Refractory Cancer. 4 pages, Sep. 28, 2016.
Cohen et al., Controlled delivery systems for proteins based on poly(lactic/glycolic acid) microspheres. Pharm Res. Jun. 1991;8(6):713-20.
Comisar et al.. Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.

(56) References Cited

OTHER PUBLICATIONS

Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering. vol. 2. Third Edition. Pergamon Press. Chapter 4, pp. 125-171, (1978).
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inching toward the finish line. J Clin Invest. Feb. 2002;109(3):311-2.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dainiak et al., Gelatin-fibrinogen cryogel dermal matrices for wound repair: preparation, optimisation and in vitro study. Biomaterials. Jan. 2010;31(1):67-76.
Dar et al., Optimization of cardiac cell seeding and distribution in 3D porous alginate scaffolds. Biotechnol Bioeng. Nov. 5, 2002;80(3):305-12.
Daro et al.. Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts. Biophys J. Apr. 1999;76(4):2307-16.
Den Haan et al., CD8(+) but not CD8(-) dendritic cells cross-prime cytotoxic T cells in vivo. J Exp Med. Dec. 18, 2000;192(12):1685-96.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian skeletal muscle constructs engineered in vitro. In Vitro Cell Dev Biol Anim. May 2000;36(5):327-35.
Dexter et al., Conditions controlling the proliferation of haemopoietic stem cells in vitro. J Cell Physiol. Jun. 1977;91(3):335-44.
Diduch et al., Two cell lines from bone marrow that differ in terms of collagen synthesis, osteogenic characteristics, and matrix mineralization. J Bone Joint Surg Am. Jan. 1993;75(1):92-105.
Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al.. Antigens and Receptors. Lippincott's Illustrated Reviews: Immunology. Wolters Kluwer/Lippincott Williams & Wilsons, Philadelphia. Chapter 12, pp. 11-23, (2008).
Doan et al., Subcellular localization of a sporulation membrane protein is achieved through a network of interactions along and across the septum. Mol Microbiol. Mar. 2005;55(6):1767-81.
Donati et al., New hypothesis on the role of alternating sequences in calcium-alginate gels. Biomacromolecules. Mar.-Apr. 2005;6(2):1031-40.
Dong et al., Antitumor effect of secreted Flt3-ligand can act at distant tumor sites in a murine model of head and neck cancer. Cancer Gene Ther. Feb. 2003;10(2):96-104.
Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Dranoff, Cytokines in cancer pathogenesis and cancer therapy. Nat Rev Cancer. Jan. 2004;4(1):11-22.
Dranoff, GM-CSF-based cancer vaccines. Immunol Rev. Oct. 2002;188:147-54.
Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.
Dufort et al., Balancing forces: architectural control of mechanotransduction. Nat Rev Mol Cell Biol. May 2011;12(5):308-19.
Dupont et al.. Role of YAP/TAZ in mechanotransduction. Nature. Jun. 8, 2011;474(7350):179-83.
Duraiswamy et al., Dual blockade of PD-1 and CTLA-4 combined with tumor vaccine effectively restores T-cell rejection function in tumors-response. Cancer Res. Jan. 15, 2014;74(2):633-4.
Duraiswamy et al., Dual blockade of PD-1 and CTLA-4 combined with tumor vaccine effectively restores T-cell rejection function in tumors. Cancer Res. Jun. 15, 2013;73(12):3591-603.
Edwards et al.. Evaluation of biomechanical properties of human skin. Clin Dermatol. Jul.-Aug. 1995;13(4):375-80.
Egholm et al., Peptide Nucleic Acids (PNA). Oligonucleotide Analogues with an Achiral Peptide Backbone. J Am Chem Soc. 1992;114(5):1895-1897.
Egholm et al., PNA hybridizes to complementary oligonucleotides obeying the Watson-Crick hydrogen-bonding rules. Nature. Oct. 7, 1993;365(6446):566-8.
Ehrbar et al., Endothelial cell proliferation and progenitor maturation by fibrin-bound VEGF variants with differential susceptibilities to local cellular activity. J Control Release. Jan. 3, 2005;101(1-3):93-109.

(56) References Cited

OTHER PUBLICATIONS

Eiselt et al., Porous carriers for biomedical applications based on alginate hydrogels. Biomaterials. Oct. 2000;21(19):1921-7.
El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.
El-Behi et al., The encephalitogenicity of T(H)17 cells is dependent on IL-1- and IL-23-induced production of the cytokine GM-CSF. Nat Immunol. Jun. 2011;12(6):568-75.
Eldar et al., Elucidating mechanisms underlying robustness of morphogen gradients. Curr Opin Genet Dev. Aug. 2004;14(4):435-9.
Eldar et al.. Robustness of the BMP morphogen gradient in *Drosophila* embryonic patterning. Nature. Sep. 19, 2002;419(6904):304-8.
Eldar et al., Self-enhanced ligand degradation underlies robustness of morphogen gradients. Dev Cell. Oct. 2003;5(4):635-46.
Eming et al., Inflammation in wound repair: molecular and cellular mechanisms. J Invest Dermatol. Mar. 2007;127(3):514-25.
Engler et al., Matrix elasticity directs stem cell lineage specification. Cell. Aug. 25, 2006;126(4):677-89.
Engler et al., Microtissue elasticity: measurements by atomic force microscopy and its influence on cell differentiation. Methods Cell Biol. 2007;83:521-45.
Engler et al., Substrate compliance versus ligand density in cell on gel responses. Biophys J. Jan. 2004;86(1 Pt 1):617-28.
Ennett et al., Temporally regulated delivery of VEGF in vitro and in vivo. J Biomed Mater Res A. Oct. 2006;79(1):176-84.
Exposito et al., The fibrillar collagen family. Int J Mol Sci. Jan. 28, 2010;11(2):407-26.
Faissner et al., Boundaries and inhibitory molecules in developing neural tissues. Glia. Apr. 1995;13(4):233-54.
Falanga, Wound healing and its impairment in the diabetic foot. Lancet. Nov. 12, 2005;366(9498):1736-43.
Falsey et al., Peptide and small molecule microarray for high throughput cell adhesion and functional assays. Bioconjug Chem. May-Jun. 2001;12(3):346-53.
Farrar et al., T helper subset development: roles of instruction, selection, and transcription. J Clin Invest. Feb. 2002;109(4):431-5.
Fauquemberque et al., HLA-A*0201-restricted CEA-derived peptide CAP1 is not a suitable target for T-cell-based immunotherapy. J Immunother. May 2010;33(4):402-13.
Ferrara et al., Angiogenesis as a therapeutic target. Nature. Dec. 15, 2005;438(7070):967-74.
Ferrara et al., Discovery and development of bevacizumab, an anti-VEGF antibody for treating cancer. Nat Rev Drug Discov. May 2004;3(5):391-400.
Fischbach et al., Polymeric Systems for Bioinspired Delivery of Angiogenic Molecules. Adv Polym Sci. 2006;203:191-221.
Fischer et al., A brilliant monomeric red fluorescent protein to visualize cytoskeleton dynamics in Dictyostelium. FEBS Lett. Nov. 5, 2004;577(1-2):227-32.
Fischer et al., Visualizing cytoskeleton dynamics in mammalian cells using a humanized variant of monomeric red fluorescent protein. FEBS Lett. May 1, 2006;580(10):2495-502.
Fisher et al., The study of protein mechanics with the atomic force microscope. Trends Biochem Sci. Oct. 1999;24(10):379-84.
Folkman, Angiogenesis. Annu Rev Med. 2006;57:1-18.
Fonseca et al., Capitalizing on the immunogenicity of dying tumor cells. Clin Cancer Res. Mar. 15, 2008;14(6):1603-8.
Fontaine et al., Surgical treatment of peripheral circulation disorders. Helv Chir Acta. Dec. 1954;21(5-6):499-533.
Fox, Management of worsening multiple sclerosis with mitoxantrone: a review. Clin Ther. Apr. 2006;28(4):461-74.
Fransen et al., Local immunomodulation for cancer therapy: Providing treatment where needed. Oncoimmunology. Nov. 1, 2013;2(11):e26493.
Friedenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Furqan et al., STAT inhibitors for cancer therapy. J Hematol Oncol. Dec. 5, 2013;6:90. 11 pages.
Gamvrellis et al., Vaccines that facilitate antigen entry into dendritic cells. Immunol Cell Biol. Oct. 2004;82(5):506-16.
Gardel et al., Traction stress in focal adhesions correlates biphasically with actin retrograde flow speed. J Cell Biol. Dec. 15, 2008;183(6):999-1005.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3. May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.

(56) References Cited

OTHER PUBLICATIONS

GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24. 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15. 1998.
GenBank Accession No. AAH07789.1, Jun. 9, 2008.
GenBank Accession No. AAH32517.2, Jun. 9, 2008.
GenBank Accession No. AAH93731.1, Jul. 17, 2006.
GenBank Accession No. AAH94877.1, May 20. 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1. Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Gilboa, DC-based cancer vaccines. J Clin Invest. May 2007;117(5):1195-203.
Glasbey et al.. Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.
Godbey et al. Tracking the intracellular path of poly(ethylenimine)/DNA complexes for gene delivery. Proc Natl Acad Sci U S A. Apr. 27, 1999;96(9):5177-81.
Goddard et al., Polymer surface modification for the attachment of bioactive compounds. Progress in Polymer Science. Jul. 2007;32(7):698-725.
Gospodarowicz et al., Effect of fibroblast growth factor on the division and fusion of bovine myoblasts. J Cell Biol. Aug. 1976;70(2 pt 1):395-405.
Graessley, Entangled Linear, Branched and Network Polymer Systems-Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Hanada, Efficacy of rehabilitative therapy in regional musculoskeletal conditions. Best Pract Res Clin Rheumatol. Feb. 2003;17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harris et al., Open pore biodegradable matrices formed with gas foaming. J Biomed Mater Res. Dec. 5, 1998;42(3):396-402.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hashimoto et al., Development of alginate wound dressings linked with hybrid peptides derived from laminin and elastin. Biomaterials. Mar.-Apr. 2004;25(7-8):1407-14.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.

(56) References Cited

OTHER PUBLICATIONS

Helm et al., Synergy between interstitial flow and VEGF directs capillary morphogenesis in vitro through a gradient amplification mechanism. Proc Natl Acad Sci U S A. Nov. 1, 2005;102(44):15779-84.
Henry et al., VIVA Investigators. The VIVA trial: Vascular endothelial growth factor in Ischemia for Vascular Angiogenesis. Circulation. Mar. 18, 2003;107(10):1359-65.
Hermanson, Bioconjugate Techniques. Academic Press, New York. pp. 152-186, (1996).
Heslop et al., Transplanted primary neonatal myoblasts can give rise to functional satellite cells as identified using the Myf5nlacZl+ mouse. Gene Ther. May 2001;8(10):778-83.
Hildner et al., Batf3 deficiency reveals a critical role for CD8alpha+ dendritic cells in cytotoxic T cell immunity. Science. Nov. 14, 2008;322(5904):1097-100.
Hill et al., Designing scaffolds to enhance transplanted myoblast survival and migration. Tissue Eng. May 2006;12(5):1295-304.
Hill et al., Muscle satellite (stem) cell activation during local tissue injury and repair. J Anat. Jul. 2003;203(1):89-99.
Hill, Macroporous Scaffold Architecture, Peptide. HGF/FGF and Myoblast Incorporation Enhance Myogenesis. IADR/AADR/CADR 83rd General Session. Mar. 9-12, 2005. Poster #2829.
Hirano et al., Peptide and Protein Presenting Materials for Tissue Engineering. Adv Mat. Jan. 16, 2004;16(1):17-25.
Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.
Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.
Hodi et al., Improved survival with ipilimumab in patients with metastatic melanoma. N Engl J Med. Aug. 19, 2010;363(8):711-23.
Holland et al., Dual growth factor delivery from degradable oligo(poly(ethylene glycol)fumarate) hydrogel scaffolds for cartilage tissue engineering. Journal of Controlled Release. 2005;101:111-125.
Holland et al., Transforming growth factor-beta 1 release from oligo(poly(ethylene glycol)fumarate) hydrogels in conditions that model the cartilage wound healing environment. J Control Release. Jan. 8, 2004;94(1):101-14.
Horsley et al., IL-4 acts as a myoblast recruitment factor during mammalian muscle growth. Cell. May 16, 2003;113(4):483-94.
Hsiong et al., Differentiation stage alters matrix control of stem cells. J Biomed Mater Res A. Apr. 2008;85A(1):145-56.
Huang et al., Fabrication and in vitro Testing of Polymeric Delivery Systems for Condensed DNA. J Biomed Mater Res. 2003;67:1384-1392.
Huang et al., Long-Term in Vivo Gene Expression via Delivery of PEL-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands at a glance. J Cell Sci. Oct. 1, 2006;119(Pt 19):3901-3.
Huston et al.. Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al.. Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003. 12 pages.
Ichida et al., A small-molecule inhibitor of tgf-Beta signaling replaces sox2 in reprogramming by inducing nanog. Cell Stem Cell. Nov. 6, 2009;5(5):491-503.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Isern et al., Self-renewing human bone marrow mesenspheres promote hematopoietic stem cell expansion. Cell Rep. May 30, 2013;3(5):1714-24.
Ishihara et al., Roles of bradykinin in vascular permeability and angiogenesis in solid tumor. Int Immunopharmacol. Mar. 2002;2(4):499-509.
Iwamoto et al., Preparation of an Ionic Polymer Gel Microactuator and Measurement of its Periodic Motions. Nippon Kagaku Kaishi. 1997;9:609-614.
Jain, Molecular Regeneration of Vessel Maturation. Nat Med. Jun. 1, 2003;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(-/-) setting. Immunity. Mar. 2002;16(3):429-39.
Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jiang et al. Two-piconewton slip bond between fibronectin and the cytoskeleton depends on talin. Nature. Jul. 17, 2003;424(6946):334-7.
Jiang et al., Click hydrogels, microgels and nanogels: emerging platforms for drug delivery and tissue engineering. Biomaterials. Jun. 2014;35(18):4969-85.
Jiang et al., Self-organization of periodic patterns by dissociated feather mesenchymal cells and the regulation of size, number and spacing of primordia. Development. Nov. 1999;126(22):4997-5009.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;117(7):1902-13.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jugdutt et al., Aging and defective healing, adverse remodeling, and blunted post-conditioning in the reperfused wounded heart. J Am Coll Cardiol. Apr. 8, 2008;51(14):1399-403.
Juntanon et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels. J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.

(56) References Cited

OTHER PUBLICATIONS

Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Katayama et al., Integrated analysis of the genome and the transcriptome by FANTOM. Brief Bioinform. Sep. 2004;5(3):249-58.
Kathuria et al., Synthesis and characterization of elastic and macroporous chitosan-gelatin cryogels for tissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.
Kennedy et al., Rapid and extensive collapse from electrically responsive macroporous hydrogels. Adv Healthc Mater. Apr. 2014;3(4):500-7.
Khetan et al., Degradation-mediated cellular traction directs stem cell fate in covalently crosslinked three-dimensional hydrogels. Nat Mater. May 2013;12(5):458-65.
Khownium et al., Novel endotoxin-sequestering compounds with terephthalaldehyde-bis-guanylhydrazone scaffolds. Bioorg Med Chem Lett. Mar. 1, 2006;16(5):1305-8.
Kim et al., An overview of cartilage tissue engineering. Yonsei Med J. Dec. 2000;41(6):766-73.
Kim et al., Multifunctional capsule-in-capsules for immunoprotection and trimodal imaging. Angew Chem Int Ed Engl. Mar. 1, 2011;50(10):2317-21.
Kim et al., The effect of VEGF on the myogenic differentiation of adipose tissue derived stem cells within thermosensitive hydrogel matrices. Biomaterials. Feb. 2010;31(6):1213-8.
Kinoshita et al., Successive injections in mdx mice of myoblasts grown with bFGF. Neuromuscul Disord. May 1996;6(3):187-93.
Kisak et al. The vesosome—a multicompartment drug delivery vehicle. Curr Med Chem. Jan. 2004;11(2):199-219.
Klebanoff et al., CD8+ T-cell memory in tumor immunology and immunotherapy. Immunol Rev. Jun. 2006;211:214-24.
Klein et al., Cell-Cycle Control by Physiological Matrix Elasticity and in Viivo Tissue Stiffening. Curr Biol. Sep. 29, 2009;19:1511-1518.
Klinman, Immunotherapeutic uses of CpG oligodeoxynucleotides. Nat Rev Immunol. Apr. 2004;4(4):249-58.
Kohane, Microparticles and nanoparticles for drug delivery. Biotechnol Bioeng. Feb. 1, 2007;96(2):203-9.
Kondo et al., A reaction-diffusion wave on the skin of the marine angelfish Pomacanthus. Nature. Aug. 31, 1995;376(6543):765-8.
Kong et al., Controlling Degradation of Hydrogels via the Size of Cross-Linked Junctions. Adv Mater. Nov. 30, 2004;16(21):1917-1921.
Kong et al., Controlling rigidity and degradation of alginate hydrogels via molecular weight distribution. Biomacromolecules. Sep.-Oct. 2004;5(5):1720-7.
Kong et al., Decoupling the Dependence of Rheological/Mechanical Properties of Hydrogels from Solids Concentration. Polymer. 2002;43(23):6239-6246.
Kong et al., Design of biodegradable hydrogel for the local and sustained delivery of angiogenic plasmid DNA. Pharm Res. May 2008;25(5):1230-8.
Kong et al., Designing alginate hydrogels to maintain viability of immobilized cells. Biomaterials. Oct. 2003;24(22):4023-9.
Kong et al., FRET measurements of cell-traction forces and nanoscale clustering of adhesion ligands varied by substrate stiffness. Proc Natl Acad Sci U S A. Mar. 22, 2005;102(12):4300-5.
Kong et al., Non-viral gene delivery regulated by stiffness of cell adhesion substrates. Nat Mater. Jun. 2005;4(6):460-4.
Koo et al., Bioorthogonal copper-free click chemistry in vivo for tumor-targeted delivery of nanoparticles. Angew Chem Int Ed Engl. Nov. 19, 2012;51(47):11836-40.
Kratky et al., Direct activation of antigen-presenting cells is required for CD8+ T-cell priming and tumor vaccination. Proc Natl Acad Sci U S A. Oct. 18, 2011;108(42):17414-9.
Kratz, Albumin as a drug carrier: design of prodrugs, drug conjugates and nanoparticles. J Control Release. Dec. 18, 2008;132(3):171-83.
Krieg, Development of TLR9 agonists for cancer therapy. J Clin Invest. May 2007;117(5):1184-94.
Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.
Kumamoto et al., Induction of tumor-specific protective immunity by in situ Langerhans cell vaccine. Nat Biotechnol. Jan. 2002;20(1):64-9.
Kumar et al., Toll-like receptors and innate immunity. Biochem Biophys Res Commun. Oct. 30, 2009;388(4):621-5.
Kupferschmidt et al., Mesoporous silica particles potentiate antigen-specific T-cell responses. Nanomedicine (Lond). 2014;9(12):1835-46.
Kuwahara et al., Cell delivery using an injectable and adhesive transglutaminase-gelatin gel. Tissue Eng Part C Methods. Aug. 2010;16(4):609-18.
Kwon et al., Electrically erodible polymer gel for controlled release of drugs. Nature. Nov. 28, 1991;354(6351):291-3.
Kwon et al., In vivo targeting of dendritic cells for activation of cellular immunity using vaccine carriers based on pH-responsive microparticles. Proc Natl Acad Sci U S A. Dec. 20, 2005;102(51):18264-8.
Kyi et al., Checkpoint blocking antibodies in cancer immunotherapy. FEBS Lett. Jan. 21, 2014;588(2):368-76.
Langenkamp et al., Kinetics of dendritic cell activation: impact on priming of TH1, TH2 and nonpolarized T cells. Nat Immunol. Oct. 2000;1(4):311-6.
Langer et al., Tissue engineering. Science. May 14, 1993;260(5110):920-6.
Lanzavecchia et al., Regulation of T cell immunity by dendritic cells. Cell. Aug. 10, 2001;106(3):263-6.
Lao et al., Magnetic and hydrogel composite materials for hyperthermia applications. J Mater Sci Mater Med. Oct. 2004;15(10):1061-4.
Latorre et al., Applications of magnetic nanoparticles in medicine: magnetic fluid hyperthermia. P R Health Sci J. Sep. 2009;28(3):227-38.
Latz et al., TLR9 signals after translocating from the ER to CpG DNA in the lysosome. Nat Immunol. Feb. 2004;5(2):190-8.
Lauterbach et al., Mouse CD8alpha+ DCs and human BDCA3+ DCs are major producers of IFN-lambda in response to poly IC. J Exp Med. Nov. 22, 2010;207(12):2703-17.
Leach et al., Coating of VEGF-releasing scaffolds with bioactive glass for angiogenesis and bone regeneration. Biomaterials. Jun. 2006;27(17):3249-55.
Lee et al., Controlling Mechanical and Swelling Properties of Alginate Hydrogels Independently by Cross-Linker Type and Cross-Linking Density. Macromolecules. Apr. 2000;33(11):4291-4294.
Lee et al., Engineering liver tissue spheroids with inverted colloidal crystal scaffolds. Biomaterials. Sep. 2009;30(27):4687-94.
Lee et al., Hydrogel Formation via Vell Crosslinking. Advanced Materials. Nov. 2003;15(21):1828-1832.
Lee et al., Hydrogels for tissue engineering. Chem Rev. Jul. 2001;101(7):1869-79.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.
Lefaucheur et al., The cellular events of injured muscle regeneration depend on the nature of the injury. Neuromuscul Disord. Nov. 1995;5(6):501-9.

(56) References Cited

OTHER PUBLICATIONS

Lele et al., Investigating complexity of protein-protein interactions in focal adhesions. Biochem Biophys Res Commun. May 9, 2008;369(3):929-34.
Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.
Levental et al.. Soft biological materials and their impact on cell function. Soft Matter. 2007;3:299-306.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.
Li et al., Mesoporous silica nanoparticles in biomedical applications. Chem Soc Rev. Apr. 7, 2012;41(7):2590-605.
Li et al., pH sensitive Laponite/alginate hybrid hydrogels: swelling behaviour and release mechanism. Soft Matter. 2011;7:6231-6238.
Li et al., Purified hybrid cells from dendritic cell and tumor cell fusions are superior activators of antitumor immunity. Cancer Immunol Immunother. Nov. 2001;50(9):456-62.
Li et al., Recent advances of biomaterials in biotherapy. Regen Biomater. Jun. 2016;3(2):99-105.
Li, TNF-alpha is a mitogen in skeletal muscle. Am J Physiol Cell Physiol. Aug. 2003;285(2):C370-6.
Liederer et al., Enzymes involved in the bioconversion of ester-based prodrugs. J Pharm Sci. Jun. 2006;95(6):1177-95.
Lin et al., Transdermal regulation of vascular network bioengineering using a photopolymerizable methacrylated gelatin hydrogel. Biomaterials. Sep. 2013;34(28):6785-96.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu et al., Preparation of uniform calcium alginate gel beads by membrane emulsification coupled with internal gelation. Journal of Applied Polymer Science. Nov. 22, 2002;87(5):848-852.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Urology. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Lutterotti et al., Antigen-specific tolerance by autologous myelin peptide-coupled cells: a phase 1 trial in multiple sclerosis. Sci Transl Med. Jun. 5, 2013;5(188):188ra75.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Mahony et al., Mesoporous silica nanoparticles act as a self-adjuvant for ovalbumin model antigen in mice. Small. Sep. 23, 2013;9(18):3138-46.
Mainz, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.
Mammoto et al., Mechanical control of tissue and organ development. Development. May 2010;137(9):1407-20.
Manavski et al., Vascular niche controls organ regeneration. Circ Res. Mar. 28, 2014;114(7):1077-9.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci USA. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKay et al., Click chemistry in complex mixtures: bioorthogonal bioconjugation. Chem Biol. Sep. 18, 2014;21(9):1075-101.

(56) References Cited

OTHER PUBLICATIONS

McKinney-Freeman et al., Muscle-derived hematopoietic stem cells are hematopoietic in origin. Proc Natl Acad Sci U S A. Feb. 5, 2002;99(3):1341-6.

McKinnon et al., Biophysically defined and cytocompatible covalently adaptable networks as viscoelastic 3D cell culture systems. Adv Mater. Feb. 12, 2014;26(6):865-72.

McPherron et al., Regulation of skeletal muscle mass in mice by a new TGF-beta superfamily member. Nature. May 1, 1997;387(6628):83-90.

McQualter et al., Granulocyte macrophage colony-stimulating factor: a new putative therapeutic target in multiple sclerosis. J Exp Med. Oct. 1, 2001;194(7):873-82.

McWhorter et al., Modulation of macrophage phenotype by cell shape. Proc Natl Acad Sci U S A. Oct. 22, 2013;110(43):17253-8.

Mehta et al., Engineering New Approaches to Cancer Vaccines. Cancer Immunol Res. Aug. 2015;3(8):836-43.

Meier et al., Peptide Nucleic Acids(PNAs)—Unusual Properties of Noionic Oligonucleotide Analogues. Angewandte Chemie, Int'l Edition. Aug. 1992;31(8):1008-1010.

Melero-Martin et al., Engineering robust and functional vascular networks in vivo with human adult and cord blood-derived progenitor cells. Circ Res. Jul. 18, 2008;103(2):194-202. Includes supplementary materials.

Melief et al., Immunotherapy of established (pre)malignant disease by synthetic long peptide vaccines. Nat Rev Cancer. May 2008;8(5):351-60.

Mellman et al., Dendritic cells: specialized and regulated antigen processing machines. Cell. Aug. 10, 2001;106(3):255-8.

Menetry et al., Suturing Versus Immobilization of a Muscle Laceration: A Morphological and Functional Study in a Mouse Model. Am J Sports Med. 1999;27(2):222-229.

Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.

Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.

Merkel et al., Using mechanobiological mimicry of red blood cells to extend circulation times of hydrogel microparticles. Proc Natl Acad Sci U S A. Jan. 11, 2011;108(2):586-91.

Merriam-Webster, Transient. Merriam-Webster Dictionary. Web. Jul. 18, 2014. www.merriam-webster.com/dictionary/transient. 3 pages.

Metters et al., Fundamental studies of biodegradable hydrogels as cartilage replacement materials. Biomed Sci Instrum. 1999;35:33-8.

Meyer et al., Clinical investigations of Toll-like receptor agonists. Expert Opin Investig Drugs. Jul. 2008;17(7):1051-65.

Meylan et al., Intracellular pattern recognition receptors in the host response. Nature. Jul. 6, 2006;442(7098):39-44.

MGI, Mouse Facts. Retrieved online at: http://www.informatics.jax.org/mgihome/other/mouse_facts1.shtml. 2 pages. Jul. 31, 2018.

Miljkovic et al., Chondrogenesis, bone morphogenetic protein-4 and mesenchymal stem cells. Osteoarthritis Cartilage. Oct. 2008;16(10):1121-30.

Miller et al., Hepatocyte growth factor affects satellite cell activation and differentiation in regenerating skeletal muscle. Am J Physiol Cell Physiol. Jan. 2000;278(1):C174-81.

Miller et al., Lipopolysaccharide sequestrants: structural correlates of activity and toxicity in novel acylhomospermines. J Med Chem. Apr. 7, 2005;48(7):2589-99.

Miller et al., Melanoma. N Engl J Med. Jul. 6, 2006;355(1):51-65.

Miralles et al., Actin dynamics control SRF activity by regulation of its coactivator MAL. Cell. May 2, 2003;113(3):329-42.

Mitchell et al., The exogenous administration of basic fibroblast growth factor to regenerating skeletal muscle in mice does not enhance the process of regeneration. Growth Factors. 1996;13(1-2):37-55.

Miyata et al., Biomolecule-sensitive hydrogels. Adv Drug Deliv Rev. Jan. 17, 2002;54(1):79-98.

Mohan et al., Novel Porous, Polysaccharide Scaffolds for Tissue Engineering Applications. Trends Biomater Artif Organs. 2005;18(2):219-224.

Moioli et al., Matrices and scaffolds for drug delivery in dental, oral and craniofacial tissue engineering. Adv Drug Deliv Rev. May 30, 2007;59(4-5):308-24.

Molinari et al., Modification of surface membrane antigens by trypsin. Proc Soc Exp Biol Med. Apr. 1975;148(4):991-4.

Molloy et al., Movement and force produced by a single myosin head. Nature. Nov. 9, 1995;378(6553):209-12.

Mooney et al., Cytoskeletal filament assembly and the control of cell spreading and function by extracellular matrix. J Cell Sci. Jun. 1995;108 (Pt 6):2311-20.

Mooney et al., Switching from differentiation to growth in hepatocytes: control by extracellular matrix. J Cell Physiol. Jun. 1992;151(3):497-505.

Moser et al., Dendritic cell regulation of TH1-TH2 development. Nat Immunol. Sep. 2000;1(3):199-205.

Mulder et al., Wound Management: Past, Present, and Future. Clinicians' Pocket Guide to Chronic Wound Repair. Springhouse Corporation, Springhouse, Pennsylvania. 1998:85-90.

Muralidharan-Chari et al., ARF6-regulated shedding of tumor cell-derived plasma membrane microvesicles. Curr Biol. Dec. 1, 2009;19(22):1875-85.

Murdan, Electro-responsive drug delivery from hydrogels. J Control Release. Sep. 19, 2003;92(1-2):1-17.

Nagai et al., A variant of yellow fluorescent protein with fast and efficient maturation for cell-biological applications. Nat Biotechnol. Jan. 2002;20(1):87-90.

Naik et al., Development of plasmacytoid and conventional dendritic cell subtypes from single precursor cells derived in vitro and in vivo. Nat Immunol. Nov. 2007;8(11):1217-26.

NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.

Nehls et al., A novel, microcarrier-based in vitro assay for rapid and reliable quantification of three-dimensional cell migration and angiogenesis. Microvasc Res. Nov. 1995;50(3):311-22.

Nestle et al., Vaccination of melanoma patients with peptide- or tumorlysate-pulsed dendritic cells. Nature Medicine. Mar. 1, 1998;4(3):328-32.

Niamlang et al., Electrically controlled release of salicylic acid from poly(p-phenylene vinylene)/polyacrylamide hydrogels. Int J Pharm. Apr. 17, 2009;371(1-2):126-33.

Nichol et al., Cell-laden microengineered gelatin methacrylate hydrogels. Biomaterials. Jul. 2010;31(21):5536-44.

Nicodemus et al., Cell encapsulation in biodegradable hydrogels for tissue engineering applications. Tissue Eng Part B Rev. Jun. 2008;14(2):149-65.

(56) References Cited

OTHER PUBLICATIONS

Niessen et al., The alpha 6 beta 4 integrin is a receptor for both laminin and kalinin. Exp Cell Res. Apr. 1994;211(2):360-7.
NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).
Noguera-Troise et al., Blockade of Dll4 inhibits tumour growth by promoting non-productive angiogenesis. Nature. Dec. 21, 2006;444(7122):1032-7.
Nuttelman et al., Dexamethasone-functionalized gels induce osteogenic differentiation of encapsulated hMSCs. J Biomed Mater Res A. Jan. 2006;76(1):183-95.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000;1(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistance-forming modification. Science. Aug. 31, 2012;337(6098):1111-5.
Oldenhove et al., Decrease of Foxp3+ Treg cell number and acquisition of effector cell phenotype during lethal infection. Immunity. Nov. 20, 2009;31(5):772-86.
Oneto et al., Implantable biomaterial based on click chemistry for targeting small molecules. Acta Biomaterialia. 2014;10:5099-5105.
Orner et al., Arrays for the combinatorial exploration of cell adhesion. J Am Chem Soc. Sep. 8, 2004;126(35):10808-9.
Osunkoya et al., Synthesis and fate of immunological surface receptors on cultured Burkitt lymphoma cells. Int J Cancer. Mar. 15, 1969;4(2):159-65.
Ota et al., Percutaneous subxiphoid access to the epicardium using a miniature crawling robotic device. Innovations (Phila). 2006 Fall;1(5):227-31.
Overwijk et al., Tumor regression and autoimmunity after reversal of a functionally tolerant state of self-reactive CD8+ T cells. J Exp Med. Aug. 18, 2003;198(4):569-80.
Ozawa et al., Microenvironmental VEGF concentration, not total dose, determines a threshold between normal and aberrant angiogenesis. J Clin Invest. Feb. 2004;113(4):516-27.
Padilla et al., Insufficient TLR activation contributes to the slow development of CD8+ T cell responses in Trypanosoma cruzi infection. J Immunol. Jul. 15, 2009;183(2):1245-52.
Page-McCaw et al., Matrix metalloproteinases and the regulation of tissue remodelling. Nat Rev Mol Cell Biol. Mar. 2007;8(3):221-33.
Pailler-Mattei et al., In vivo measurements of the elastic mechanical properties of human skin by indentation tests. Med Eng Phys. Jun. 2008;30(5):599-606.
Pajonk et al., From sol-gel to aerogels and cryogels. J Non Cryst Solids. May 1990;121(1-3):66-67.
Palacio et al., Interleukin 10 and tumor necrosis factor alpha gene expression in respiratory and peripheral muscles. Relation to sarcolemmal damage. Arch Bronconeumol. Jul. 2002;38(7):311-6.
Paradee et al., Effects of crosslinking ratio, model drugs, and electric field strength on electrically controlled release for alginate-based hydrogel. J Mater Sci Mater Med. Apr. 2012;23(4):999-1010.
Pardoll, The blockade of immune checkpoints in cancer immunotherapy. Nat Rev Cancer. Mar. 22, 2012;12(4):252-64.
Parekh et al., Modulus-driven differentiation of marrow stromal cells in 3D scaffolds that is independent of myosin-based cytoskeletal tension. Biomaterials. Mar. 2011;32(9):2256-64.
Parekkadan et al., Mesenchymal stem cell-derived molecules reverse fulminant hepatic failure. PLoS One. Sep. 26, 2007;2(9):e941.
Park et al., Photopolymerized hyaluronic acid-based hydrogels and interpenetrating networks. Biomaterials. Mar. 2003;24(6):893-900.
Parker et al., Effect of mitoxantrone on outcome of children with first relapse of acute lymphoblastic leukaemia (ALL R3): an open-label randomised trial. Lancet. Dec. 11, 2010;376(9757):2009-17.
Partridge et al., Conversion of mdx myofibres from dystrophin-negative to -positive by injection of normal myoblasts. Nature. Jan. 12, 1989;337(6203):176-9.
Pawlaczyk et al., Age-dependent biomechanical properties of the skin. Postepy Dermatol Alergol. Oct. 2013;30(5):302-6.
Pedersen et al., Induction of regulatory dendritic cells by dexamethasone and 1alpha,25-Dihydroxyvitamin D(3). Immunol Lett. Jan. 30, 2004;91(1):63-9.
Pek et al., The effect of matrix stiffness on mesenchymal stem cell differentiation in a 3D thixotropic gel. Biomaterials. Jan. 2010;31(3):385-91.
Pelinkovic et al., Tissue engineering and gene therapy of the musculoskeletal system with muscle cells. Z Orthop Ihre Grenzgeb. Sep.-Oct. 2000;138(5):402-6.
Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.
Peters et al., Engineering vascular networks in porous polymer matrices. J Biomed Mater Res. Jun. 15, 2002;60(4):668-78.
Peyton et al., The use of poly(ethylene glycol) hydrogels to investigate the impact of ECM chemistry and mechanics on smooth muscle cells. Biomaterials. Oct. 2006;27(28):4881-93.
Phillippi, Patterning of Multiple Cell Lineages from a Single Stem Cell Population. Annual Meeting of the American Society for Cell Biology. Dec. 10, 2006.
Pinho et al., PDGFRa and CD51 mark human nestin+ sphere-forming mesenchymal stem cells capable of hematopoietic progenitor cell expansion. J Exp Med. Jul. 1, 2013;210(7):1351-67.
Platten et al., Cancer Immunotherapy by Targeting IDO1/TDO and Their Downstream Effectors. Front Immunol. Jan. 12, 2015;5:673. 7 pages.
Pluen et al., Role of tumor-host interactions in interstitial diffusion of macromolecules: cranial vs. subcutaneous tumors. Proc Natl Acad Sci U S A. Apr. 10, 2001;98(8):4628-33.
Pooyan et al., Conjugates bearing multiple formyl-methionyl peptides display enhanced binding to but not activation of phagocytic cells. Bioconjug Chem. Mar.-Apr. 2002;13(2):216-23.
Pope et al., Organ-specific regulation of the CD8 T cell response to Listeria monocytogenes infection. J Immunol. Mar. 1, 2001;166(5):3402-9.
Porter et al., Separation of Natural Populations of Coliform Bacteria from Freshwater and Sewage by Magnetic-Bead Cell Sorting. J Microbiol Meth. 1998;33(3):221-226.
Pouzet et al., Factors affecting functional outcome after autologous skeletal myoblast transplantation. Ann Thorac Surg. Mar. 2001;71(3):844-50; discussion 850-1.
PRNewsWire, GlaxoSmithKline and Amplimmune Form Global Strategic Collaboration. Alliance to Focus on AMP-224 for Cancer and Other Diseases. 3 pages, Aug. 4, 2010.
Pulendran et al., Flt3-ligand and granulocyte colony-stimulating factor mobilize distinct human dendritic cell subsets in vivo. J Immunol. Jul. 1, 2000;165(1):566-72.
Qi et al., Patterned differentiation of individual embryoid bodies in spatially organized 3D hybrid microgels. Adv Mater. Dec. 7, 2010;22(46):5276-81.
Qin et al., Soft lithography for micro- and nanoscale patterning. Nat Protoc. Mar. 2010;5(3):491-502.
Qiu et al., Environment-sensitive hydrogels for drug delivery. Adv Drug Deliv Rev. Dec. 31, 2001;53(3):321-39.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.

(56) References Cited

OTHER PUBLICATIONS

Quezada et al., CTLA4 blockade and GM-CSF combination immunotherapy alters the intratumor balance of effector and regulatory T cells. J Clin Invest. Jul. 2006;116(7):1935-45.
Quintana et al., Autoantibody patterns in diabetes-prone NOD mice and in standard C57BL/6 mice. J Autoimmun. Nov. 2001;17(3):191-7.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.
Ramon-Azcon et al., Gelatin methacrylate as a promising hydrogel for 3D microscale organization and proliferation of dielectrophoretically patterned cells. Lab on a Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al., Macrophage-derived growth factors. Curr Top Microbiol Immunol. 1992;181:87-140.
Rapraeger, Syndecan-regulated receptor signaling. J Cell Biol. May 29, 2000;149(5):995-8.
Reddy et al., Exploiting lymphatic transport and complement activation in nanoparticle vaccines. Nat Biotechnol. Oct. 2007;25(10):1159-64.
Reimann et al., Satellite Cells in Normal and Regenerated Soleus Muscles of mdx and Control Mice. Eur J Neurosci. 1998;10:366, Abstract No. 153.07.
Reis E Sousa., Activation of dendritic cells: translating innate into adaptive immunity. Curr Opin Immunol. Feb. 2004;16(1):21-5.
Research Results of National Institute of Advanced Industrial Science and Technology, retrieved online at: http://www.aist.go.jp/aist_j/press_release/pr2006/pr20060719.html. 4 pages, (2006).
Rhoads et al., Satellite cell-mediated angiogenesis in vitro coincides with a functional hypoxia-inducible factor pathway. Am J Physiol Cell Physiol. Jun. 2009;296(6):C1321-8.
Ribas et al., Phase III randomized clinical trial comparing tremelimumab with standard-of-care chemotherapy in patients with advanced melanoma. J Clin Oncol. Feb. 10, 2013;31(5):616-22.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Cancer immunotherapy: moving beyond current vaccines. Nat Med. Sep. 2004;10(9):909-15.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-9.
Sansonetti, The innate signaling of dangers and the dangers of innate signaling. Nat Immunol. Dec. 2006;7(12):1237-42.
Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.
Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.

(56) References Cited

OTHER PUBLICATIONS

Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from Discosoma sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheppard et al., Polyethyleneimine is a potent systemic adjuvant for glycoprotein antigens. Int Immunol. Oct. 2014;26(10):531-8.
Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.
Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simmons et al., GM-CSF as a systemic adjuvant in a phase II prostate cancer vaccine trial. Prostate. Jun. 1, 1999;39(4):291-7.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Skokos et al.. CD8-DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Sletten et al., A hydrophilic azacyclooctyne for Cu-free click chemistry. Org Lett. Jul. 17, 2008;10(14):3097-9.
Smidsrod et al., Alginate as immobilization matrix for cells. Trends Biotechnol. Mar. 1990;8(3):71-8.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Stachowiak et al., Inverse opal hydrogel-collagen composite scaffolds as a supportive microenvironment for immune cell migration. J Biomed Mater Res A. Jul. 1, 2008;85(3):815-28.
Steinman et al., Taking dendritic cells into medicine. Nature. Sep. 27, 2007;449(7161):419-26.
Stockmann et al., Exploring isonitrile-based click chemistry for ligation with biomolecules. Organic & Biomolecular Chemistry. 2011;9:7300-7302.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. Oct. 20, 1997;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.
Sun et al., Highly stretchable and tough hydrogels. Nature. Sep. 6, 2012;489(7414):133-6.
Sun et al., Sustained vascular endothelial growth factor delivery enhances angiogenesis and perfusion in ischemic hind limb. Pharm Res. Jul. 2005;22(7):1110-6.
Suri et al., Photopatterned collagen-hyaluronic acid interpenetrating polymer network hydrogels. Acta Biomater. Sep. 2009;5(7):2385-97.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Swift et al., Nuclear lamin—A scales with tissue stiffness and enhances matrix-directed differentiation. Science. Aug. 30, 2013;341(6149):1240104. 17 pages.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor Impregnated in Gelatin Hydrogels. Journal of Controlled Release. Sep. 1994;31(2):189-199.
Takahashi et al., Induction of pluripotent stem cells from adult human fibroblasts by defined factors. Cell. Nov. 30, 2007;131(5):861-72.
Takeshita et al., Therapeutic angiogenesis. A single intraarterial bolus of vascular endothelial growth factor augments revascularization in a rabbit ischemic hind limb model. J Clin Invest. Feb. 1994;93(2):662-70.
Tamura et al.. Immunotherapy of tumors with autologous tumor-derived heat shock protein preparations. Science. Oct. 3, 1997;278(5335):117-20.
Tanaka et al., Collapse of gels in an electric field. Science. Oct. 29, 1982;218(4571):467-9.
Tang et al., Combining radiation and immunotherapy: a new systemic therapy for solid tumors? Cancer Immunol Res. Sep. 2014;2(9):831-8.
Tannous, Gaussia luciferase reporter assay for monitoring biological processes in culture and in vivo. Nat Protoc. 2009;4(4):582-91.
Tatsumi et al., HGF/SF is present in normal adult skeletal muscle and is capable of activating satellite cells. Dev Biol. Feb. 1, 1998;194(1):114-28.

(56) References Cited

OTHER PUBLICATIONS

Ten Dijke et al., Growth Factors for Wound Healing. Nat Biotechnol. 1989;7:793-798.
Thelin et al., In Vivo Enrichment of Diabetogenic T Cells. Diabetes. Aug. 2017;66(8):2220-2229.
Thomas et al., Intravenous infusion of bone marrow in patients receiving radiation and chemotherapy. N Engl J Med. Sep. 12, 1957;257(11):491-6.
Thornton et al., Shape retaining injectable hydrogels for minimally invasive bulking. J Urol. Aug. 2004;172(2):763-8.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatory cell response to acute muscle injury. Med Sci Sports Exerc. Jul. 1995;27(7):1022-32.
Tomer et al., Electrically Controlled Release of Macromolecules from Cross-Linked Hyaluronic Acid Hydrogels. Journal of Controlled Release. Mar. 1995:33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chem Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tripathi et al., Elastic and macroporous agarose-gelatin cryogels with isotropic and anisotropic porosity for tissue engineering. J Biomed Mater Res A. Sep. 1, 2009;90(3):680-94.
Tsien, The green fluorescent protein. Annu Rev Biochem. 1998;67:509-44.
Turing, Discussion: Turing's Theory of Morphogenesis—Its Influence on Modelling Biological Pattern and Form. Bull Math Biol. 1990;52(1-2):119-159.
Turing, The Chemical Basis of Morphogenesis. Philosophical Transactions of the Royal Society of London. Series B. 1952;237(641):37-72.
Uchida et al., Immunization by particle bombardment of antigen-loaded poly-(DL-lactide-co-glycolide) microspheres in mice. Vaccine. Mar. 15, 2006;24(12):2120-30.
Udono, Cancer immunotherapy with blocking of immune checkpoint. Journal of Okayama Medical Association. Apr. 2013;125:13-18.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19. 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2. Jun. 11, 2014.
UniProtKB/Swiss-Prot Accession No. Q9NZQ7.1. Apr. 16, 2014.
Urbanek et al., Stem cell niches in the adult mouse heart. Proc Natl Acad Sci U S A. Jun. 13, 2006;103(24):9226-31.
Van Berkel et al., Metal-free triazole formation as a tool for bioconjugation. Chembiochem. Sep. 3, 2007;8(13):1504-8.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Vandenburgh et al., Tissue-engineered skeletal muscle organoids for reversible gene therapy. Hum Gene Ther. Nov. 10, 1996;7(17):2195-200.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.
Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculoskeletal Disease Revealed in new WHO Report. Bull World Health Organ. 2003;81(11):853-854.
W.H.O., World Health Organization, the World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):16745-9.

(56) References Cited

OTHER PUBLICATIONS

Wang et al., Mechanotransduction at a distance: mechanically coupling the extracellular matrix with the nucleus. Nat Rev Mol Cell Biol. Jan. 2009;10(1):75-82.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Wegmann et al., Polyethyleneimine is a potent mucosal adjuvant for viral glycoprotein antigens. Nat Biotechnol. Sep. 2012;30(9):883-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.
Xie et al., Preparation and Application of Surface-Coated Superparamagnetic Nanobeads in the Isolation of Genomic DNA. J Magn Magnetic Mater. Jun. 2004;277(1-2):16-23.
Xiong et al., Transcription Factor STAT3 as a Novel Molecular Target for Cancer Prevention. Cancers (Basel). Apr. 16, 2014;6(2):926-57.
Yamazaki et al., CD8+ CD205+ splenic dendritic cells are specialized to induce Foxp3+ regulatory T cells. J Immunol. Nov. 15, 2008;181(10):6923-33.

Yancopoulos et al., Vascular-specific growth factors and blood vessel formation. Nature. Sep. 14, 2000;407(6801):242-8.
Yang et al., The effect of incorporating RGD adhesive peptide in polyethylene glycol diacrylate hydrogel on osteogenesis of bone marrow stromal cells. Biomaterials. Oct. 2005;26(30):5991-8.
Yeung et al., Effects of substrate stiffness on cell morphology, cytoskeletal structure, and adhesion. Cell Motil Cytoskeleton. Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Sequence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science. Dec. 21, 2007;318(5858):1917-20.
Yuen et al., Mimicking nature by codelivery of stimulant and inhibitor to create temporally stable and spatially restricted angiogenic zones. Proc Natl Acad Sci U S A. Oct. 19, 2010;107(42):17933-8.
Yuk et al., Electric current-sensitive drug delivery systems using sodium alginate/polyacrylic acid composites. Pharm Res. Jul. 1992;9(7):955-7.
Zammit et al., Kinetics of myoblast proliferation show that resident satellite cells are competent to fully regenerate skeletal muscle fibers. Exp Cell Res. Nov. 15, 2002;281(1):39-49.
Zammit et al., Muscle satellite cells adopt divergent fates: a mechanism for self-renewal? J Cell Biol. Aug. 2, 2004;166(3):347-57.
Zeltinger et al., Effect of pore size and void fraction on cellular adhesion, proliferation, and matrix deposition. Tissue Eng. Oct. 2001;7(5):557-72.
Zemel et al.. Optimal matrix rigidity for stress fiber polarization in stem cells. Nat Phys. Jun. 1, 2010;6(6):468-473.
Zhang et al., A comparative study of the antigen-specific immune response induced by co-delivery of CpG ODN and antigen using fusion molecules or biodegradable microparticles. J Pharm Sci. Dec. 2007;96(12):3283-92.
Zhang et al., A tension-induced mechanotransduction pathway promotes epithelial morphogenesis. Nature. Mar. 3, 2011;471(7336):99-103.
Zhang et al., Generation of a syngeneic mouse model to study the effects of vascular endothelial growth factor in ovarian carcinoma. Am J Pathol. Dec. 2002;161(6):2295-309.
Zhang et al., Talin depletion reveals independence of initial cell spreading from integrin activation and traction. Nat Cell Biol. Sep. 2008;10(9):1062-8.
Zhao et al., A cell-permeable Stat3 SH2 domain mimetic inhibits Stat3 activation and induces antitumor cell effects in vitro. J Biol Chem. Nov. 12, 2010;285(46):35855-65.
Zhao et al., Active scaffolds for on-demand drug and cell delivery. Proc Natl Acad Sci U S A. Jan. 4, 2011;108(1):67-72.
Zhao et al., Directed cell migration via chemoattractants released from degradable microspheres. Biomaterials. Aug. 2005;26(24):5048-63.
Zhao et al., Stress-relaxation behavior in gels with ionic and covalent crosslinks. J Appl Phys. Mar. 15, 2010;107(6):63509.
Zhou et al., Instability of the transcription factor Foxp3 leads to the generation of pathogenic memory T cells in vivo. Nat Immunol. Sep. 2009;10(9):1000-7.
Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.
Zizzari et al., The Macrophage Galactose-Type C-Type Lectin (MGL) Modulates Regulatory T Cell Functions. PLoS One. Jul. 6, 2015;10(7):e0132617. 12 pages.
Japanese Office Action for Application No. 2016-565339, dated Jan. 8, 2019. 9 pages.
Ambrosini et al., Astrocytes produce dendritic cell-attracting chemokines in vitro and in multiple sclerosis lesions. J Neuropathol Exp Neurol. Aug. 2005;64(8):706-15.
Deshmane et al., Monocyte chemoattractant protein-1 (MCP-1): an overview. J Interferon Cytokine Res. Jun. 2009;29(6):313-26.

(56) References Cited

OTHER PUBLICATIONS

Iellem et al., Unique chemotactic response profile and specific expression of chemokine receptors CCR4 and CCR8 by CD4 (+)CD25(+) regulatory T cells. J Exp Med. Sep. 17, 2001;194(6):847-53.
Kim et al., Injectable, spontaneously assembling, inorganic scaffolds modulate immune cells in vivo and increase vaccine efficacy. Nat Biotechnol. Jan. 2015;33(1):64-72.
Patterson et al., Differential binding of chemokines to macrophages and neutrophils in the human inflamed synovium. Arthritis Res. 2002;4(3):209-14.
Weeks et al., The effects of chemokine, adhesion and extracellular matrix molecules on binding of mesenchymal stromal cells to poly(l-lactic acid). Cytotherapy. Oct. 2012;14(9):1080-8.
International Search Report for Application No. PCT/US2016/026617, dated Jul. 11, 2016. 3 pages.
International Preliminary Report on Patentability for Application No. PCT/US2016/026617, dated Oct. 19, 2017. 13 pages.
Anderson et al., Crosslinking CD3 with CD2 using sepharose-immobilized antibodies enhances T lymphocyte proliferation. Cell Immunol. Sep. 1988;115(2):246-56.
Andersson et al., HSP70 promoter-driven activation of gene expression for immunotherapy using gold nanorods and near infrared light. Vaccines (Basel). Mar. 25, 2014;2(2):216-27.
Baroja et al., The anti-T cell monoclonal antibody 93 (anti-CD28) provides a helper signal and bypasses the need for accessory cells in T cell activation with immobilized anti-CD3 and mitogens. Cell Immunol. Apr. 15, 1989;120(1):205-17.
Bhardwaj et al., TLR Agonists: Are They Good Adjuvants? Cancer J. 2010;16(4):382-391.
Bierer et al., T cell receptors: adhesion and signaling. Adv Cancer Res. 1991;56:49-76.
Brodie et al., In vivo migration and function of transferred HIV-1-specific cytotoxic T cells. Nat Med. Jan. 1999;5(1):34-41.
Casanova et al., Human Mannose-binding Lectin in Immunity: Friend, Foe, or Both?. J Exp Med. 2004;199(10):1295-1299.
Chao et al., Morphological control on SBA-15 mesoporous silicas via a slow self-assembling rate. J Mater Sci. 2009;44:6453-62.
Che et al., Synthesis and characteriiation of chiral mesoporous silica. Nature. May 20, 2004;429(6989):281-4.
Chen et al., Enhanced humoral and cell-mediated immune responses generated by cationic polymer-coated PLA microspheres with adsorbed HBsAg. Mol Pharm. Jun. 2, 2014;11(6):1772-84.
Chen et al., Morphological control of mesoporous silica SBA-15 synthesized at low temperature without additives. J Porous Mater. 2011;18:211-6.
Chen et al., Quantitative proteomic profiling of pancreatic cancer juice. Proteomics. Jul. 2006;6(13):3871-9.
Cheung et al., Engineered Materials for Cancer Immunotherapy. Nano Today. Aug. 1, 2015;10(4):511-531.
Cheung et al., Scaffolds that mimic antigen-presenting cells enable ex vivo expansion of primary T cells. Nat Biotechnol. Feb. 2018;36(2):160-169.
Choi et al., Facile synthesis of high quality mesoporous SBA-15 with enhanced control of the porous network connectivity and wall thickness. Cherri Commun (Camb). Jun. 21, 2003;(12):1340-1.
Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.
Damle et al., Stimulation via the CD3 and CD28 molecules induces responsiveness to IL-4 in CD4+CD29+CD45R− memory T lymphocytes. J Immunol. Sep. 15, 1989;143(6):1761-7.
Del Chiaro et al., Early detection and prevention of pancreatic cancer: is it really possible today? World J Gastroenterol. Sep. 14, 2014;20(34):12118-31.
Dengler et al., Mesoporous silica-supported lipid bilayers (protocells) for DNA cargo delivery to the spinal cord. J Control Release. Jun. 10, 2013;168(2):209-24.

Drury et al., Hydrogels for tissue engineering: scaffold design variables and applications. Biomaterials. Nov. 2003;24(24):4337-51.
Dudley et al., CD8+ enriched "young" tumor infiltrating lymphocytes can mediate regression of metastatic melanoma. Clin Cancer Res. Dec. 15, 2010;16(24):6122-31.
Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.
Eggermont et al., Towards efficient cancer immunotherapy: advances in developing artificial antigen-presenting cells. Trends Biotechnol. Sep. 2014;32(9):456-65.
Fadel et al., A carbon nanotube-polymer composite for T-cell therapy. Nat Nanotechnol. Aug. 2014;9(8):639-47.
Fadel et al., Enhanced cellular activation with single walled carbon nanotube bundles presenting antibody stimuli. Nano Lett. Jul. 2008;8(7):2070-6.
Fesnak et al., Engineered T cells: the promise and challenges of cancer immunotherapy. Nat Rev Cancer. Aug. 23, 2016;16(9):566-81.
Gao et al., Immune cell recruitment and cell-based system for cancer therapy. Pharm Res. Apr. 2008;25(4):752-68.
Garlie et al., T cells coactivated with immobilized anti-CD3 and anti-CD28 as potential immunotherapy for cancer. J Immunother. Jul. 1999;22(4):336-45.
Gimmi et al., B-cell surface antigen B7 provides a costimulatory signal that induces T cells to proliferate and secrete interleukin 2. Proc Natl Acad Sci U S A. Aug. 1, 1991;88(15):6575-9.
Grabowska et al., Systemic in vivo delivery of siRNA to tumours using combination of polyethyleneimine and transferrin-polyethyleneimine conjugates. Biomater Sci. Nov. 2015;3(11):1439-48.
Han et al., Synthesis of rod-like mesoporous silica using mixed surfactants of cetyltrimethylammonium bromide and cetyltrimethylammonium chloride as templates. Materials Letters. 2003;57:4520-4.
Harding et al., CD28-mediated signalling co-stimulates murine T cells and prevents induction of anergy in T-cell clones. Nature. Apr. 16, 1992;356(6370):607-9.
Hasan et al., Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.
Haso et al., Anti-CD22-chimeric antigen receptors targeting B-cell precursor acute lymphoblastic leukemia. Blood. Feb. 14, 2013;121(7):1165-74.
Hollyman et al., Manufacturing validation of biologically functional T cells targeted to CD19 antigen for autologous adoptive cell therapy. J Immunother. Feb.-Mar. 2009;32(2):169-80.
Huppa et al., T-cell-antigen recognition and the immunological synapse. Nat Rev Immunol. Dec. 2003;3(12):973-83.
Jiang, Application of polymers in nucleic acid delivery. Thesis in partial fulfillment of the requirements for the Doctor of Philosophy degree in Pharmacy in the Graduate College of the University of Iowa. 138 pages, Dec. 2011.
Johansson, Controlling the Pore Size and Morphology of Mesoporous Silica. Linkoping Studies in Science and Technology Licentiate Thesis No. 1451, 53 pages, (2010).
June et al., Adoptive cellular therapy: a race to the finish line. Sci Transl Med. Mar. 25, 2015;7(280):280ps7.
June et al., The B7 and CD28 receptor families. Immunol Today. Jul. 1994;15(7):321-31.
Kosuge et al., Morphological Control of Rod- and Fiberlike SBA-15 Type Mesoporous Silica Using Water-Soluble Sodium Silicate. Chem Mater. 2004;16:899-905.
Lacy et al., Cytokine release from innate immune cells: association with diverse membrane trafficking pathways. Blood. 2011;118(1):9-18.
Lee et al., The immunological synapse balances T cell receptor signaling and degradation. Science. Nov. 14, 2003;302(5648):1218-22.

(56) References Cited

OTHER PUBLICATIONS

Levine et al., Effects of CD28 costimulation on long-term proliferation of CD4+ T cells in the absence of exogenous feeder cells. J Immunol. Dec. 15, 1997;159(12):5921-30.
Li et al., The effect of surface modification of mesoporous silica micro-rod scaffold on immune cell activation and infiltration. Biomaterials. Mar. 2016;83:249-56.
Liao et al., Synthesis of mesoporous silica nanopartide-encapsulated alginate microparticles for sustained release and targeting therapy. J Biomed Mater Res B Appl Biomater. Feb. 2014;102(2):293-302.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Liu et al., Fecal markers, intestinal inflammation and inflammatory enteritis. Clinical Journal of Digestive Disease. 2003;15(6):275-7.
Liu et al., Porous nanoparticle supported lipid bilayers (protocells) as delivery vehicles. J Am Chem Soc. Feb. 4, 2009;131(4):1354-5.
Mandal et al., Polymer-based synthetic dendritic cells for tailoring robust and multifunctional T cell responses. ACS Chem Biol. Feb. 20, 2015;10(2):485-92.
Mangsbo et al., Enhanced tumor eradication by combining CTLA-4 or PD-1 blockade with CpG therapy. J Immunother. Apr. 2010;33(3):225-35.
Maus et al., Ex vivo expansion of polyclonal and antigen-specific cytotoxic T lymphocytes by artificial APCs expressing ligands for the T-cell receptor, CD28 and 4-1BB. Nat Biotechnol. Feb. 2002;20(2):143-8.
Melief et al., T-cell immunotherapy of tumors by adoptive transfer of cytotoxic T lymphocytes and by vaccination with minimal essential epitopes. Immunol Rev. Jun. 1995;145:167-77.
Meng et al., Use of a lipid-coated mesoporous silica nanoparlicle platform for synergistic gemcitabine and paclitaxel delivery to human pancreatic cancer in mice. ACS Nano. 2015;9(4):3540-57.
Meyer et al., Biodegradable nanoellipsoidal artificial antigen presenting cells for antigen specific T-cell activation. Small. Apr. 2015;11(13):1519-25.
Millar et al., Prediction of local recurrence, distant metastases, and death after breast-conserving therapy in early-stage invasive breast cancer using a five-biomarker panel. J Clin Oncol. Oct. 1, 2009;27(28):4701-8.
Milone et al., Powered and controlled T-cell production. Nat Biomed Eng. Mar. 2018;2(3):148-150.
Mu et al., Identification and characterization of a mannose-binding lectin from Nile tilapia (*Oreochromis niloticus*). Fish Shellfish Immunol. 2017;67:244-253.
NCBI, MeSH. Nivolumab. Retrieved online at https://www.ncbi.nlm.nih/gov/mesh/?term=nivolumab. 3 pages, (2010).
Perica et al., Enrichment and Expansion with Nanoscale Artificial Antigen Presenting Cells for Adoptive Immunotherapy. ACS Nano. Jul. 28, 2015;9(7):6861-71.
Qiao et al., Synthesis and Bio-adsorptive Properties of Large-Pore Periodic Mesoporous Organosilica Rods. Chem Mater. 2005;17:6172-6.
Qin et al., CD22-Targeted Chimeric Antigen Receptor (CAR) T Cells Containing the 4-1BB Costimulatory Domain Demonstrate Enhanced Persistence and Superior Efficacy Against B-Cell Precursor Acute Lymphoblastic Leukemia (ALL) Compared to Those Containing CD28. Blood. 2013;122:1431.
Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.
Riddell et al., Principles for adoptive T cell therapy of human viral diseases. Annu Rev Immunol. 1995;13:545-86.
Riddell et al., Restoration of viral immunity in immunodeficient humans by the adoptive transfer of T cell clones. Science. Jul. 10, 1992;257(5067):238-41.
Riddell et al., The use of anti-CD3 and anti-CD28 monoclonal antibodies to clone and expand human antigen-specific T cells. J Immunol Methods. Apr. 17, 1990;128(2):189-201.
Rosenberg et al., Adoptive cell transfer as personalized immunotherapy for human cancer. Science. Apr. 3, 2015;348(6230):62-8.
Rosenberg et al., Durable complete responses in heavily pretreated patients with metastatic melanoma using T-cell transfer immunotherapy. Clin Cancer Res. Jul. 1, 2011;17(13):4550-7.
Rubbi et al., Evidence of surface antigen detachment during incubation of cells with immunomagnetic beads. J Immunol Methods. Dec. 3, 1993;166(2):233-41.
Schwartz, A cell culture model for T lymphocyte clonal anergy. Science. Jun. 15, 1990;248(4961):1349-56.
Shibuya et al., Anti-CD3/anti-CD28 bead stimulation overcomes CD3 unresponsiveness in patients with head and heck squamous cell carcinoma. Arch Otolaryngol Head Neck Surg. Apr. 2000;126(4):473-9.
Singh et al., Hydrogels and scaffolds for immunomodulation. Adv Mater. Oct. 2014;26(38):6530-41.
Springer et al., The lymphocyte function-associated LFA-1, CD2, and LFA-3 molecules: cell adhesion receptors of the immune system. Annu Rev Immunol. 1987;5:223-52.
Stanley et al., Transjugular intrahepatic portosystemic shunt as a treatment for protein-losing enteropathy caused by portal hypertension. Gastroenterology. Dec. 1996;111(6):1679-82.
Steenblock et al., A comprehensive platform for ex vivo T-cell expansion based on biodegradable polymeric artificial antigen-presenting cells. Mol Ther. Apr. 2008;16(4):765-72.
Steenblock et al., An artificial antigen-presenting cell with paracrine delivery of IL-2 impacts the magnitude and direction of the T cell response. J Biol Chem. Oct. 7, 2011;286(40):34883-92.
Stephen et al., Biopolymer implants enhance the efficacy of adoptive T-cell therapy. Nat Biotechnol. Jan. 2015;33(1):97-101.
Sunshine et al., Nanoengineering approaches to the design of artificial antigen-presenting cells. Nanomedicine. 2013;8(7):1173-89.
Sunshine et al., Particle shape dependence of CD8+ T cell activation by artificial antigen presenting cells. Biomaterials. Jan. 2014;35(1):269-277.
Takamura et al., Regulatory role of lymphoid chemokine CCL19 and CCL21 in the control of allergic rhinitis. J Immunol. 2007;179(9):5897-5906.
Thielemann et al., Pore structure and surface area of silica SBA-15: influence of washing and scale-up. Beilstein J Nanotechnol. 2011;2:110-8.
Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves in Vivo Expansion and Persistence of CAR-T Cells and Clinical Outcomes. Blood. 2015;126:184.
Turtle et al., CD19 CAR-T cells of defined CD4+:CD8+ composition in adult B cell ALL patients. J Clin Invest. Jun. 1, 2016;126(6):2123-38.
Wang et al., Mouse CD229 Ligation Co-stimulates T Cell Activation. The Journal of Immunology. May 2012;188(suppl 1):176.7.
Yee et al., Melanocyte destruction after antigen-specific immunotherapy of melanoma: direct evidence of t cell-mediated vitiligo. J Exp Med. Dec. 4, 2000;192(11):1637-44.
Yu, Designed synthesis of mono-dispersed silica-based nanostructures and their applications in drug/gene delivery. A thesis submitted for the degree of Doctor of Philosophy at the University of Queensland in 2014, 196 pages.
Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.
U.S. Appl. No. 15/434,781, filed Feb. 16, 2017, 2017-0246281, Allowed.
U.S. Appl. No. 13/386,950, filed Jan. 25, 2012, U.S. Pat. No. 8,728,456, Issued.

(56) References Cited

OTHER PUBLICATIONS

U.S. Appl. No. 14/185,494, filed Feb. 20, 2014, U.S. Pat. No. 9,381,235, Issued.
U.S. Appl. No. 15/147,442, filed May 5, 2016, U.S. Pat. No. 10,080,789, Issued.
U.S. Appl. No. 16/121,988, filed Sep. 5, 2018, 2019-0183992, Published.
U.S. Appl. No. 16/316,778, filed Jan. 10, 2019, 2019-0292517, Published.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,207, filed Apr. 21, 2016, U.S. Pat. No. 10,137,184, Issued.
U.S. Appl. No. 16/170,313, filed Oct. 25, 2018, 2019-0125849, Published.
U.S. Appl. No. 13/877,572, filed Nov. 19, 2013, 2014-0079752, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Published.
U.S. Appl. No. 16/033,025, filed Jul. 11, 2018, 2019-0076373, Published.
U.S. Appl. No. 14/394,552, filed Oct. 15, 2014, U.S. Pat. No. 9,937,249, Issued.
U.S. Appl. No. 15/935,392, filed Mar. 26, 2018, 2018-0344821, Published.
U.S. Appl. No. 15/303,985, filed Oct. 13, 2016, U.S. Pat. No. 10,682,400, Issued.
U.S. Appl. No. 16/877,274, filed May 18, 2020, Pending.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, U.S. Pat. No. 10,568,949, Issued.
U.S. Appl. No. 15/563,878, filed Oct. 2, 2017, 2018-0117171, Abandoned.
U.S. Appl. No. 15/546,852, filed Jul. 27, 2017, 2018-0021253, Published.
U.S. Appl. No. 16/075,937, filed Aug. 6, 2018, 2019-0060525, Published.

* cited by examiner

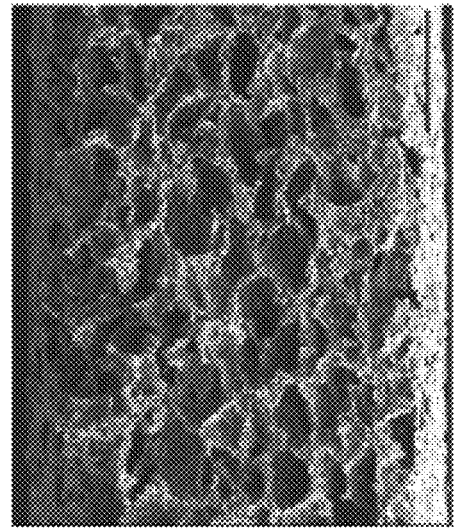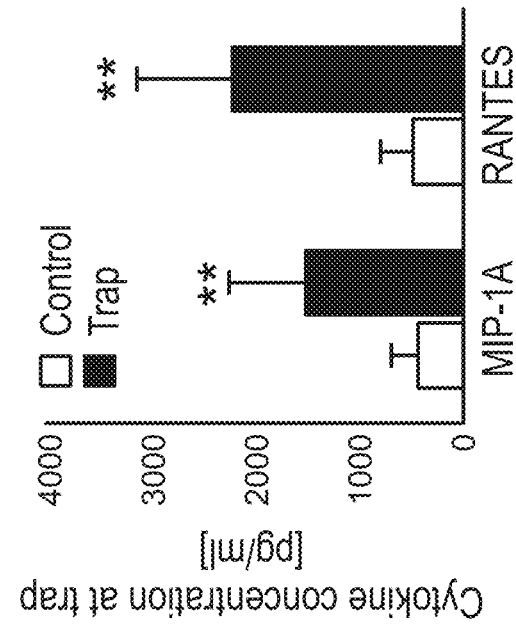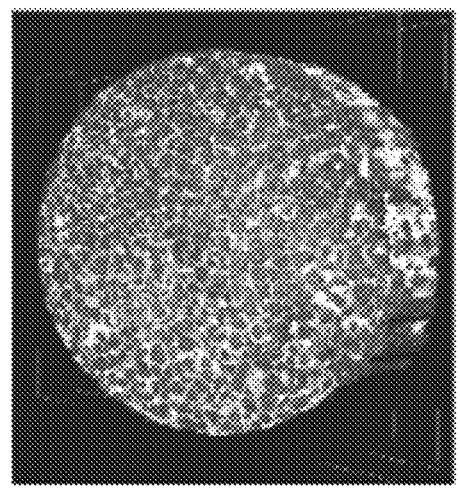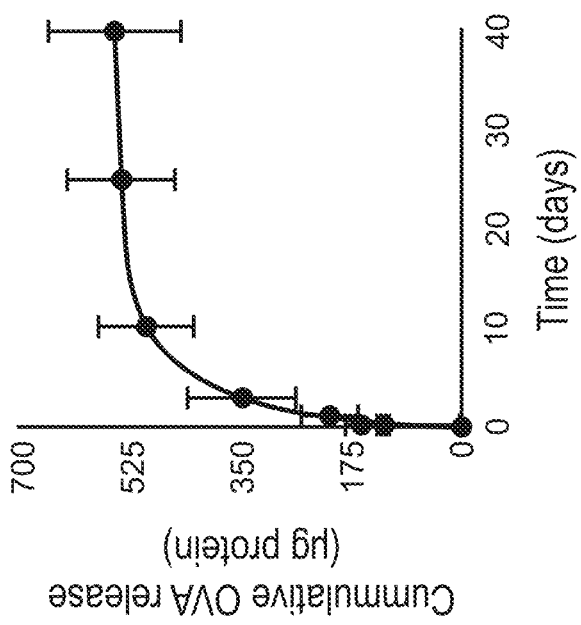

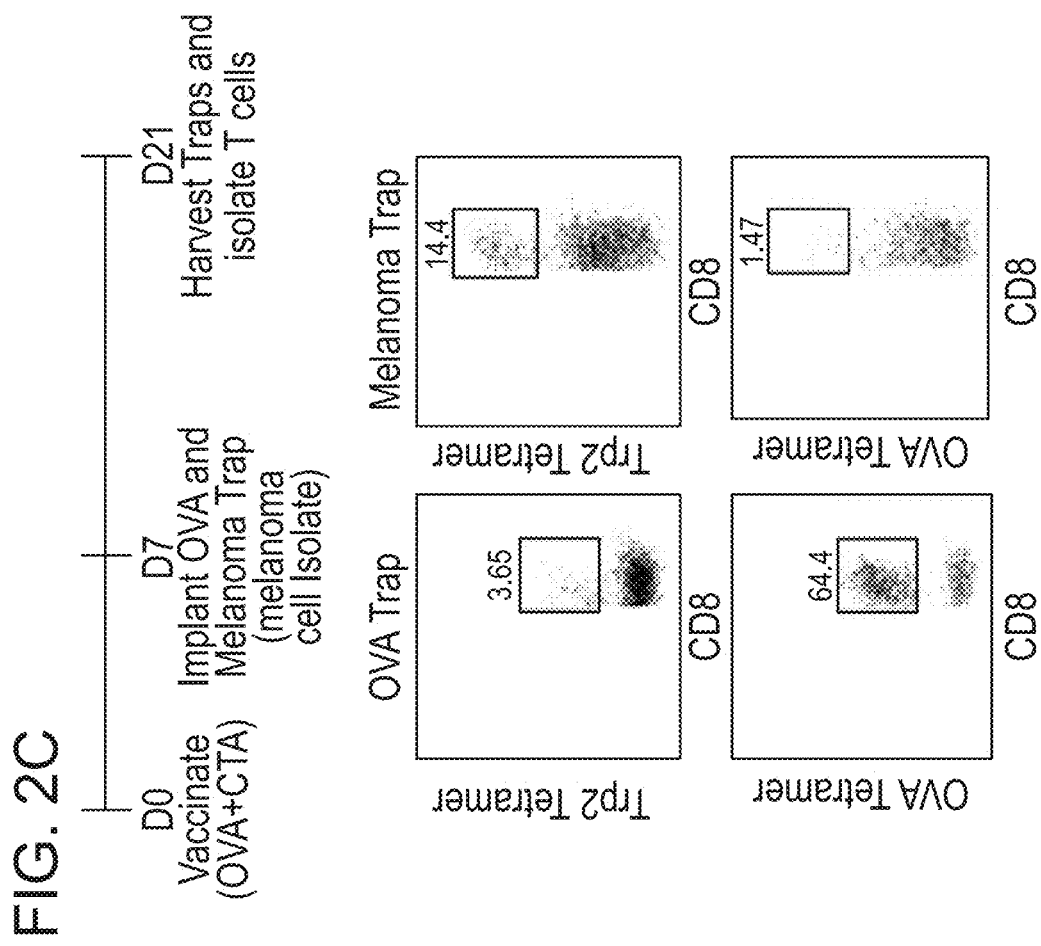

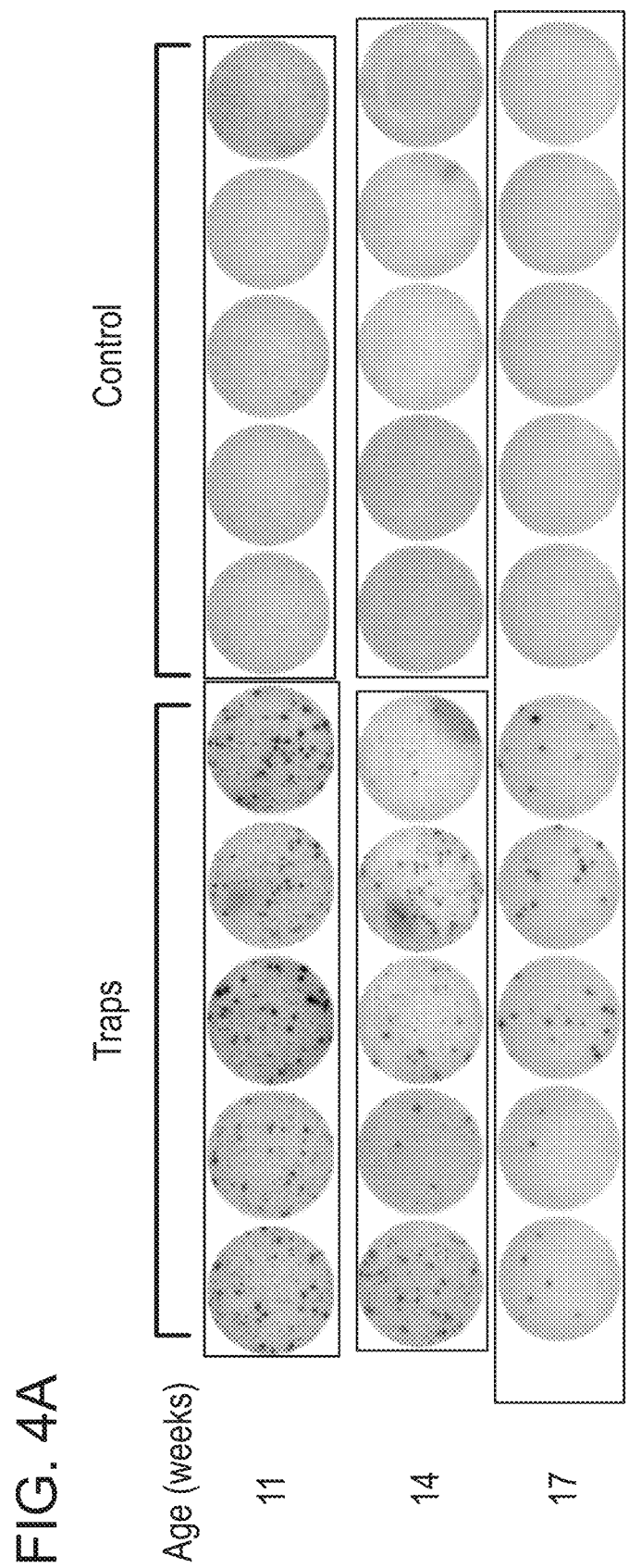

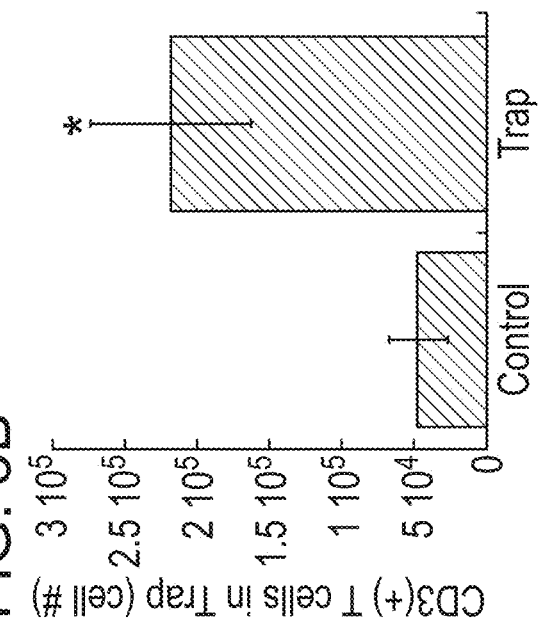
FIG. 5A
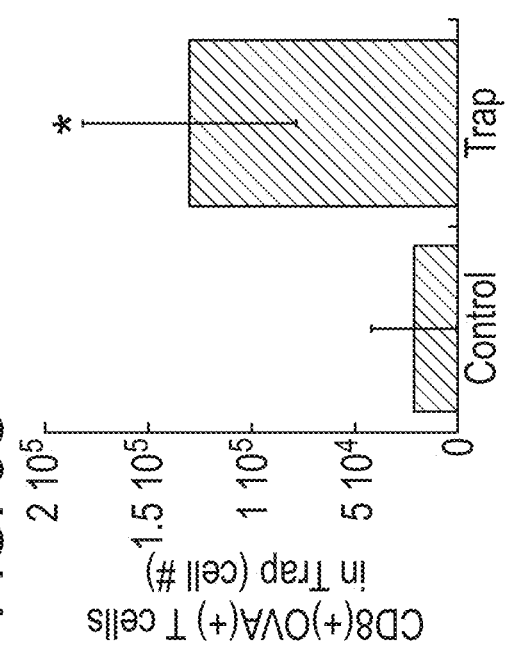
FIG. 5B
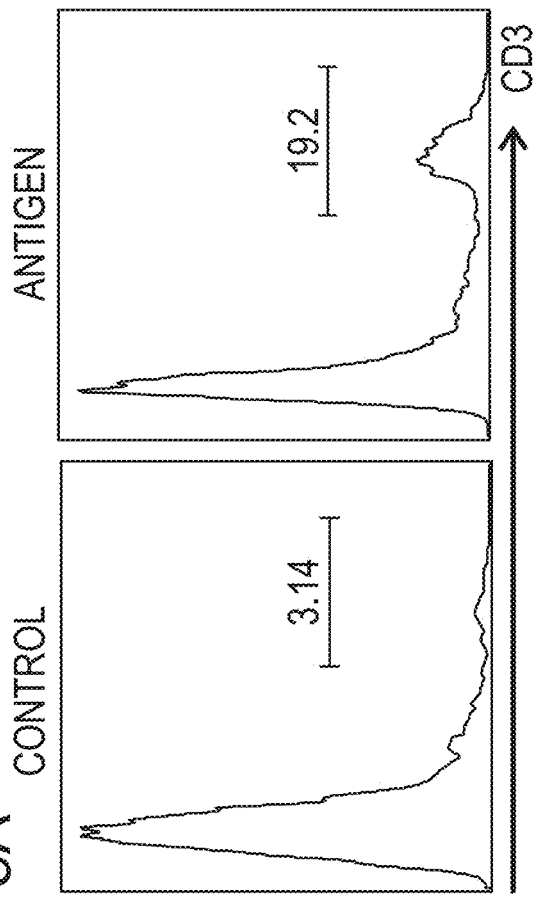
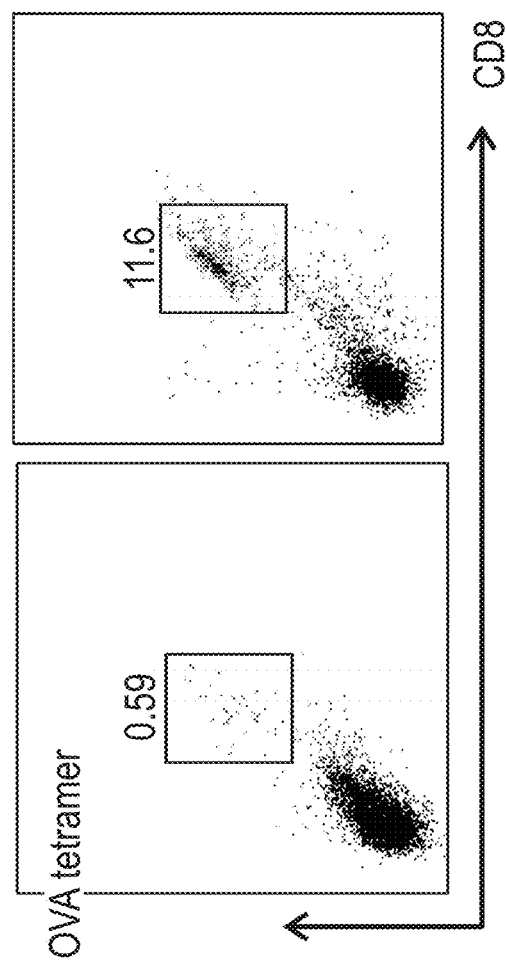
FIG. 5C

IMMUNE CELL TRAPPING DEVICES AND METHODS FOR MAKING AND USING THE SAME

RELATED APPLICATIONS

This application is a 35 U.S.C. § 371 national stage filing of International Application No. PCT/US2016/026617, filed on Apr. 8, 2016, which in turn claims priority to U.S. Provisional Application Ser. No. 62/146,205, filed on Apr. 10, 2015. The entire contents of this each of the foregoing applications are incorporated herein by reference.

BACKGROUND OF THE INVENTION

Cells of the immune system play a central role in distinguishing between foreign and self-antigens in the context of autoimmunity and neoplastic diseases. The process of thymic (central) tolerance provides a basis for the immune cells to confer homeostatic balance between the two disease states. At one end, high-affinity self-antigen-specific T cells are eliminated from the system, leading to the prevention of autoimmunity. At the other end, cells that fail to recognize self-antigens entirely are also eliminated and this ensures that tumor cells are held in check. The result of this complex process is that only the T cells that recognize self-antigens with intermediate affinity are spared and allowed to propagate. This development of peripheral tolerance is central to keeping potentially autoreactive lymphocytes in check because recirculating lymphocytes exposed to tissue antigens under non-inflammatory conditions are normally in a tolerant, anergic state. However, in the presence of danger stimuli, such as those elicited by infection and tissue damage, the balance between tolerance and autoimmunity can be broken. Conversely, if self-reactive cells are depleted from the immune repertoire, then the immune system may fail to recognize tumors expressing altered levels or patterns of self antigens.

It is now recognized that many autoimmune diseases are mediated by auto-reactive T cell responses. For example, in the context of type-1 diabetes, auto-reactive T cells have been implicated in the destruction of pancreatic beta cells. Likewise, pathophysiology of multiple sclerosis is often characterized by auto-reactive T-cell mediated targeting and apoptosis of neuronal cells. However, proper diagnosis and identification of autoimmune disease is fraught with difficulty because they often require performing many laboratory tests (usually, involving complete blood count, comprehensive metabolic panel, acute phase reactants, immunologic studies, serologies, flow cytometry, cytokine analysis, and HLA typing). These tests are cumbersome and expensive to administer.

At the cellular level, diagnosing auto-immune disorders based on immune-cell karyotyping is similarly problematic due to the lack of accessibility of functional T cells from the site of tissue destruction. In many diseases, auto-reactive cells occur at such low frequencies (1:100,000 cells) that detection of specific immune cells is technically challenging. Additionally, in many instances, the population of auto-reactive cells are not necessarily disease specific. Even when the disease-specific T-cells are isolated, they have limited use in diagnostic or therapeutic applications because they cannot be frozen or cultured without affecting their functional capacities.

Similarly, in the context of cancer, existing therapeutic strategies generally involve adoptive transfer of antigen-specific T cells that are extracted from the host. In such instances, tumor infiltrating leukocytes (TILs) are extracted from tumor biopsies or peripheral blood, manipulated to add antigen specificity or homing capacity, expanded ex vivo, and injected into patients to target tumor cells. However, the quantities of these cells in the blood or in diseased sites are often of low frequency and lack ideal functionality.

There is, therefore, an unmet need for compositions and methods that allow isolation of immune cells, which can be analyzed for diagnosing autoimmune disorders and cancers, and for the therapy of human diseases, such as autoimmune disorders, cancers and infectious diseases. Embodiments of the instant invention, which are described in detail below, address these needs.

SUMMARY OF THE INVENTION

The present invention provides a solution to the problem of identifying and collecting rare cells or cells with occur at low frequency in the body. Particular embodiments described herein relate to collection devices, cell trapping devices, which are useful in the collection of such cells. The devices include a scaffold composition which incorporates or is coated with a plurality of antigens and, optionally, recruiting agents, allowing the device to attract, adhere to, and capture or sequester targeted cells, such as immune cells. The device executes these functions by a variety of methods that include direct or indirect interaction with the antigens, recruiting agents, or other molecules present therein. Depending on the application for which the device is used, the device regulates capture and survival of the targeted cells through the physical or chemical characteristics of the scaffold itself. For example, the scaffold composition is differentially permeable, allowing cell passage only in certain physical areas of the scaffold. The permeability of the scaffold composition is regulated, for example, by selecting or engineering a material for greater or smaller pore size, density, polymer cross-linking, stiffness, toughness, ductility, or visco-elascticity. The scaffold composition may contain physical channels or paths through which targeted cells interact with the device and/or move into a specific compartment or region of the device. To facilitate the compartmentalization, the scaffold composition is optionally organized into compartments or layers, each with a different permeability, so that cells are sorted or filtered to allow access to only a certain sub-population of cells. Sequestration of target cell populations in the device may also be regulated by the degradation, de- or re-hydration, oxygenation, chemical or pH alteration, or ongoing self-assembly of the scaffold composition. Following their capture, the targeted cells, e g, immune cells, may be allowed to grow or expand within the device with the help of stimulatory molecules, cytokines, and other co-factors present in the device. In some embodiments, non-targeted cells which have otherwise infiltrated the device may be rejected or removed using negative selection agents.

The cells that are trapped within the devices of the invention are primarily immune cells. In certain embodiments, the invention relates to T-cell traps. In other embodiments, the invention relates to B-cell traps. Yet in other embodiments, the invention relates to a combination of traps, e.g., a combination of T-cell traps and B-cell traps. The traps described herein may also be configured to trap antigen presenting cells (APCs), such as, for example, autoreactive APCs. Examples of auto-reactive APCs that may be trapped include, for example, dendritic cells (DCs), macrophages, or a combination of thereof. In other embodiments, a plurality of traps may be employed, e.g., traps which are configured for trapping both lymphocytes and APCs. For example, antigen-specific cells or disease specific-cells such as T cells, dendritic cells (DCs), or macrophages may be trapped, either separately or together, for analyses, reprogramming or depletion. The trapped immune cells, e.g., lymphocytes and APCs, are optionally harvested and analyzed to identify and characterize targets for disease diagnosis or immunotherapy. The trapped cells may also be reprogrammed or expanded for developing compositions or formulations that are to be used in therapy.

Accordingly, in one aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device. The antigens may be absorbed onto the polymer scaffold or encapsulated by the polymer scaffold.

In another aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device by binding to the plurality of immune cells.

In another aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device and the device does not contain an agent that kills or eliminates immune cells.

In yet another aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device and the device further comprises an immune cell recruiting agent. The immune cell recruiting agent may be, for example, a T-cell recruiting agent, a dendritic cell recruiting agent, or a macrophage recruiting agent, or a combination thereof. Particularly, the immune cell recruiting agent may be a natural killer (NK) cell recruiting agent, a CD3+ T-cell recruiting agent, a CD4+ T-cell recruiting agent, a CD8+ T cell recruiting agent, a CD8+ T cell recruiting agent, a regulatory T-cell (Treg) recruiting agent, or a combination thereof. In related aspects, the immune cell recruiting agent may be a growth factor, a cytokine, an interleukin, an adhesion signaling molecule, an integrin signaling molecule, an interferon, a lymphokine, or a chemokine, or a fragment thereof, or a combination thereof. Particularly, the immune cell recruiting agent may be an interleukin which is selected from the group consisting of IL-1, IL-2, IL-4, IL-5, IL-10 IL-12 and IL-17.

In another aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device and the device comprises an agent which enhances infiltration of the immune cells into the device.

In another aspect, the present invention provides an immune-cell trapping device, comprising a physiologically-compatible porous polymer scaffold, and a plurality of purified cancer antigens, wherein the plurality of cancer antigens attract and trap a plurality of immune cells specific to the plurality of cancer antigens in the device. According to this aspect, the cancer antigen may be selected from the group consisting of MAGE-1, MAGE-2, MAGE-3, CEA, Tyrosinase, midkin, BAGE, CASP-8, β-catenin, β-catenin, γ-catenin, CA-125, CDK-1, CDK4, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf 112, SART1, SART2, SART3, BRAP, RTN4, GLEA2, TNKS2, KIAA0376, ING4, HSPH1, Cl3orf24, RBPSUH, C6orf153, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Glil, Cav-1, cathepsin B, CD74, E-cadherin, EphA2/Eck, Fra-1/Fosl 1, GAGE-1, Ganglioside/GD2, GnT-V, β1,6-N, Ki67, Ku70/80, PROX1, PSCA, SOX10, SOX11, Survivin, UPAR, WT-1, Dipeptidyl peptidase IV (DPPIV), adenosine deaminase-binding protein (AD Abp), cyclophilin b, Colorectal associated antigen (CRC)-C017-1A/GA733, T-cell receptor/CD3-zeta chain, GAGE-family of tumor antigens, RAGE, LAGE-I, NAG, GnT-V, RCAS1, α-fetoprotein, p120ctn, Pmel117, PRAME, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, PlA, Connexin 37, Ig-idiotype, p15, GM2, GD2 gangliosides, Smad family of tumor antigens, lmp-1, EBV-encoded nuclear antigen (EBNA)-I, UL16-binding protein-like transcript 1 (Multi), RAE-1 proteins, H60, MICA, MICB, and c-erbB-2, or an immunogenic peptide thereof, and combinations thereof.

In another aspect, the present invention provides an immune-cell trapping device, comprising a physiologically-compatible porous polymer scaffold, and a plurality of purified non-self antigens, wherein the plurality of non-self antigens attract and trap a plurality of immune cells specific to the plurality of non-self antigens in the device. According to this aspect, the non-self antigens may be pathogenic antigens derived from a pathogen selected from the group consisting of a virus, a bacteria, a protozoan, a parasite, and a fungus. Further according to this aspect, the pathogen may be selected from the group consisting of *Mycobacterium bovis*, Human Papillomavirus (HPV), Human immunodeficiency virus, a pox virus, smallpox virus, ebola virus, marburg virus, dengue fever virus, influenza virus, parainfluenza virus, respiratory syncytial virus, rubeola virus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, hepatitis E virus, SARS CoV, MERS CoV, Enterovirus, *Borrelia* species, *Bacillus anthracis, Borrelia burgdorferi, Bordetella pertussis, Camphylobacter jejuni, Chlamydia* species, *Chlamydial psittaci, Chlamydial trachomatis, Clostridium* species, *Clostridium tetani, Clostridium botulinum, Clostridium perfringens, Corynebacterium diphtheriae, Coxiella* species, an *Enterococcus* species, *Erlichia* species, *Escherichia coli, Francisella tularensis, Haemophilus* species, *Haemophilus influenzae, Haemophilus parainfluenzae, Lactobacillus* species, a *Legionella* species, *Legionella pneumophila, Leptospirosis interrogans, Listeria* species, *Listeria monocytogenes, Mycobacterium* species, *Mycobacterium tuberculosis, Mycobacterium leprae, Mycoplasma* species, *Mycoplasma pneumoniae, Neisseria* species, *Neisseria meningitidis,*

*Neisseria gonorrhoeae, Pneumococcus* species, *Pseudomonas* species, *Pseudomonas aeruginosa, Salmonella* species, *Salmonella typhi, Salmonella enterica, Rickettsia* species, *Rickettsia ricketsii, Rickettsia typhi, Shigella* species, *Staphylococcus* species, *Staphylococcus aureus, Streptococcus* species, *Streptococccus pnuemoniae, Streptococcus pyrogenes, Streptococcus mutans, Treponema* species, *Treponema pallidum*, a *Vibrio* species, *Vibrio cholerae, Yersinia pestis*, Methicillin-resistant *Staphylococcus aureus, Aspergillus* species, *Aspergillus, funigatus, Aspergillus flavus, Aspergillus calvatus, Candida* species, *Candida albicans, Candida tropicalis, Cryptococcus* species, *Cryptococcus neoformans, Entamoeba histolytica, Histoplasma capsulatum, Leishmania* speceis, *Nocardia asteroides, Plasmodium falciparum, Stachybotrys chartarum, Toxoplasma gondii, Trichomonas vaginalis, Toxoplasma* species, *Trypanosoma brucei, Schistosoma mansoni, Fusarium* species, *Trichophyton* species, *Plasmodium* species, *Toxoplasma* species, *Entamoeba* species, *Babesia* species, *Trypanosoma* species, *Leshmania* species, *Pneumocystis* species, *Pneumocystis jirovecii, Trichomonas* species, *Giardia* species, *Schisostoma* species, *Cryptosporidium* species, *Plasmodium* species, *Entamoeba* species, *Naegleria* species, *Acanthamoeba* species, *Balamuthia* species, *Toxoplasma* species, *Giardia* species, *Trichomonas* species, *Leishmania* species, and *Trypanosoma* species.

In another aspect, the present invention provides an immune-cell trapping device, comprising a physiologically-compatible porous polymer scaffold, and a plurality of purified self antigens, wherein the plurality of self antigens attract and trap a plurality of immune cells specific to the plurality of self antigens in the device. According to this aspect, the self antigens may be derived from a lysate of a cell to which an autoimmune response is directed. Further according to this aspect, the antigen may be a pancreatic beta cell antigen, a neuronal cell antigen, a bone or joint associated autoimmune disease associated antigen, or a gastrointestinal-disease associated antigen. Still further according to this aspect, the antigen may be an antigen associated with type I diabetes; an antigen associated with multiple sclerosis; an antigen associated with rheumatoid arthritis; an antigen associated with inflammatory bowel disease; or an antigen associated with Crohn's disease.

In another aspect, the present invention provides an immune-cell trapping device, comprising a physiologically-compatible porous polymer scaffold, a plurality of purified antigens and another agent which is an RGD peptide, a CpG oligonucleotide or a granulocyte-macrophage colony-stimulating factor (GM-CSF) cytokine, or a fragment thereof or a combination thereof, wherein the plurality of antigens attract and trap a plurality of immune cells specific to the plurality of antigens in the device. In an alternate aspect, the present invention provides an immune-cell trapping device, comprising a physiologically-compatible porous polymer scaffold and a plurality of purified antigens, but the device does not contain an RGD peptide, a CpG oligonucleotide or a granulocyte-macrophage colony-stimulating factor (GM-CSF) cytokine or a fragment thereof or a combination thereof.

In another aspect, the present invention provides an immune-cell trapping device which preferentially attracts T-cells compared to other immune cells. According to this aspect, the device comprises a physiologically-compatible porous polymer scaffold and a plurality of purified antigens, wherein the plurality of antigens attract and trap a plurality of immune cells specific to the plurality of antigens in the device and the device further comprises a chemokine selected from the group consisting of CCL1, CCL2 (MCP-1), CCL-3, CCL-4, CCL-5 (RANTES), CCL-17, CCL-22, CXCL12 and XCL1, or a fragment thereof, or a combination thereof. Still further according to this aspect, the chemokine may be selected from the group consisting of:

(a) CCL1 (accession numbers for human homolog: NM_002981.2; GI:523498696 and accession numbers for mouse homolog: NM 011329; GI:257153404),
(b) CCL2 (MCP-1)(accession numbers for human homolog: NM_002982.3; GI:56119169 and accession numbers for mouse homolog: NM_011333.3; GI:141803162),
(c) CCL3 (accession numbers for human homolog: NM_002983.2; GI: 121582465 and accession numbers for mouse homolog: NM 011337.2; GI: 126432552),
(d) CCL4 (accession numbers for human homolog: NM 002984.3; GI:748585189 NM 013652.2 and accession numbers for mouse homolog: NM_013652.2; GI:126366031),
(e) CCL5 (RANTES)(accession numbers for human homolog: NM_002985.2; GI: 22538813 and accession numbers for mouse homolog: NM_013653.3; GI: 164698427),
(f) CCL17 (accession numbers for human homolog: NM_002987.2; GI:22538801 and NM_011332.3; accession numbers for mouse homolog: NM_011332.3; GI:225735578),
(g) CCL19 (accession numbers for human homolog: NM_006274.2; GI:22165424 and accession numbers for mouse homolog: NM 011888.2; GI: 10518345),
(h) CCL22 (accession numbers for human homolog: NM_002990.4; GI:300360575 and accession numbers for mouse homolog: NM_009137.2; GI: 154240695),
(i) CXCL12 (accession numbers for human homolog: NM_199168.3; GI: 291045298 and accession numbers for mouse homolog: NM_001277990.1; GI: 489406389), and
(j) XCL1 (accession numbers for human homolog: NM_002995.2; GI:312434026 and accession numbers for mouse homolog: NM 008510.1; GI: 6678711).

In another aspect, the present invention provides an immune-cell trapping device which preferentially attracts dendritic cells (DC) compared to other immune cells. According to this aspect, the device comprises a physiologically-compatible porous polymer scaffold and a plurality of purified antigens, wherein the plurality of antigens attract and trap a plurality of immune cells specific to the plurality of antigens in the device and the device further comprises a chemokine selected from the group consisting of CCL2, CCL3, CCL5, CCL7, CCL8, CCL13, CCL17, and CCL22 or a fragment thereof, or a combination thereof. Still further according to this aspect, the chemokine may be selected from the group consisting of:

(a) CCL2 (accession numbers for human homolog: NM 002982.3; GI:56119169 and accession numbers for mouse homolog: NM 011333.3; GI:141803162),
(b) CCL3 (accession numbers for human homolog: NM_002983.2; GI: 121582465 and accession numbers for mouse homolog: NM_011337.2; GI: 126432552),
(c) CCL5 (Variant 1) (accession numbers for human homolog: NM 002985.2; GI: 22538813 and accession numbers for mouse homolog: NM_013653.3; GI: 164698427),
(d) CCL7 (accession numbers for human homolog: NM_006273.3; GI:428673540 and accession numbers for mouse homolog: NM_013654.3; GI:226958664),
(e) CCL8 (accession numbers for human homolog: NM_005623.2; GI:22538815 and accession numbers for mouse homolog: NM 021443.3; GI:255708468),
(f) CCL13 (accession numbers for human homolog: NM_005408.2; GI:22538799 and accession numbers for mouse homolog: NM_011333.3; GI:141803162), (g) CCL17 (accession numbers for human homolog: NM_002987.2 GI:22538801 and accession numbers for mouse homolog: NM 011332.3; GI:225735578), and (h) CCL22 (accession numbers for human homolog: NM_002990.4; GI:300360575 and accession numbers for mouse homolog: NM_009137.2; GI: 154240695).

In another aspect, the present invention provides an immune-cell trapping device which preferentially attracts both T-cells and dendritic cells (DC) compared to other immune cells. According to this aspect, the device comprises a physiologically-compatible porous polymer scaffold and a plurality of purified antigens, wherein the plurality of antigens attract and trap a plurality of immune cells specific to the plurality of antigens in the device and the device further comprises a chemokine selected from the group consisting of CCL17 and CCL22, or a fragment thereof, or a combination thereof. Still further according to this aspect, the chemokine may be selected from the group consisting of:

(a) CCL17 (accession numbers for human homolog: NM_002987.2 GI:22538801 and accession numbers for mouse homolog: NM 011332.3; GI:225735578), and (b) CCL22 (accession numbers for human homolog: NM_002990.4; GI:300360575 and accession numbers for mouse homolog: NM_009137.2; GI: 154240695).

In yet another aspect, the present invention provides an immune-cell trapping device, comprising a physiologically-compatible porous polymer scaffold, a plurality of purified antigens, and a plurality of adhesion receptors, wherein the plurality of antigens attract and trap a plurality of immune cells specific to the plurality of antigens in the device. According to this aspect, the adhesion receptors may be adhesion receptors for T-cells selected from the group consisting of LFA-1, MAdCAM-1, VCAM-1, CD28 and CTLA-4 or a fragment thereof or a combination thereof. Still further according to this aspect, the adhesion receptor may be selected from the group consisting of:

(a) LFA (accession numbers for human homolog: NM 000211.4; GI:735367774 and accession numbers for mouse homolog: M60778.1; GI:198785), (b) MAdCAM-1 (accession numbers for human homolog: NM 130760.2 GI:109633021 and accession numbers for mouse homolog: D50434.2; GI: 60391311), (c) VCAM-1 (accession numbers for human homolog: NM 001078.3; GI:315434269 and accession numbers for mouse homolog: X67783.1; GI: 298116), (d) CD28 (accession numbers for human homolog: NM 006139.3; GI: 340545506 and accession numbers for mouse homolog: BC064058.1; GI: 39850201), and (e) CTLA-4 (accession numbers for human homolog: NM 005214.4; GI: 339276048 and accession numbers for mouse homolog: U90270.1; GI:4099836).

In another aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device and the device comprises about 10 µg to about 2.0 mg of the antigens.

In another aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device and the device comprises about 0.1 µg to about 400 µg of the antigens per gram of dry weight of the scaffold.

In another aspect, the present invention provides an immune-cell trapping device, comprising a physiologically-compatible porous polymer scaffold, and a plurality of purified antigens, wherein the plurality of antigens attract and trap a plurality of immune cells specific to the plurality of antigens in the device and the device has a porosity of between about 40% to about 90%.

In another aspect, the present invention provides an immune-cell trapping device, comprising a physiologically-compatible porous polymer scaffold having pores having a diameter of about 10 µM to about 500 µM, and a plurality of purified antigens, wherein the plurality of antigens attract and trap a plurality of immune cells specific to the plurality of antigens in the device.

In another aspect, the present invention provides an immune-cell trapping device, comprising a physiologically-compatible porous polymer scaffold having a compound selected from the group consisting of polylactic acid (PLA), polyglycolic acid (PGA), poly(lactide-co-glycolide) (PLGA), alginate or a derivative thereof, gelatin, collagen, fibrin, hyaluronic acid (HA), agarose, a polysaccharide, a polyamino acid, a polypeptide, a polyester, a polyanhydride, a polyphosphazine, a polyvinyl alcohol (PVA), a polyalkylene oxides (PAO), a polyallyl amines)(PAM), a polyacrylate, a modified styrene polymer, a pluronic polyol, a polyoxamer, a polyuronic acid, and a polyvinylpyrrolidone or a co-polymer thereof, or a graft polymer thereof, and a plurality of purified antigens, wherein the plurality of antigens attract and trap a plurality of immune cells specific to the plurality of antigens in the device.

In yet another aspect, the present invention provides a pharmaceutical composition comprising an immune-cell trapping device and a pharmaceutically acceptable carrier, wherein the device comprises a physiologically-compatible porous polymer scaffold, and a plurality of purified antigens, wherein the plurality of antigens attract and trap a plurality of immune cells specific to the plurality of antigens in the device. According this aspect, the pharmaceutical composition may be formulated for intravenous administration, subcutaneous administration, intraperitoneal administration, or intramuscular administration. Still further according to this aspect, the pharmaceutical composition may be formulated for subcutaneous administration as a microneedle patch.

In another aspect, the present invention provides a method of treating a disease in a subject in need thereof, comprising administering an immune-cell trapping device to the subject, wherein the device comprises a physiologically-compatible porous polymer scaffold, and a plurality of purified antigens that are specific for the disease, wherein the plurality of antigens attract and trap a plurality of immune cells specific to the plurality of antigens in the device; collecting a plurality of immune cells trapped in the device; and administering the plurality of immune cells into the subject, thereby treating the disease in the subject. According to this aspect, the immune cells may be collected by explanting the device from the subject. Still further according to this aspect, the therapeutic method may include expanding the plurality of immune cells, thereby generating an expanded population of immune cells that are specific for the disease; and administering the expanded population of immune cells into the subject. The subject to be treated according to this aspect is preferably a human subject. Still further, the method according to this aspect may involve administering the device subcutaneously or intravenously into the subject. Under one embodiment of the therapeutic aspect, the plurality of immune cells are collected about 1 day to about 60 days after the device is administered to the subject.

In a related aspect, the present invention provides a method of treating cancer in a subject in need thereof, comprising administering an immune-cell trapping device to the subject, wherein the device comprises a physiologically-compatible porous polymer scaffold, and a plurality of purified antigens that are specific for the cancer, wherein the plurality of cancer antigens attract and trap a plurality of immune cells specific to the cancer antigens; collecting a plurality of immune cells trapped in the device; and administering the plurality of immune cells into the subject, thereby treating the cancer in the subject. According to this aspect, the method may be used to treat a cancer selected from the group consisting of head and neck cancer, breast cancer, pancreatic cancer, prostate cancer, renal cancer, esophageal cancer, bone cancer, testicular cancer, cervical cancer, gastrointestinal cancer, glioblastoma, leukemia, lymphoma, mantle cell lymphoma, pre-neoplastic lesions in the lung, colon cancer, melanoma, and bladder cancer. The subject to be treated according to this aspect is preferably a human subject.

In yet another related aspect, the present invention provides a method of treating an autoimmune disease in a subject in need thereof, comprising administering an immune-cell trapping device to the subject, wherein the device comprises a physiologically-compatible porous polymer scaffold, and a plurality of purified antigens that are specific for the autoimmune disease, wherein the plurality of antigens specific for the autoimmune disease attract and trap a plurality of immune cells specific to the antigens; collecting a plurality of immune cells trapped in the device; and administering the plurality of immune cells into the subject, thereby treating the autoimmune disease in the subject. According to this aspect, the method may be used to treat an autoimmune disease selected from the group consisting of type I diabetes, multiple sclerosis, rheumatoid arthritis, inflammatory bowel disease, and Crohn's disease. Still according to this aspect, the immune cells that are trapped may include regulatory or suppressor T-cells. The subject to be treated according to this aspect is preferably a human subject.

In yet another related aspect, the present invention provides a method of treating a pathogenic disease in a subject in need thereof, comprising administering an immune-cell trapping device to the subject, wherein the device comprises a physiologically-compatible porous polymer scaffold, and a plurality of purified antigens that are specific for the pathogenic disease, wherein the plurality of antigens attract and trap a plurality of immune cells specific to the antigens specific for the pathogenic disease; collecting a plurality of immune cells trapped in the device; and administering the plurality of immune cells into the subject, thereby treating the pathogenic disease in the subject. According to this aspect, the pathogen is selected from the group consisting of a virus, a bacteria, a protozoan, a parasite, and a fungus. The subject to be treated according to this aspect is preferably a human subject.

In another aspect, the instant invention provides for a method for obtaining immune cells that are specific for an antigen. The method comprises administering an immune-cell trapping device, which comprises a physiologically-compatible porous polymer scaffold, and a plurality of purified antigens, wherein the plurality of antigens attract and trap a plurality of immune cells specific to the plurality of antigens in the device to a subject; and harvesting immune cells trapped in the device, thereby obtaining immune cells specific for the antigen. The device may be explanted from the subject to collect the immune cells. The subject from which the immune cells are to be obtained according to this aspect is preferably a human subject. According to this aspect, the device may be subcutaneously or intravenously administered into the subject. Still according to this aspect, the plurality of immune cells may be collected about 1 day to about 60 days after the device is administered to the subject.

In another aspect, the instant invention provides method for determining whether a subject has an autoimmune disease. The method comprises administering an immune-cell trapping device into a subject, wherein the device comprises a physiologically-compatible porous polymer scaffold, and a plurality of purified antigens that are specific for the autoimmune disease, wherein the plurality of antigens attract and trap a plurality of immune cells specific to the plurality of antigens in the device; collecting immune cells trapped in the device, wherein the immune cells are specific to the autoimmune disease; and determining the number of immune cells specific to the autoimmune disease trapped in the device, thereby determining whether a subject has an autoimmune disease. The device may be explanted from the subject to collect the immune cells. The subject from which the immune cells are to be obtained according to this aspect is preferably a human subject. According to this aspect, the device may be subcutaneously or intravenously administered to the subject. Still according to this aspect, the plurality of immune cells may be collected about 1 day to about 60 days after the device is administered to the subject.

In yet another aspect, the instant invention provides for a method for making an immune-cell trapping device, comprising a physiologically-compatible porous polymer scaffold, and a plurality of purified antigens, wherein the plurality of antigens attract and trap a plurality of immune cells specific to the plurality of antigens in the device. The method comprises incubating plurality of purified antigens with a physiologically compatible polymer to generate a polymer-antigen mixture; freezing, lyophilizing and mixing the polymer-antigen mixture with a porogen; compression molding the mixture to produce a disc; subjecting the disk to a high-pressure $CO_2$ environment and rapidly reducing the pressure to expand and fuse the polymer into an interconnected scaffold structure; and leaching the porogen from the scaffold structure by immersing the structure in water to generate a porous article, thereby making the device. According to this aspect, the polymer may include a copolymer of lactide and glycolide (PLG) or alginate. Still further according to this aspect, the porogen is NaCl or sucrose.

Other features and advantages of the invention will be apparent from the following description of the preferred embodiments thereof, and from the claims. References cited are hereby incorporated by reference.

BRIEF DESCRIPTION OF THE DRAWINGS

Various features and advantages of the embodiments herein described can be fully appreciated as the same becomes better understood when considered in light of the accompanying drawings:

FIG. 1A is a photograph showing surface microcomputed tomograph and cross-sectional SEM images of PLG based T cell Trap.

FIG. 1B is a line graph showing cumulative release of ovalbumin (OVA) protein as a model antigen from OVA-T cell traps.

FIG. 1C is a bar graph showing the local cytokine concentration of MIP-la and RANTES at site of traps implanted subcutaneously in the backs of mice for 14 days. The values in B and C represent the average and standard deviation (n=5). FIGS. 1A-C show characterization of a model T cell Trap.

FIG. 2C is a series of FACS plots. Mice vaccinated with CFA-OVA at day 0 (DO) were implanted with traps containing OVA (OVA trap) and melanoma cell lysate (melanoma trap) at day 7 (D7) and the traps were then assayed at day 21 (D21). CD3(+) T cells were isolated and sorted from OVA and melanoma traps and stained with anti-CD8, Trp2 tetramer and OVA tetramer. Gates in FACS plots represent the CD8(+) T cells positive for OVA or Trp2 tetramer staining and numbers represent the percentage of CD8 T cells as indicated.

FIG. 2D is a bar graph showing the number of OVA specific and Trp2 specific T cells isolated from OVA Traps and Melanoma Traps. The values in B and D represent the average and standard deviation (n=5). **P<0:01. FIGS. 2A-D demonstrate that the traps are useful in discriminating T cells via antigen directed homing.

FIG. 4A is a photograph of an IL-2 ELISPOT assay results of beta cell targets cultured with T cells harvested from antigen loaded Traps and Controls. T cells were harvested 14 days after implantation in NOD mice at ages 11, 14 and 17 weeks. Each well represents reactions from T cells harvested from a single mouse.

FIG. 5A is a histogram depicting CD3(+) T cell infiltration into blank (Control) and ovalbumin (Antigen) loaded traps. Dot plots depicting CD8(+) OVA tetramer(+) T cells infiltrating blank (Control) and ovalbumin (Antigen) loaded traps. Gate and number represents percent of OVA(+) cytotoxic T cells isolated from traps.

FIG. 5B is a bar graph showing the number of CD3(+) T cells trapped in blank (control) and ovalbumin-loaded (Trap) alginate cryogels.

FIG. 5C is a bar graph showing the number of CD8(+) OVA(+) T cells trapped in blank (control) and antigen-loaded (Trap) alginate cryogels. Values in B and C represent the mean and standard deviation (n=4). *P<0.05. The data shown in FIGS. 5A-C demonstrate successful T cell capture and retention into alginate cryogel traps that contain an antigen lure. Traps with antigen alone are sufficient, and the addition of GM-CSF and CpG as adjuvants to the antigen enhances the T cell infiltrate.

FIG. 6A shows FACS plots of cells isolated from control control) and ovalbumin (OVA; antigen) loaded traps (which were implanted into OT-1 mice for 14 days). Cells were stained with anti-CD8 and OVA class I tetramers. The gates represent the OVA-specific, CD8(+) T cells and numbers provide the percentage of positive cells.

FIG. 6B shows the kinetics of CD8(+)OVA tetramer(+) T cells accumulating in traps (OVA trap) and controls (Control). Scaffolds were implanted in OT-1 mice for 7, 14 and 28 weeks.

FIG. 6C shows FACS analysis of CD3(+) T-cells. Mice were vaccinated with CFA-OVA at day 0 (DO) and implanted with traps containing OVA (OVA trap) and melanoma cell lysate (melanoma trap) at day 7 (D7). The traps were then assayed at day 21 (D21). CD3(+) T cells were isolated and sorted from OVA and melanoma traps and stained with anti-CD8, Trp2 tetramer and OVA tetramer. Gates in FACS plots represent the CD8(+) T cells positive for OVA or Trp2 tetramer staining and numbers represent the percentage of CD8 T cells as indicated.

FIG. 6D shows the number of OVA specific and Trp2 specific T cells isolated from OVA Traps and Melanoma Traps. The values in B and D represent the average and standard deviation (n=5). **P<0:01.

DETAILED DESCRIPTION OF THE INVENTION

Figure 2B:
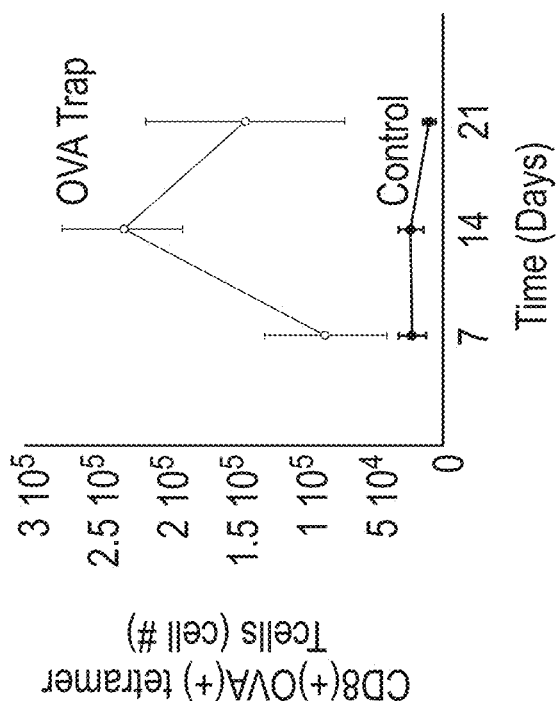
FIG. 2B is a line graph showing the kinetics of CD8(+) OVA tetramer(+) T cells accumulating in traps (OVA Trap) and controls (Control). Scaffolds were implanted in OT-1 mice for 7, 14 and 28 weeks.

The present invention provides a solution to the problem of identifying and collecting rare cells or cells with occur at low frequency in the body. Particular embodiments described herein relate to collection devices, for example cell traps, which are useful in the collection of such cells. The device includes a scaffold composition which incorporates or is coated with a plurality of antigens and, optionally, recruiting agents, allowing the device to attract, adhere to, and capture or sequester targeted cells. The device executes these functions by a variety of methods that include direct or indirect interaction with the antigens, recruiting agents, or other molecules present therein. Depending on the application for which the device is used, the device regulates capture and survival of the targeted cells through the physical or chemical characteristics of the scaffold itself. For example, the scaffold composition is differentially permeable, allowing cell passage only in certain physical areas of the scaffold. The permeability of the scaffold composition is regulated, for example, by selecting or engineering a material for greater or smaller pore size, density, polymer cross-linking, stiffness, toughness, ductility, or visco-elascticity. The scaffold composition may contain physical channels or paths through which targeted cells interact with the device and/or move into a specific compartment or region of the device. To facilitate the compartmentalization, the scaffold composition is optionally organized into compartments or layers, each with a different permeability, so that cells are sorted or filtered to allow access to only a certain sub-population of cells. Sequestration of target cell populations in the device may also be regulated by the degradation, de- or re-hydration, oxygenation, chemical or pH alteration, or ongoing self-assembly of the scaffold composition. Following their capture, the targeted cells may be allowed to grow or expand within the device with the help of stimulatory molecules, cytokines, and other co-factors present in the device. In other instances, non-targeted cells which have otherwise infiltrated the device may be rejected or removed using negative selection agents.

The cells that are trapped within the devices of the invention are primarily immune cells. In certain embodiments, the invention relates to T-cell traps. In other embodiments, the invention relates to B-cell traps. Yet in other embodiments, the invention relates to a combination of traps, e.g., a combination of T-cell traps and B-cell traps. The traps described herein may also be configured to trap antigen presenting cells (APCs), such as, for example, autoreactive APCs. Examples of auto-reactive APCs that may be trapped include, for example, dendritic cells (DCs), macrophages, or a combination of thereof. In other embodiments, a plurality of traps may be employed, e.g., traps which are configured for trapping both lymphocytes and APCs. For example, antigen-specific cells or disease specific-cells such as T cells, dendritic cells (DCs), or macrophages may be trapped, either separately or together, for analyses, reprogramming or depletion. The trapped immune cells, e.g., lymphocytes and APCs, are optionally harvested and analyzed to identify and characterize targets for disease diagnosis or immunotherapy. The trapped cells may also be reprogrammed or expanded for developing compositions or formulations that are to be used in therapy.

The invention is further described in more detail in the subsections below.

I. Devices for Recruiting and Trapping Immune Cells

In one aspect, the present invention provides cell-trapping devices. The devices contain a physiologically compatible porous polymer scaffold, a plurality of antigens and, optionally, one or more recruiting agents which attract an immune cell.

In one embodiment, the devices contain scaffolds which are made up of physiologically-compatible and optionally biodegradable polymers. Examples of polymers that are employable in the devices are known in the art. See, for example, US pub. No. 2011/0020216, the entire contents of which are incorporated herein by reference. Representative examples of such polymers include, but are not limited to, poly(lactide)s, poly(glycolide)s, poly(lactic acid)s, poly(glycolic acid)s, polyanhydrides, polyorthoesters, polyetheresters, polycaprolactones, polyesteramides, polycarbonates, polycyanoacrylates, polyurethanes, polyacrylates, and blends or copolymers thereof. Biodegradable scaffolds may comprise biodegradable materials, e.g., collagen, alginates, polysaccharides, polyethylene glycol (PEG), poly(glycolide) (PGA), poly(L-lactide) (PLA), or poly(lactide-co-glycolide) (PLGA) or silk. In one embodiment, the scaffold or scaffold device may comprises a biocompatible polymer matrix that is wholly or partly biodegradable. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-ε-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers. In another embodiment, the scaffolds may be fabricated from a variety of synthetic polymers and naturally-occurring polymers such as, but not limited to, collagen, fibrin, hyaluronic acid, agarose, and laminin-rich gels. In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogeneous, aligned, repeating, or random.

In one embodiment, the polymers are hydrogel-forming agents, e.g., glycolides and/or alginates. Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Glycolide/alginate polymers can be formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold.

Methods for fabricating the scaffold compositions are known in the art. See, for example, Martinsen et al. (Biotech. & Bioeng., 33 (1989) 79-89), (Matthew et al. (Biomaterials, 16 (1995) 265-274), Atala et al. (J Urology, 152 (1994) 641-643), and Smidsrod (TIBTECH 8 (1990) 71-78), the disclosures in which are incorporated by reference herein in their entirety.

Exemplary devices utilize glycolides or alginates of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic cross-linking through divalent cations to gel the polymer. For example, U.S. Pat. No. 6,642,363, which incorporated herein by reference, discloses methods for making and using polymers containing polysaccharides such as alginates.

The scaffolds of the invention may be porous such that the scaffolds can sustain antigen presentation and attract and trap immune cells. In one embodiment, the devices contain porous scaffolds, wherein the pores have a diameter between 10 nm to 500 μm. In these embodiments, the invention utilizes devices comprising nanoporous scaffolds, wherein the pores have a diameter of less than about 10 nm (e.g., about 0.5 nm, about 1 nm, about 3 nm, about 5 nm, about 7 nm, about 9 nm, and greater). In another embodiment, the scaffolds are microporous wherein the pores have a diameter in the range of about 100 nm-20 μm (e.g., about 200 nm, about 500 nm, about 700 nm, about 1 μm, about 2 μm, about 5 μm, about 7 μm, about 10 μm, about 12 μm, about 15 μm, about 17 μm, about 20 μm or more). In another embodiment, the scaffolds are macroporous wherein the diameter of the pores about 20 μm-500 μm (e.g., 30 μm, 50 μm, 70 μm, 100 μm, 200 μm, 300 μm, 400 μm, or more). Particularly, the diameter of the pores is greater than about 100 μm and preferably, greater than about 400 μm. In the exemplified embodiments, the scaffold is macroporous with aligned pores of about 200-500 μm in diameter.

Methods of making polymer matrices having the desired pore sizes and pore alignments are described in the art, e.g., US pub. No. 2011/0020216 and U.S. Pat. No. 6,511,650, the pertinent disclosures in which are incorporated herein by reference.

II. Antigens

The devices of the invention include one or more antigens, which may be naturally-occurring, synthetically produced, or recombinant compounds, e.g., peptides, polypeptides, proteins, nucleic acids, small molecules, haptens, carbohydrates, or other agents, including fragments thereof or combinations thereof. More specifically, the antigens are peptides or proteins or immunologically active fragments thereof. In one embodiment, the antigens described herein are purified. Purified compounds contain at least 60% by weight (dry weight) of the compound of interest. Particularly, the antigens are at least 75% pure, preferably at least 90% pure, and more preferably at least 99% pure. Purity is measured by any appropriate standard method, for example, by column chromatography, polyacrylamide gel electrophoresis, or HPLC analysis.

The antigens may be self-antigens or non-self antigens.

Representative examples of non-self antigens include, for example, antigens derived from a pathogen selected from the group consisting of a virus, a bacteria, a protozoan, a parasite, and a fungus. In these embodiments, the non-self antigens may be derived from *Mycobacterium bovis*, Human Papillomavirus (HPV), Human immunodeficiency virus, a pox virus, smallpox virus, Ebola virus, Marburg virus, dengue fever virus, influenza virus, parainfluenza virus, respiratory syncytial virus, rubella virus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, hepatitis E virus, SARS CoV, MERS CoV, Enterovirus, *Borrelia* species, *Bacillus anthracis*, *Borrelia burgdorferi*, *Bordetella pertussis*, *Camphylobacter jejuni*, *Chlamydia* species, *Chlamydial psittaci*, *Chlamydial trachomatis*, *Clostridium species*, *Clostridium tetani*, *Clostridium botulinum*, *Clostridium perfringens*, *Corynebacterium diphtheriae*, *Coxiella* species, an *Enterococcus* species, *Erlichia* species, *Escherichia coli*, *Francisella tularensis*, *Haemophilus* species, *Haemophilus influenzae*, *Haemophilus parainfluenzae*, *Lactobacillus* species, a *Legionella* species, *Legionella pneumophila*, *Leptospirosis interrogans*, *Listeria* species, *Listeria monocytogenes*, *Mycobacterium* species, *Mycobacterium tuberculosis*, *Mycobacterium leprae*, *Mycoplasma* species, *Mycoplasma pneumoniae*, *Neisseria* species, *Neisseria meningitidis*, *Neisseria gonorrhoeae*, *Pneumococcus* species, *Pseudomonas* species, *Pseudomonas aeruginosa*, *Salmonella species*, *Salmonella typhi*, *Salmonella enterica*, *Rickettsia* species, *Rickettsia rickettsii*, *Rickettsia typhi*, *Shigella* species, *Staphylococcus* species, *Staphylococcus aureus*, *Streptococcus* species, *Streptococccus pnuemoniae*, *Streptococcus pyrogenes*, *Streptococcus mutans*, *Treponema* species, *Treponema pallidum*, a *Vibrio* species, *Vibrio cholerae*, *Yersinia pestis*, Methicillin-resistant *Staphylococcus aureus*, *Aspergillus* species, *Aspergillus*, *funigatus*, *Aspergillus flavus*, *Aspergillus calvatus*, *Candida* species, *Candida albicans*, *Candida tropicalis*, *Cryptococcus* species, *Cryptococcus neoformans*, *Entamoeba histolytica*, *Histoplasma capsulatum*, *Leishmania* speceis, *Nocardia asteroides*, *Plasmodium falciparum*, *Stachybotrys chartarum*, *Toxoplasma gondii*, *Trichomonas vaginalis*, *Toxoplasma* species, *Trypanosoma brucei*, *Schistosoma mansoni*, *Fusarium* species, *Trichophyton* species, *Plasmodium* species, *Toxoplasma* species, *Entamoeba* species, *Babesia* species, *Trypanosoma* species, *Leshmania* species, *Pneumocystis* species, *Pneumocystis jirovecii*, *Trichomonas* species, *Giardia* species, *Schisostoma* species, *Cryptosporidium* species, *Plasmodium* species, *Entamoeba* species, *Naegleria* species, *Acanthamoeba* species, *Balamuthia* species, *Toxoplasma* species, *Giardia* species, *Trichomonas* species, *Leishmania* species, and *Trypanosoma* species.

Alternately, the devices contain a plurality of self-antigens, which are optionally linked to or associated with a disease or disorder. Preferably, the self-antigens are specifically associated with a human disease or a disorder. In one embodiment, the self-antigen is associated with an autoimmune disorder selected from the group consisting of rheumatoid arthritis, lupus, celiac disease, inflammatory bowel disease or Crohn's disease, sjögren's syndrome polymyalgia rheumatic, multiple sclerosis, ankylosing spondylitis, Type 1 diabetes, alopecia areata, vasculitis, temporal arteritis, etc. Specific types of antigens, including fragments thereof, which are associated with type 1 diabetes, multiple sclerosis, Crohn's disease, and rheumatoid arthritis and the like have been characterized in literature. For example, rheumatoid arthritis-related antigen is a 47 kDa protein (RA-A47). See Hattori et al, J Bone Miner Metab., 18(6):328-34 (2000). In Crohn's disease, the antigen may be bacterial flagellin. See, Lodes et al., J Clin Invest. 113(9):1296-306 (2004). Likewise, major myelin proteins such as myelin basic protein (MBP) and proteolipid protein (PLP), are likely to be of importance in the course of multiple sclerosis (MS). See, deRosbo et al., J Clin Invest. 92(6): 2602-260 (1993). In the context of type 1 diabetes, a plurality of autoantigens may be involved, such as, preproinsulin (PPI), islet-specific glucose-6-phosphatase (IGRP), glutamate decarboxylase (GAD65), insulinoma antigen-2 (IA-2), chromogranin A and heat shock protein 60. See Roep et al., Cold Spring Harb Perspect Med. 2(4), 2012 (PMID: 22474615).

In another embodiment, the self-antigens are associated with a cancer. Representative types of cancer antigens include, for example, MAGE-1, MAGE-2, MAGE-3, CEA, Tyrosinase, midkin, BAGE, CASP-8, β-catenin, β-catenin, γ-catenin, CA-125, CDK-1, CDK4, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf 112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Glil, Cav-1, cathepsin B, CD74, E-cadherin, EphA2/Eck, Fra-1/Fosl 1, GAGE-1, Ganglioside/GD2, GnT-V, β1,6-N, Ki67, Ku70/80, PROX1, PSCA, SOX10, SOX11, Survivin, UPAR, WT-1, Dipeptidyl peptidase IV (DPPIV), adenosine deaminase-binding protein (AD Abp), cyclophilin b, Colorectal associated antigen (CRC)-C017-1A/GA733, T-cell receptor/CD3-zeta chain, GAGE-family of tumor antigens, RAGE, LAGE-I, NAG, GnT-V, RCAS1, α-fetoprotein, p120ctn, Pmel117, PRAME, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, PlA, Connexin 37, Ig-idiotype, p15, GM2, GD2 gangliosides, Smad family of tumor antigens, lmp-1, EBV-encoded nuclear antigen (EBNA)-I, UL16-binding protein-like transcript 1 (Multi), RAE-1 proteins, H60, MICA, MICB, and c-erbB-2, or an immunogenic peptide thereof, and combinations thereof.

III. Combination of Scaffold Compositions and Antigens

The antigens may be combined with the scaffold compositions using any known methods, including covalent and non-covalent interactions. Types of non-covalent interactions include, for example, electrostatic interactions, van der Waals' interactions, π-effects, hydrophobic interactions, etc. The antigens may also be attached or tethered to scaffold compositions via covalent interactions. Methods for attaching antigens to scaffolds/surfaces are known in the art, e.g., surface absorption, physical immobilization, e.g., using a phase change to entrap the substance in the scaffold material. In one specific embodiment, an antigenic composition containing a protein is mixed with the scaffold composition while it is in an aqueous or liquid phase, and after a change in environmental conditions (e.g., pH, temperature, ion concentration), the liquid gels or solidifies thereby entrapping the antigen. Alternatively, covalent coupling via alkylating or acylating agents may be used to provide a stable, long-term presentation of an antigen on the scaffold in a defined conformation. Exemplary reagents and methods for covalently coupling peptides/proteins to polymers are known in the art. See, for example, U.S. Pat. No. 6,001,395, the contents of which as they relate to the present invention are incorporated herein by reference. In other embodiments, the antigens are encapsulated into the scaffolds. Methods for encapsulating antigens into suitable scaffolds, e.g., PLGA microspheres, are known in the art. See, for example, U.S. Pat. No. 6,913,767 and WO/1995/011010, the contents of which as they relate to the present invention are incorporated herein by reference.

The antigens may be formulated to interact with the immune cell via direct binding or indirect binding. Types of direct binding include, for example, engagement or coupling of the antigen with the cognate receptor, e.g., B-cell receptor or T-cell receptor. Indirect binding may occur through the intermediacy of one or more secondary agents or cell-types. For example, the antigen may first bind to a B-cell or an antigen-presenting cell (APC), get processed (e.g., degraded) and presented on cell-surface major-histocompatibility complexes (MHC), to which the target cell population, e.g., T-cell, binds. Alternately, the antigen may recruit other intermediary cells that secrete various cytokines, growth factors, chemokines, etc., which in turn attract the target immune cell population to the devices. Whatever the mechanism may be, the recited components act in concert to recruit and sequester immune cells to the devices of the instant invention.

The antigen may be derived from a cell lysate, a fractionated cell lysate, freshly harvested cells, biological fluids (including blood, serum, ascites), tissue extracts, etc. In one embodiment, the antigens are derived from lysates of target cells to which the desired immune cells, e.g., B-cells or T cells bind. In these embodiments, the antigens are first fractionated in the cell lysate prior to loading the cell traps. The lysates may be derived from an autoimmune disease-specific cells, e.g., pancreatic beta cells associated with type I diabetes, neuronal cells associated with multiple sclerosis, a bone/joint antigen associated with rheumatoid arthritis, an antigen associated with inflammatory bowel disease or Crohn's disease. Alternately, the lysates may be derived from cancer cells, e.g., individual cells obtained from tumor samples or tissue cultures or bulk tumor cells obtained from biopsies or histological preparations.

IV. Recruitment Agents

The devices of the invention may also contain one or more recruiting agents. The recruiting agent may be an agent selected from the group consisting of a T-cell recruiting agent, a B-cell recruiting agent, a dendritic cell recruiting agent, and a macrophage recruiting agent, or a combination thereof.

In one embodiment, the devices contain T-cell recruiting agents. Non-limiting examples of T-cell recruiting agents include, but are not limited to, CCL1, CCL2 (MCP-1), CCL-3, CCL-4, CCL-5 (RANTES), CCL-17, CCL-22, CXCL12 and XCL1, or a fragment thereof, a variant thereof, or a combination thereof. Various homologs of the aforementioned T-cell recruiting agents, including functional fragments thereof, or variants thereof, are known in the art. Representative examples of homologs include related proteins from fly, mouse, rat, pig, cow, monkey, humans or the like. The homologs preferably include human or mouse homologs of the aforementioned recruiting agents having the NCBI accession numbers shown in Table 1.

TABLE 1

Chemokines for trapping T-cells, including related NCBI accession numbers:

| Chemokine | NCBI Accession No. |
|---|---|
| CCL1 | NM_002981.2 (human) |
| | GI:523498696 (human) |
| | NM 011329.3 (mouse) |
| | GI:257153404 (mouse) |
| CCL2 (MCP-1) | NM_002982.3 (human) |
| | GI:56119169 (human) |
| | NM_011333.3 (mouse) |
| | GI:141803162 (mouse) |
| CCL3 | NM_002983.2 (human) |
| | GI: 121582465 (human) |
| | NM 011337.2 (mouse) |
| | GI: 126432552 (mouse) |
| CCL4 | NM 002984.3 (human) |
| | GI:748585189 (human) |
| | NM 013652.2 (mouse) |
| | GI:126366031 (mouse) |
| CCL5 (RANTES) | NM_002985.2 (human) |
| | GI: 22538813 (human) |
| | NM_013653.3 (mouse) |
| | GI: 164698427 (mouse) |
| CCL17 | NM_002987.2 (human) |
| | GI:22538801 (human) |
| | NM_011332.3 (mouse) |
| | GI:225735578 (mouse) |
| CCL19 | NM_006274.2 (human) |
| | GI:22165424 (human) |
| | NM 011888.2 (mouse) |
| | GI: 10518345 (mouse) |
| CCL22 | NM_002990.4 (human) |
| | GI:300360575 (human) |
| | NM_009137.2 (mouse) |
| | GI: 154240695 (mouse) |
| CXCL12 | NM_199168.3 (human) |
| | GI: 291045298 (human) |
| | NM_001277990.1 (mouse) |
| | GI: 489406389 (mouse) |
| XCL1 | NM_002995.2 (human) |
| | GI:312434026 (human) |
| | NM 008510.1 (mouse) |
| | GI: 6678711 (mouse) |

The devices may also contain any combination of the aforementioned recruiting agents, for example, at least 2, at least 3, at least 4, at least 5, at least 6, at least 7, at least 8, at least 9 or greater number of the recruiting agents listed in Table 1. In related embodiments, the devices contain all the recruiting agents listed in Table 1.

In other embodiments, the invention provides devices for recruiting dendritic cells or macrophages or a combination thereof. Non-limiting examples of dendritic cell/macrophage recruiting agents include, but are not limited to, CCL2, CCL3, CCL5, CCL7, CCL8, CCL13, CCL17, and CCL22 or a functional fragment thereof, a variant thereof, or a combination thereof. Representative examples of homologs of the dendritic cell/macrophage recruiting agents include related proteins from fly, mouse, rat, pig, cow, monkey, humans or the like. The homologs preferably include human or mouse homologs of the aforementioned recruiting agents having the NCBI accession numbers shown in Table 2.

TABLE 2

Chemokines for trapping dendritic cells and/or macrophages, including related NCBI accession numbers:

| Chemokine | NCBI Accession No. |
|---|---|
| CCL2 | NM 002982.3 (human) |
| | GI:56119169 (human) |

TABLE 2-continued

Chemokines for trapping dendritic cells and/or macrophages, including related NCBI accession numbers:

| Chemokine | NCBI Accession No. |
|---|---|
| | NM 011333.3 (mouse) |
| | GI:141803162 (mouse) |
| CCL3 | NM_002983.2 (human) |
| | GI: 121582465 (human) |
| | NM_011337.2 (mouse) |
| | GI: 126432552 (mouse) |
| CCL5 | NM 002985.2 (human variant 1) |
| | GI: 22538813 (human) |
| | NM_013653.3 (mouse) |
| | GI: 164698427 (mouse) |
| CCL7 | NM_006273.2 (human) |
| | GI:428673540 (human) |
| | NM_013654.3 (mouse) |
| | GI:226958664 (mouse) |
| CCL8 | NM_005623.2 (human) |
| | GI:22538815 (human) |
| | NM 021443.3 (mouse) |
| | GI:255708468 (mouse) |
| CCL13 | NM_005408.2 (human) |
| | GI:22538799 (human) |
| CCL17 | NM_002987.2 (human) |
| | GI:22538801 (human) |
| | NM 011332.3 (mouse) |
| | GI:225735578 (mouse) |
| CCL22 | NM_002990.4 (human) |
| | GI:300360575 (human) |
| | NM_009137.2 (mouse) |
| | GI: 154240695 (mouse) |

The aforementioned devices for recruiting DC/macrophage-recruiting may contain any combination of the aforementioned recruiting agents, for example, at least 2, at least 3, at least 4, at least 5, at least 6, at least 7, or greater number of the recruiting agents listed in Table 2. In related embodiments, the devices contain all the recruiting agents listed in Table 2.

In related embodiments, the invention provides devices for recruiting B-cells. Non-limiting examples of B-cell recruiting agents include, but are not limited to, SDF-1, BLC, BCL-2 and BCA-1 or a functional fragment thereof, a variant thereof, or a combination thereof. Representative examples of homologs of the B-cell recruiting agents include homologs of the aforementioned proteins in fly, mouse, rat, pig, cow, monkey, humans, or the like. The homologs preferably include human or mouse homologs of the aforementioned recruiting agents having the NCBI accession numbers shown in Table 3.

TABLE 3

Chemokines for trapping B-cells, including related NCBI accession numbers:

| Chemokine | NCBI Accession No. |
|---|---|
| SDF-1 | NM_000609.6 (human) |
| | GI:489406302 (human) |
| | NM 001012477.2 (mouse) |
| | GI:270309154 (mouse) |
| BLC | NM_006419.2 (human) |
| | GI:194733765 (human) |
| | NM_018866.2 (mouse) |
| | GI:118130712 (mouse) |
| BCL-2 | NM_000657.2 (human) |
| | GI:72198345 (human) |
| | NM 009741.4 (mouse) |
| | GI:545477919 (mouse) |

TABLE 3-continued

Chemokines for trapping B-cells, including related NCBI accession numbers:

| Chemokine | NCBI Accession No. |
|---|---|
| BCA-1 | NM_006419.2 (human) |
| | GI:194733765 (human) |
| | NM_018866.2 (mouse) |
| | GI:118130712 (mouse) |

The aforementioned devices for recruiting B-cells may contain any combination of the aforementioned recruiting agents, for example, at least 2, at least 3, or all 4 of the recruiting agents listed in Table 3, or variants thereof or fragments thereof. Preferably, the devices contain all recruiting agents listed in Table 3 or fragments thereof.

Further embodiments relate to devices containing agents that are capable of recruiting a plurality of immune cells, e.g., a combination of T-cells and DC/macrophages, a combination of T-cells and B-cells, a combination of B-cells and DC/macrophages, etc. Accordingly, in one embodiment, the invention provides for devices that recruit both T-cells and dendritic cells/macrophages, comprising, recruitment agents selected from at least one agent from Table 1 and at least one agent from Table 2. In a related embodiment, the invention provides for devices that recruit both B-cells and dendritic cells/macrophages, comprising, recruitment agents selected from at least one agent from Table 2 and at least one agent from Table 3. In yet another embodiment, the invention provides for devices that recruit both T-cells and B-cells, comprising, recruitment agents selected from at least one agent from Table 1 and at least one agent from Table 3.

In devices that are capable of recruiting a combination of immune cells, various combinations and sub-combinations of recruitment agents from the aforementioned tables may be employed. For example, devices designed for recruiting both T-cells and DC/macrophages may contain at one agent from Table 1 and two agents from Table 2, two agents from Table 1 and one agent from Table 2, two agents from Tables 1 and 2, etc. Likewise, devices designed for recruiting both B-cells and DC/macrophages may contain at one agent from Table 2 and two agents from Table 3, two agents from Table 2 and one agent from Table 3, two agents from Tables 2 and 3, etc.; devices designed for recruiting both T-cells and B-cells may contain at one agent from Table 1 and two agents from Table 3, two agents from Table 1 and one agent from Table 3, two agents from Tables 1 and 3, etc. Thus, in one representative embodiment, the device is adapted for the recruitment of a combination of T-cells and dendritic cells/macrophages, comprising, CCL17, CCL22, a variant thereof or a fragment thereof, or a combination thereof. Representative examples of homologs of the recruiting agents, including fragments or variants thereof include related proteins from fly, mouse, rat, pig, cow, monkey, humans or the like. The homologs preferably include human or mouse homologs the aforementioned recruiting agents having the NCBI accession numbers shown in Table 2.

The devices/traps may also be adapted to preferentially recruit certain types of immune cell combinations, e.g., a combination of lymphocytes and APCs, compared to other hematopoietic cells, e.g., platelets, red-blood cells, etc. Such devices may contain any combination of recruitment agents listed in Tables 1, 2, and 3.

The devices of the instant invention are adapted for the preferential recruitment of a single type or single sub-type of cell, for example, preferential recruitment of T-cells and particularly a subset of Treg cells or NK cells. Preferential recruitment is characterized by an accumulation of at least 10%, at least 20%, at least 30%, at least 50%, at least 75%, at least 100%, at least 2-fold, at least 5-fold, at least 8-fold, at least 10-fold, or greater increase in one or more of a particular type of immune cells (e.g., T cells, B-cells, DC/macrophages) in the device compared to other types of immune cells in the device (or in control traps that are devoid of recruitment agents). In devices that are adapted to recruit a combination of immune cells, e.g., a combination of T-cells and DC/macrophages, preferential recruitment is characterized where the total percentage of recruited cells is at least 10%, at least 20%, at least 30%, at least 50%, at least 75%, at least 100%, at least 2-fold (i.e., 200%), at least 5-fold, at least 8-fold, at least 10-fold, or greater than other types of immune cells in the device (or in control traps). Particularly, preferential recruitment is characterized by 1-10 fold increase in the number of the cells of interest compared to other immune cells.

V. Additional Agents

Embodiments of the invention further provide for devices for trapping immune cells which comprise a plurality of additional agents. In such embodiments, the additional agent may comprise a growth factor, a cytokine, a chemokine, an interleukin, an adhesion signaling molecule, an integrin signaling molecule or a fragment thereof or a combination thereof.

Representative examples of growth factors/cytokines include, but are not limited to, adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), foetal Bovine Somatotrophin (FBS) glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), keratinocyte growth factor (KGF), migration-stimulating factor (MSF), myostatin (GDF-8), nerve growth factor (NGF), neurotrophins, platelet-derived growth factor (PDGF), thrombopoietin (TPO), T-cell growth factor (TCGF), transforming growth factor (TGF-α or TGF-β), tumor necrosis factor-alpha(TNF-α), vascular endothelial growth factor (VEGF), Wnt, placental growth factor (PGF), or functional fragment thereof, or a combination thereof.

Representative types of interleukins include, but are not limited to, IL-1 (activates T cells, B-cells, NK cells, and macrophages), IL-2 (activates B-cells and NK cells), IL-3 (stimulates non-lymphoid cells), IL-4 (growth factor for activated B cells, resting T cells, and mast cells), IL-5 (for differentiation of activated B cells), IL-6 (growth factor for plasma cells and T-cells), IL-7 (growth factor for pre B-cells/pre T-cells and NK cells), IL-10 (activates macrophages, B-cells, mast cells, Th1/Th2 cells), IL-12 (activates T cells and NK cells), IL-17 (activates Th cells). Functional fragments of interleukins, which are characterized by their ability to modulate the activity of target cells, may also be employed. Representative types of interleukin molecules, including, NCBI accession numbers of human and/or mouse homologs thereof, are provided in Table 4.

TABLE 4

Types of interleukins that may be employed in the devices.

| Interleukins | NCBI Accession Nos. |
| --- | --- |
| IL-1 | BC008678.1; GI:14250476 (human) |
|  | BC011437.1; GI:15030320 (mouse) |
| IL-2 | NM_000586.3 GI:125661059 (human) |
|  | K02292.1; GI:198330 (mouse) |
| IL-4 | NM_172348.2; GI: 391224449 (human) |
|  | NM 021283.2; GI:226874825 (mouse) |
| IL-5 | NM 000879.2; GI:28559032 (human) |
|  | NM 010558.1; GI: 6754335 (mouse) |
| IL 10 | NM 000572.2; GI:24430216 (human) |
|  | NM 010548.2; GI:291575143 (mouse) |
| IL-12 (Beta2) | U64198.1; GI:1685027 (human) |
|  | U64199.1; GI:1685029 (mouse) |
| IL-17 (A) | NM 002190.2; GI:27477085 (human) |
|  | NM 010552.3; GI:142367609 (mouse) |

Optionally, the devices may contain adhesion molecules, which may also serve as signaling agents. Representative examples of adhesion signaling molecules include, but are not limited to, fibronectin, laminin, collagen, thrombospondin 1, vitronectin, elastin, tenascin, aggrecan, agrin, bone sialoprotein, cartilage matrix protein, fibrinogen, fibrin, fibulin, mucins, entactin, osteopontin, plasminogen, restrictin, serglycin, SPARC/osteonectin, versican, von Willebrand Factor, polysaccharide heparin sulfate, connexins, collagen, RGD (Arg-Gly-Asp) and YIGSR (Tyr-Ile-Gly-Ser-Arg) peptides and cyclic peptides, glycosaminoglycans (GAGs), hyaluronic acid (HA), condroitin-6-sulfate, integrin ligands, selectins, cadherins and members of the immunoglobulin superfamily Other examples include neural cell adhesion molecules (NCAMs), intercellular adhesion molecules (ICAMs), vascular cell adhesion molecule (VCAM-1), platelet-endothelial cell adhesion molecule (PECAM-1), L1, and CHL1. Functional fragments of the adhesion molecules, which are characterized by their ability to modulate the binding of target cells to the devices of the invention, may also be employed. Particularly, adhesion molecules comprise peptides or cyclic peptides containing the amino acid sequence arginine-glycine-aspartic acid (RGD), which is known as a cell attachment ligand and found in various natural extracellular matrix molecules. A polymer matrix with such a modification provides cell adhesion properties to the scaffold of the invention, and sustains long-term survival of mammalian cell systems, as well as supporting cell growth and differentiation. The adhesion molecules may be coupled to the polymer matrix is accomplished using synthetic methods which are in general known to one of ordinary skill in the art and are described in the examples. See, e.g., Hirano et al., Advanced Materials, p. 17-25 (2004); Hermanson et al., Bioconjugate Techniques, p. 152-185 (1996); Massia and Hubbell, J. Cell Biol. 114:1089-1100 (1991; Mooney et al., J. Cell Phys. 151:497-505 (1992; and Hansen et al., Mol. Biol. Cell 5:967-975, (1994), the disclosures in which are incorporated by reference.

Depending on the target cell type, it may be preferable to employ adhesion signaling molecules that are specific for the target cells. Thus, in one embodiment, the devices contain adhesion receptors that are useful in the recruitment of T-cells. In other embodiments, the devices contain adhesion receptors that are useful in the recruitment of dendritic cells/macrophages. Yet in another embodiment, the devices contain adhesion receptors that are useful in the recruitment of B-cells.

In these embodiments, the devices may contain T-cell specific adhesion molecules, for example, a receptor selected from the group consisting of LFA-1, MAdCAM-1, VCAM-1, CD28 and CTLA-4 or a variant thereof, a fragment thereof or a combination thereof. Representative examples of human and mouse homologs of such T-cell specific adhesion molecules are provided in Table 5.

TABLE 5

Various types of T-cell adhesion receptors and the NCBI and GI accession numbers for known human and mouse homologs thereof:

| Receptor | NCBI Accession No. | GI Accession No. |
| --- | --- | --- |
| LFA-1 | NM 000211.4 (human) | GI:735367774 (human) |
|  | M60778.1 (mouse) | GI:198785 (mouse) |
| MAdCAM-1 | NM 130760.2 (human) | GI:109633021 (human) |
|  | D50434.2 (mouse) | GI: 60391311 (mouse) |
| VCAM-1 | NM 001078.3 (human) | GI:315434269 (human) |
|  | X67783.1 (mouse) | GI: 298116 (mouse) |
| CD28 | NM 006139.3 (human) | GI: 340545506 (human) |
|  | BC064058.1 (mouse) | GI: 39850201 (mouse) |
| CTLA-4 | NM 005214.4 (human) | GI: 339276048 (human) |
|  | U90270.1 (mouse) | GI:4099836 (mouse) |

Devices for recruiting DC/macrophages or B-cells may be similarly formulated to contain adhesion molecules specific for DC/macrophages or B-cells. Representative examples of B-cell-specific adhesion molecules include, for example, N-CAM (type 2), laminin or fibronectin, etc. Representative examples of adhesion molecules that are specific for macrophages or dendritic cells include, for example, ICAM-1 or VCAM-1. Depending on need, the devices may be specifically formulated to contain a subset of recruitment agents and adhesion molecules from the aforementioned Tables 1-5. For example, devices for recruiting both T-cells and dendritic cells may be formulated to contain a combination of CCL17 and CCL22 (from the list of chemokines) and VCAM-1 (from the list of adhesion molecules). Devices for recruiting both T and B lymphocytes may be similarly formulated by selective incorporation of various recruitment agents and adhesion molecules, which are optionally incorporated with one or more interleukins and/or cytokines.

VI. Devices for Recruiting Specific Subtypes of Immune Cells

The devices of the invention may also be formulated for preferentially recruiting one or more sub-populations of cells by using agents that specifically bind to cell-surface markers that are expressed in the cells. For example, in the context of T-cells, the devices may be adapted for the preferential recruitment of helper T-cells ($T_H$ cells; which differentially express CD4+), cytotoxic T-cells ($T_c$ cells; which differentially express CD8+), memory T-cells ($T_m$ cells; which differentially express CD45RO), suppressor T-cells ($T_s$ which cells), regulatory T-cells (Tregs; further characterized as FOXP3+ Treg cells and FOXP3-Treg), natural killer T-cells (NK cells; differentially express CD1d+), mucosal associated invariant (MAITs; differentially express MR1), gamma delta T cells, (γδ T cells; comprise TCRs containing one γ-chain and one δ-chain). Such agents which bind to cell-surface markers may include, for example, haptens, peptides, ligands, antibodies, or the like. Other routine techniques for enriching the isolates with one or more cell subtype may be optionally used in situ or ex situ.

Likewise, in the context of B-cells, the devices may be formulated for the preferential recruitment of specific B-cell subtype(s) using agents that selectively bind to the cell-surface markers expressed therein. Representative examples of B-cell subtypes that may be preferentially trapped include plasmablasts, plasma cells (differentially express CD27+/CD138+/CD319+), memory B cell (differentially express a combination of markers disclosed in Airoldi et al., Clin Cancer Research, 2004 10; 144), follicular (FO) B cell (express high levels of CD23 but are negative for CD1 or CD5), marginal zone (MZ) B cell (positive for CD21, CD1, CD9 but negative for CD23, CD5, and CD11b), B-1 cell (having a marker profile, e.g., CD20+CD27+CD43+CD70-), B-2 cell (similar to FO B cells and MZ B cells), regulatory B (Breg) cell (e.g., having a marker profile CD24+/CD38+), etc.

The devices may also be adapted to preferentially recruit various sub-types of antigen presenting cells. For example, in the context of dendritic cells, the devices may be adapted for the recruitment of myeloid dendritic cells (mDC, which includes the more common mDC-1 and the less common mDC-2) compared to plasmacytoid dendritic cells (pDC) or vice versa. In the context of macrophages, the devices may be adapted for the preferential recruitment of M1 (i.e., "killer" macrophages) compared to M2 (i.e., activated macrophages) or vice versa. The differences between the two is recognized in the art. For example, the M1 subtype secretes high levels of IL-12 and low levels of IL-10; the reverse is true for the M2 subtype. Tumor-associated macrophages are mainly of the M2 phenotype, and seem to actively promote tumor growth.

The device may also be adapted for recruiting immune cells that are specific for a disease. For example, a plurality of T cells that are specific for a particular type of autoimmune disease may be recruited. Thus in one embodiment, devices that are useful in the diagnosis of autoimmune disorders may be formulated to contain recruitment agents that are specific to the immune cells implicated in the disorder. Such recruitment agents may, for example, be specific to regulatory T cells (Tregs), suppressor T cells (Ts) or a combination thereof. In a related embodiment, devices that are useful in the diagnosis of cancers may be formulated to contain recruitment agents for preferentially recruiting cancer-specific T-cell types, e.g., cytotoxic T cells (Tc), natural killer cells (NK) or a combination thereof.

In certain embodiments, the device is useful to pan for disease-specific cells. Such may include, for example, cells that directly promote disease progression. In the context of many autoimmune diseases, the disease may be mediated and promoted via targeted killing of specific population of cells, e.g., beta cells of pancreas in T1D and neuronal cells in multiple sclerosis. In other autoimmune diseases, the disease may be precipitated by targeted attack of specific epitopes such as, for example, rheumatoid factors (RF) and citrullinated peptides (ACPA) in the context of rheumatoid arthritis and antigens present in the gut flora in the context of Crohn's disease. The targeted destruction of the cells generally involves specific type or subset of immune cells. Thus, based on the nature and properties of the cellular targets, immune cells that are specific thereto may be preferentially trapped using the devices of the instant invention.

In the aforementioned embodiments, the devices are provided with antigens to which disease-specific immune cells, e.g., T cells, B cells, dendritic cells, macrophages, etc., bind. These autoimmune cells can be trapped and optionally re-programmed to a non-autoimmune phenotype. Methods of reprogramming T-cells to pluripotency are known in the art. See, Nishimura et al., Stem Cell 12, 114-126 (2013); Themeli et al., Nature Biotechnology 31, 928-933 (2013). In certain instances, particularly in the context of cancer-specific T-cells, the reprogrammed cells may be rejuvenated to target the cancer. Alternately, in the context of T-cells that are specific to autoimmune diseases, the trapped cells may be eliminated (removed from the body) or killed.

VII. Methods of Making/Using the Devices

The devices of the invention are porous devices engineered to sustain antigen presentation. Representative examples of devices are shown in FIGS. 1A and 1B. As shown in the Drawings, the pores allow space for T cell infiltration and expansion. Methods for fabricating porous scaffolds have been described in the art. See, for example, US pub. Nos. 2011/0020216, 2013/0202707, 2011/0020216 and U.S. Pat. No. 8,067,237, the disclosures in which are incorporated by reference herein. For example, traps may be fabricated with copolymers of lactide and glycolide (PLG) to generate PLG cell traps using a gas forming process (as described in detail in the Examples). Antigens are physically adsorbed onto PLG polymer, by incubating the composition of polymers and the antigen. Alternately, PLG microspheres encapsulating the antigens may be made using a standard double emulsion. PLG-antigen spheres are then frozen and lyophilized and mixed with a porogen or a pore-forming agent, and compression molded. The resulting disc is allowed to equilibrate within a high-pressure $CO_2$ environment, and a rapid reduction in pressure causes the polymer particles to expand and fuse into an interconnected scaffold structure. The porogen is leached from the scaffolds by immersion in water yielding antigen-laden cell traps that are about 90% porous. The porosity may be altered by routine methods, e.g., by varying the concentration of the porogen and/or using other biopolymers as scaffolding agents. The resulting porosity of the device is between 40% and 99%, preferably between 50% and 90%, particularly preferably between 60% and 80% or more.

Device Implantation/Removal

The device can be implanted by any means known in the art, such as intravenous administration, implantation, e.g., subcutaneous implantation or implantation as a microneedle patch, intraperitoneal administration or intramuscular injection. The period of implantation which is sufficient for the cells of interest to migrate into the porous matrix can be between two hours and a few months, e.g., 0.5, 1, 2, 5, 7, 14, 25, 30 35, 38, 45, 50, 60 or more days. The period of implantation may be at least one day, during which time, $1\times10^9$ to $1\times10^{10}$ cells accumulate and/or are extracted from the device after residence in a bodily tissue.

A plurality of devices may be implanted into a subject. In one embodiment, at least 1, at least 3, at least 10, at least 30, at least 50, at least 100, at least 300, at least 500, at least 1000, or more devices are implanted into a subject. Application of the devices may be uniform (e.g., each device containing the same antigen) or varied (e.g., multiple devices containing different antigens).

The device need not be removed from the body for isolation, characterization, analysis and/or expansion/reprogramming of cells. In one embodiment, the cells are removed without physically removing the device from the site of the implant. In one embodiment, cells that are in the periphery of the device, e.g., cells that are located within a radius of about 1 μm, about 2 μM, about 5 μM, about 10 μm, about 20 μm, about 60 μm, about 100 μm, about 300 μm, about 0.5 mm, about 1.0 mm, about 3.0 mm, 5.0 mm, about 10 mm, 50 mm, etc. of the device may be removed and optionally expanded or reprogrammed. Cells may also be purified through cell sorting techniques (FACS or MACS) or resolution techniques, e.g., using FICOLL gradients, to achieve a more homogenous population of cells. In another embodiment, the cells that are attached onto or located within the device may be removed and optionally expanded or reprogrammed without removing the device. Methods for removing cells from implanted devices are known in the art. Such may include, for example, chemical or enzymatic treatments. For instance, combinations of different classes of detergents in low dosages, for example, a nonionic detergent, Triton X-100, and an anionic detergent, sodium dodecyl sulfate, may disrupt membranes and aid in the removal of cells from implants. Alternately, connective tissue enzymes such as collagenase, Trypsin, dispase may be used to dislodge cells. The Traps may also be subjected to sensitive mechanical disruptions (such as mortor and pistal, or tissue homogenization) to enhance removal of resident cells. Additional steps could be taken to eliminate any residual detergents or enzymes in the tissue matrix, so as to avoid interference with the later repopulating of the implant with viable cells. A similar approach is described in US pub. No. 2008/0131966, which is incorporated by reference.

In another embodiment, the device is removed from the site of the implant. The devices can be removed by any method known in the art. In order to aid in removal, the device may have a small length of wire or small lip that would allow the mechanical removal of the device without damaging the device. The device may be partially or completely removed for retrieving the cells.

After removal of the device, the trapped cells can be retrieved by any method known in the art, such as by digesting the cell attachments to the porous matrix. This can be achieved by, for example, flowing a trypsin containing buffer through the device. The trapped cells can then be expelled from the device by any method known in the art. In a preferred embodiment, the device contains an outlet covered by a membrane which can be burst, for example, by the application of positive pressure through the device, allowing the expulsion of the trapped cells from the device. Alternatively, the porous matrix with the trapped cells can be expelled from the device and the trapped cells can then be separated from the porous membrane by any method known in the art. In a preferred embodiment, the device contains an outlet covered by a membrane which can be burst, for example, by the application of positive pressure through the device, allowing the expulsion of the porous matrix with the trapped cells from the device.

Once the trapped cells have been retrieved from the device, trapped cells of interest can be separated from the other trapped cells. This can be done by any means known in the art such as, for example, combining the trapped cells with microbeads with a binding partner to a surface marker present on the other trapped cells but not the trapped cells of interest. Removing the microbeads with the bound other trapped cells leaves only the trapped cells of interest. In another embodiment, the trapped cells of interest can be separated from the other trapped cells by combining the trapped cells with microbeads with a binding partner to a surface marker present on the trapped cells of interest but not the other trapped cells. The trapped cells of interest bind to the microbeads and can be removed. For example, T-cells may be removed by using binding partners that specifically bind to T-cell surface receptors or markers but not to B-cell, dendritic cells, or macrophages.

Alternately, a binding partner capable of binding to the other infiltrating cells but not the cells of interest, which binding partners are capable of being bound (covalently or noncovalently) to a microbead may be used. For example, such binding partners can include aptamers, or preferably antibodies or antibody fragments, where the binding site is preferably specific for a cell surface marker present on the surface of such infiltrating cells but not the cells of interest. Alternately, a reverse approach of using binding partners that are specific for cells of interest may be used. For example, when the trapped cells of interest are macrophages, a preferred microbead has antibodies specific for macrophage-specific cell surface receptors. The skilled artisan could formulate a binding partner for any particular cell of interest or a combination thereof.

Aptamers are single stranded oligonucleotides or oligonucleotide analogs that bind to a particular target molecule, such as a protein or small molecule. Thus, aptamers are the oligonucleotide analogs of antibodies. Both RNA and single-stranded DNA, or DNA analog, aptamers are known. Aptamers that bind to virtually any particular target can be selected by using an iterative process called SELEX (Systematic Evolution of Ligands by EXponential enrichment).

An antibody or antibody fragments can be polyclonal, monoclonal, or recombinant and can be of any animal, such as a rodent or a human, or a mixture of animals, such as humanized mouse.

Any type of microbead can be used to bind the other trapped cells. For example, the microbeads can be heavy particles that are pelleted under centrifugal conditions, but which do not pellet the trapped cells of interest. Alternatively, the microbeads can be buoyant particles that are not pelleted under centrifugal conditions that pellet the trapped cells of interest. In a preferred embodiment, the microbeads are magnetic beads.

The isolated cells may be subjected to further analysis. Such further analysis may include quantification of the cells, or analysis of mRNA or protein expression. For example, the trapped cells of interest can be quantified, in order to approximate the number of trapped cells of interest in a given amount of tissue, in order to compare the number of trapped cells of interest to the amount of the other trapped cells. The trapped cells of interest can be quantified by any method known in the art, such as by microscopic observation.

Preferably, the trapped cells are separated and/or sorted for analysis using cytometric techniques, e.g., fluorescence-activated cell sorting (FACS). This may be accomplished using a plurality of antibodies or other binding molecules described above and other secondary agents. The trapped cells may be phenotyped using art known methods. See, Autissier et al., J Immunol Methods. 360(1-2): 119-128 (2010). For example, T cells are characterized by or identified by cell surface markers such as CD4 or CD8. Dendritic cells are characterized by or identified by expression of CD11c. Macrophages are characterized by or identified by expression of CD11c and/or CD68. Exemplary markers (both to positively identify and also to exclude other cells) include CD11c (to select for DCs), Gr-1 (to select for macrophages), CD204 (to select for macrophages), CD16 (to select for monocytes and to negatively select for (e.g., exclude) non-monocyte cells, i.e., cells that do not have a monocyte phenotype or cell surface marker phenotype), CD45 (to select for hematopoetic cells, e.g., immune cells), CD49b [to select for natural killer (NK cells) as well as a subset of T cells that express this marker], CD3 (to select for T cells), CD4 (T-cells), CD8 (T-cells), CD19 and B220.

In some preferred embodiments, mRNA or protein expression is determined in the trapped cells of interest. For example, T cell and B cell receptors of trapped cells may be sequenced to identify the antigen-specificity of disease and drug targets for autoimmunity. In related embodiments, the mRNA or protein expression of the trapped cells of interest may then be compared to the expression of the same gene or genes in other cell types or identical cells from other subjects. When analysis of mRNA or protein expression of more than one gene is desired, microarray technology can be employed. This well-established technology can analyze mRNA or protein expression patterns of many genes at once, allowing comparison between, for example, an entire genome of trapped cells of interest and other cells. In the event that the amount of biological material recovered from the devices is insufficient for analysis, mRNA from the trapped cells of interest can be amplified prior to determination of gene expression. Such amplification can be done by any method known in the art, such as by reverse transcription and cDNA amplification.

Antigen-Specific Cells

In some embodiments, the antigen-specific trapped cells or a sub-population thereof (e.g., antigen-specific T cells or B-cells) are manipulated for formulating compositions that are suitable for diagnostic or therapeutic use. Examples of manipulation include, for example, activation, division, differentiation, growth, expansion, reprogramming, anergy, quiescence, senescence, apoptosis or death. The cells need not be physically removed from the device to be manipulated. Thus, in one embodiment, the cells are manipulated in situ (e.g., at or near the implant site). In other embodiments, the cells are manipulated ex situ (e.g., at a site that is different from the implant site).

In some embodiments, the antigen-specific cells, e.g., T-cells, are manipulated (e.g., activated and/or expanded) in situ by providing devices containing a plurality of antigens optionally together with antigen-presenting cells (or antigens which attract such APCs). In other embodiments, the antigen-specific cells are manipulated in cell culture by incubation with the antigen (e.g., autoimmune antigen) optionally together with an antigen-presenting cell. Once activated, cells undergo a complex cascade of cell signaling which leads to the transcription and expression of many gene products. The gene products specific for activated cells may be analyzed further for identifying and isolating cells with desired antigen specificity.

(a) T-Cell

Embodiments described herein are directed to a method for manipulating antigen-specific T cells ex situ. It is noted that the technique described herein can be varied for carrying out the process in situ. A sample comprising T cells is incubated with a particular antigen, which causes the activation of a T cell specific for the antigen of interest. The T-cell containing sample may be incubated with the antigen for about 1 day to 7 days. Antigen-specific T-cells are then be isolated by selecting for T cells that express gene products of T cells activated as described above. The antigen of interest could be a self-antigen or a non-self antigen or a fragment thereof. The antigen of interest may also be a combination of two or more individual antigens of interest.

The gene product for identifying or negatively selecting for activated T cells may be a cell surface marker or cytokine, or a combination thereof. Cell surface markers for identifying activated T cells include, but are not limited to, CD69, CD4, CD8, CD25, HLA-DR, CD28, and CD134. CD69 is an early activation marker found on B and T lymphocytes, NK cells and granulocytes. CD25 is an IL-2 receptor and is a marker for activated T cells and B cells. CD4 is a TCR coreceptor and is marker for thymoctes, TH1- and TH2-type T cells, monocytes, and macrophages. CD8 is also a TCR coreceptor and is marker for cytotoxic T cells. CD134 is expressed only in activated CD4+ T cells.

Cell surface markers for negatively selecting for activated T cells include, but are not limited to, CD36, CD40, and CD44. CD28 acts as a stimulatory T-cell activation pathway independent of the T-cell receptor pathway and is expressed on CD4+ and CD8+ cells. CD36 is a membrane glycoprotein and is a marker for platelets, monocytes and endothelial cells. CD40 is a marker for B cells, macrophages and dendritic cells. CD44 is a marker for macrophages and other phagocytic cells. Subsets of T cells may be isolated by using positive selection, negative selection, or a combination thereof for expression of cell surface gene products of helper T cells or cytotoxic T cells (e.g., CD4 vs. CD8). Cytokines for identifying activated T cells of the present invention include, but are not limited to cytokines produced by TH1-type T cells (cell-mediated response) and TH2-type T cells (antibody response). Cytokines for identifying activated TH1-type T cells include, but are not limited to, IL-2, gamma interferon (γIFN) and tissue necrosis factor alpha (TNFα). Cytokines for identifying activated TH2-type T cells include, but not limited to, IL-4, IL-5, IL-10 and IL-13. Subsets of T cells may also be isolated by using positive selection, negative selection, or a combination thereof for expression of cytokine gene products of helper T cells or cytotoxic T cells (e.g., γIFN vs. IL4).

An activated TH1-type T cell specific for an antigen of interest may be isolated by identifying cells that express CD69, CD4, CD25, IL-2, IFNγ, TNFα, or a combination thereof. An activated TH1-type T cell specific for an antigen of interest may also be isolated by identifying cells that express CD69 and CD4 together with IFNγ or TNFα. An activated TH2-type T cell specific for an antigen of interest may be isolated by identifying cells that express CD69, CD4, IL-4, IL-5, IL-10, IL-13, or a combination thereof. A combination of an activated TH1-type T cell and a TH2-type T cell specific for an antigen of interest may be isolated by identifying cells that express CD69, CD4, CD25, IL-2, IFNγ, TNFα, or a combination thereof and cells that express CD69, CD4, IL-4, IL-5, IL-10, IL-13, or a combination thereof.

The gene products used for positive or negative selection of the activated T cells of the present invention may be identified by immunoselection techniques known to those in the art which utilize antibodies including, but not limited to, fluorescence activated cell sorting (FACS), magnetic cell sorting, panning, and chromatography. Immunoselection of two or more markers on activated T cells may be performed in one or more steps, wherein each step positively or negatively selects for one or more markers. When immunoselection of two or more markers is performed in one step using FACS, the two or more different antibodies may be labeled with different fluorophores. Alternately, as described above, cells may be sorted using microbeads.

For cell-surface expressed gene products, the antibody may directly bind to the gene product and may be used for cell selection. For cell-surface gene products expressed at low concentrations, magnetofluorescent liposomes may be used for cell selection. At low levels of expression, conventional fluorescently labeled antibodies may not be sensitive enough to detect the presence of the cell surface expressed gene product. Fluorophore-containing liposomes may be conjugated to antibodies with the specificity of interest, thereby allowing detection of the cell surface markers.

For intracellular gene products, such as cytokines, the antibody may be used after permeabilizing the cells. Alternatively, to avoid killing the cells by permeabilization, the intracellular gene product if it is ultimately secreted from the cell may be detected as it is secreted through the cell membrane using a "catch" antibody on the cell surface. The catch antibody may be a double antibody that is specific for two different antigens: (i) the secreted gene product of interest and (ii) a cell surface protein. The cell surface protein may be any surface marker present on T cells, in particular, or lymphocytes, in general, (e.g., CD45). The catch antibody may first bind to the cell surface protein and then bind to the intracellular gene product of interest as it is secreted through the membrane, thereby retaining the gene product on the cell surface. A labeled antibody specific for the captured gene product may then be used to bind to the captured gene product, which allows the selection of the activated T cell. Certain forms of cytokines are also found expressed at low concentration on the cell surface. For example, γIFN is displayed at a low concentration on the cell surface with kinetics similar to those of intracellular γIFN expression (Assenmacher, et al. Eur J. Immunol, 1996, 26:263-267). For forms of cytokines expressed on the cell surface, conventional fluorescently labeled antibodies or fluorophore containing liposomes may be used for detecting the cytokine of interest. One of ordinary skill in the art will recognize other techniques for detecting and selecting extracellular and intracellular gene products specific for activated T cells.

The T cells isolated by the present invention may be enriched by at least 40%-90% from whole blood. The T cells may also be enriched by at least 95% from whole blood. The T cells may also be enriched by at least 98% from whole blood. The T cells may also be enriched at least 99.5% from whole blood. Similar methods may be used in the in situ or ex situ manipulation of B-cells.

(b) B-Cells

Antigen specific B-cells may be obtained using slight variations to the aforementioned methods. For example, DYNABEAD-M-450 can be used to couple disease specific antigens, which are then incubated with a composition containing the cells trapped with the devices of the invention. Optionally, the trapped cells may be subjected to a screening process to enrich the sample, e.g., using agents that bind to cell surface markers that are specific for B-cells. The B-cells are then incubated with the antigen-coupled DYNABEADS and cultured for a period of about 7-10 days to generate rosette cells. The rosette cells are optionally typed by analyzing the secreted antibodies, e.g., based on their ability to bind to the disease specific antigens. Clones that are identified as positives may be transformed to produce hybridomas using routine techniques.

Embodiments described herein further relate to isolated cells that are specific for an antigen of interest, which cells are isolated by the method describeds above. The isolated cells may be monoclonal cells or polyclonal antigen-specific immune cells, e.g. antigen-specific T-cells.

Embodiments of the invention further relate to methods of determining the relative frequency of antigen-specific immune cells by determining the number of immune cells trapped in the devices of the present invention. Preferably, the antigen-specific immune cells are T-cells or B-cells. Particularly preferably, the antigen-specific immune cells are T-cells.

Diagnosis of Disease/Disorders

Embodiments described herein further relate to methods for detecting or diagnosing a disease or a disorder in a subject. In one embodiment, the disease is cancer. In another embodiment, the disease is an autoimmune disorder. In a third embodiment, the disease is a pathogenic disease.

In these embodiments, a subject with a disease may be diagnosed by first administering a device of the invention to the subject, wherein the antigens in the device are specific to the disease. The devices are then allowed to remain in the subject for a period, e.g., 0.5 day, 1 day, 2 days, 5 days, 7 days, 14 days, 25 days, 30 days, 35 days, 38 days, 45 days, 50 days, 60 days or more and the cells contained therein are analyzed using one or more of the aforementioned techniques. For example, in the context of autoimmune diseases, the cells that are analyzed may include T-cells, B-cells, antigen presenting cells, or a combination thereof. In the context of cancer diagnosis, the cells that are analyzed my include T-cells or B-cells. In the context of pathogenic diseases, the cells that are analyzed may include antigen presenting cells.

The analytical step may be carried out using any routine methods. Accordingly, in one embodiment, the analytical step may involve determining the number of immune cells that are specific to the autoimmune disease. Any routine technique may be used to determine antigen-binding specificity of immune cells, e.g., loading cell samples onto antigen-coated surfaces, washing away non-specifically bound cells, and quantitating the number of antigen-specific cells (either in free form by releasing the bound cells or in bound form) using a detection agent (e.g., an antibody that binds to a cell-surface epitope located on the antigen-specific cells). In another embodiment, the analytical step may involve determining the physical or biological characteristics of the antigen-specific immune cells. Examples of physical characteristics include, for example, size, shape, reflectivity, morphology, density. Examples of biological characteristics include, for example, expression of particular cell surface markers, secretion of cytokines, reactivity to particular antigens or agents, patterns of gene expression.

The analytical step may be tied to a correlation step, wherein, the results of the analytical step are correlated to the parameter of interest. Representative types of parameters include, presence (or absence of disease), type of disease (e.g., aggressive vs. non-aggressive autoimmune disorder; druggable vs. non-druggable disease, e.g., antibiotic susceptible vs. antibiotic resistant bacterial infection, immunotherapy-resistant vs immunotherapy-sensitive cancer), stage of disease, progression/regression of disease (over time), etc. In one embodiment, the parameter relates to presence or absence of disease (which can be expressed in binary terms). In another embodiment, the parameter relates to staging of disease (which can be expressed in a nominal scale, e.g., stage I-IV, with stage IV being the highest). Yet in another embodiment, the parameter relates to odds or likelihood of occurrence of the disease, e.g., least 20%, 30%, 40%, 50%, 60%, 70%, 80%, 2-fold, 3-fold, 5-fold, 10-fold, 20-fold or more.

In the aforementioned diagnostic methods the parameters may be compared to a baseline value. The baseline value may be a value that is pre-determined, e.g., in a population of healthy subjects. For example, where the antigen of interest is rheumatoid arthritis (RA) antigen, a baseline level of RA-specific antibodies (or T-cells) in healthy subjects may be used in the correlation step. Alternately, the baseline value may be experimentally identified using suitable controls, e.g., devices that only contain scaffolds (i.e., negative for antigen, recruitment agent, or both) or devices that contain random or non-disease specific antigens. The skilled worker can use routine techniques to correlate and/or draw inferences between various subject groups.

For example, in one embodiment, devices containing disease-specific antigens (e.g., MBP70 derived from *Mycobacterium bovis*) are implanted into a group of subjects that are suspected to have been exposed to the pathogen and a group of healthy (or random) subjects for a given time period (e.g., two weeks). Separately, a small number of subjects in each group are provided with control devices (containing random or non-MBP antigens). The devices are explanted and the number of antigen-specific T-cells in the experimental group (e.g., suspect group implanted with the MBP70+ device) and the control groups are measured and compared. Positive diagnosis is made if more (e.g., at statistical significance) antigen-specific T-cells are detected in devices recovered from the suspect group than those recovered from the control group(s). Additionally, depending on the diagnosis, the suspect group may be treated with a therapeutic agent. The number of antigen-specific T-cells in treated subjects may be compared over time and also compared to those present in healthy subjects. Based on the results, the researcher could make inferences on the effectiveness of the therapy and also monitor therapeutic progress/regression of the disease over time. A similar protocol may be used in the diagnosis, monitoring and management of cancer patients and subjects suffering from autoimmune diseases.

The subject is an animal, preferably a mammal or a bird. Particularly preferably, the subject is selected from the group consisting of humans, dogs, cats, pigs, cows, buffalo and horses. Most preferably, the subject is a human.

Any immune cell may be used in the diagnosis of the disease or disorder. Preferably, diagnosis is performed with a lymphocyte, e.g., T-cells, B-cells, dendritic cells or APCs, e.g., macrophages, or a combination thereof. It is especially preferable to use T-cells in the diagnosis.

Any disease or disorder may be detected or diagnosed using the aforementioned methods. Particularly preferably, the disease is an autoimmune disease selected from the group consisting of rheumatoid arthritis, lupus, celiac disease, inflammatory bowel disease or Crohn's disease, sjögren's syndrome polymyalgia rheumatic, multiple sclerosis, ankylosing spondylitis, Type 1 diabetes, alopecia areata, vasculitis, temporal arteritis, etc. In other embodiments, the disease is a cancer which is selected from the group consisting of head and neck cancer, breast cancer, pancreatic cancer, prostate cancer, renal cancer, esophageal cancer, bone cancer, testicular cancer, cervical cancer, gastrointestinal cancer, glioblastoma, leukemia, lymphoma, mantle cell lymphoma, pre-neoplastic lesions in the lung, colon cancer, melanoma, and bladder cancer.

In yet another embodiment, the disease is a pathogenic disease selected from the group consisting of a bacterial disease, a viral disease and a fungal disease or a combination thereof.

Accordingly, embodiments of the invention relate to detecting or diagnosing autoimmune disease, cancer, or a pathogenic disease in a subject by administering the device of the invention containing antigens which are specific to the autoimmune disease, cancer disease, or pathogenic disease, and analyzing the immune cells contained therein. The devices may be optionally explanted to recover the immune cells. It may be possible to carry out the detection/analytical step in situ.

Related embodiments are directed to methods of monitoring the progression of a disease in a subject. The method comprises administering, to a subject, the devices of the invention containing antigens that are specific to the disease and analyzing the immune cells contained therein. The number/types of immune cells trapped in the device may offer valuable cues as to the progression of the disease. Alternately, wherein the subject has undergone therapeutic intervention, analogous methods may be used to monitor the therapy of disease and/or disease management.

The aforementioned methods may be used to monitor the progression/therapy of autoimmune disorders, cancers, pathogenic diseases, and the like. Preferably, the immune cells that are used in the diagnostic methods are T-cells or B-cells.

In the context of autoimmune disorders, the progression of the disease may be monitored by analyzing the number and/or type of autoreactive T cells. Depending on the result of the analysis, methods of intervention and/therapy may be designed to minimize the severity of the symptoms. In other instances, preventive methods may be undertaken, including providing recommendations to subjects on dietary, nutritional and/or other lifestyle changes.

Production of Novel Compositions and Vaccines for the Therapy of Diseases

Embodiments described herein further relate to methods for devising and producing novel compositions for treating a disease. The method comprises administering the devices of the invention containing disease specific antigens to a subject, which then trap immune cells that are specific to the disease, optionally isolating, enriching, and expanding the immune cells trapped in the device, and then administering the immune cells back to the subject. Alternately, products derived from such immune cells may be administered to the subjects. Examples of products derived from the immune cells include, nucleic acids (including vectors and cells containing such nucleic acids), peptides, proteins, antibodies, cytokines, etc.

Preferably, the disease is an autoimmune disease. Under this embodiment, autoreactive T cells which have been isolated (and optionally expanded in culture as described herein) by the aforementioned methods may be inactivated in situ or ex situ. Methods of inactivating T cells are known in the art. Examples include, but not limited to, chemical inactivation or irradiation. The autoreactive T cells may be preserved either before or after inactivation using a number of techniques known to those skilled in the art including, but not limited to, cryopreservation. As described below, the composition may be used as a vaccine to deplete autoreactive T cells in autoimmune patients.

In one embodiment, the vaccine may comprise autoreactive T cells comprising homogeneous ("monoclonal") or heterogeneous ("polyclonal") patterns of Vβ-Dβ-Jβ gene usage. Clinical studies indicate that autoimmune patients receiving autologous monoclonal T cell vaccination may show a gradual decline in the immunity against autoreactive T cells. In some cases, the reappearing autoreactive T cells may originate from different clonal populations, suggesting that the T cells may undergo clonal shift or epitope spreading potentially associated with the ongoing disease process. Clonal shift or epitope spreading may be a problem in autoimmune diseases mediated by autoreactive T cells. A vaccine comprising polyclonal autoreactive T cells capable of depleting multiple populations of autoreactive T cells may avoid problems with clonal shift or epitope spreading.

Embodiments described herein further relate to compositions and vaccines produced by the aforementioned methods. The composition may be a pharmaceutical composition, which may be produced using methods well known in the art. Pharmaceutical compositions used as preclinical and clinical therapeutics in the treatment of disease or disorders may be produced by those of skill, employing accepted principles of diagnosis and treatment.

Therapy of Disease

Embodiments described herein further relate to methods for treating a disease or a disorder in a subject. In one embodiment, the disease is cancer. In another embodiment, the disease is an autoimmune disorder. In a third embodiment, the disease is a pathogenic disease.

In these embodiments, a subject with a disease may be treated by first administering a device of the invention to the subject, wherein the antigens in the device are specific to the disease. The devices are then allowed to remain in the subject for a period, e.g., 0.5 day, 1 day, 2 days, 5 days, 7 days, 14 days, 25 days, 30 days, 35 days, 38 days, 45 days, 50 days, 60 days or more, and the cells contained therein are manipulated using one or more of the aforementioned techniques. For example, in the context of autoimmune diseases, the cells that are manipulated may include T-cells, B-cells, antigen presenting cells, or a combination thereof. In the context of cancer treatment, the cells that are manipulated may include T-cells or B-cells. In the context of pathogenic diseases, the cells that are manipulated may include antigen presenting cells. Examples of manipulation include, for example, activation, division, differentiation, growth, expansion, reprogramming, anergy, quiescence, senescence, apoptosis, death, etc. The cells need not be physically removed from the device to be manipulated. Thus in one embodiment, the cells are manipulated in situ (e.g., at or near the implant site). In other embodiments, the cells are manipulated ex situ (e.g., at a site that is different from the implant site).

Accordingly, embodiments of the instant invention provide for methods for treating cancer in a subject. The method comprises administering a device of the instant invention to a subject, wherein the plurality of antigens are specific for the cancer, collecting a plurality of immune cells trapped in the device, wherein the plurality of immune cells are specific to the plurality of antigens, and administering the plurality of immune cells or products derived therefrom into the subject, thereby treating the cancer.

Representative examples of cancer antigens include, but are not limited to, MAGE-1, MAGE-2, MAGE-3, CEA, Tyrosinase, midkin, BAGE, CASP-8, β-catenin, β-catenin, γ-catenin, CA-125, CDK-1, CDK4, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf 112, SART1, SART2, SART3, BRAP, RTN4, GLEA2, TNKS2, KIAA0376, ING4, HSPH1, Cl3orf24, RBPSUH, C6orfi53, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Glil, Cav-1, cathepsin B, CD74, E-cadherin, EphA2/Eck, Fra-1/Fosl 1, GAGE-1, Ganglioside/GD2, GnT-V, β1,6-N, Ki67, Ku70/80, PROX1, PSCA, SOX10, SOX11, Survivin, UPAR, WT-1, Dipeptidyl peptidase IV (DPPIV), adenosine deaminase-binding protein (AD Abp), cyclophilin b, Colorectal associated antigen (CRC)-C017-1A/GA733, T-cell receptor/CD3-zeta chain, GAGE-family of tumor antigens, RAGE, LAGE-I, NAG, GnT-V, RCAS1, α-fetoprotein, p120ctn, Pmel117, PRAME, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, HA, Connexin 37, Ig-idiotype, p15, GM2, GD2 gangliosides, Smad family of tumor antigens, lmp-1, EBV-encoded nuclear antigen (EBNA)-I, UL16-binding protein-like transcript 1 (Multi), RAE-1 proteins, H60, MICA, MICB, and c-erbB-2, or an immunogenic peptide thereof, and combinations thereof.

Preferably, the immune cells are T-cells or B-cells which bind with specificity to one or more of the aforementioned antigens. Cell products that are useful in practicing the cancer therapy methods of the instant invention include, for example, hybridomas of B-cells, stable lineages of T-cells, antibodies derived from B-cells or hybridomas thereof, receptors which bind to the cancer antigens (receptors which bind to MHC molecules presenting the antigens), including fragments thereof, nucleic acids encoding the receptors or antigen-binding domains thereof, nucleic acids encoding antibodies, including whole cells.

Embodiments of the instant invention provide for methods for treating a pathogenic disease in a subject. The method comprises administering a device of the instant invention to a subject, wherein the plurality of antigens are specific for the pathogenic disease, collecting a plurality of immune cells trapped in the device, wherein the plurality of immune cells are specific to the plurality of antigens, and administering the plurality of immune cells or products derived therefrom into the subject, thereby treating the pathogenic disease. In some instances, the immune cells or compositions derived therefrom may be administered prophylactically, e.g., before the onset of the disease symptoms in the subject.

Pathogenic diseases that may be treated in accordance with the aforementioned embodiment include, bacterial diseases, viral diseases, fungal diseases, or a combination thereof.

Cell products that are useful in treating pathogenic diseases of the instant invention include, for example, hybridomas of B-cells, stable lineages of T-cells, antibodies derived from B-cells or hybridomas thereof, receptors which bind to the pathogenic antigens (and/or receptors which bind to MHC molecules presenting the pathogenic antigens), fragments of such antibodies or receptors, nucleic acids encoding the receptors, antibodies, or antigen-binding domains thereof, including whole cells.

Embodiments of the instant invention provide for methods for treating an autoimmune disease in a subject. The method comprises administering a device of the instant invention to a subject, wherein the plurality of antigens are specific for the autoimmune disease, collecting a plurality of immune cells trapped in the device, wherein the plurality of immune cells are specific to the plurality of antigens, and administering the plurality of immune cells or regulators thereof into the subject, thereby treating the autoimmune disease.

In the context of autoimmune diseases, it may be preferable not to administer active immune cells (as these are autoreactive) but rather quiescent, senescent or inactivated immune cells. Preferably, the immune cells are T-cells. Alternately, regulators of immune cells may be administered. Such may include, for example, suppressor T cells or regulatory T cells. Accordingly, in some embodiments, the invention provides for a method for treating autoimmune disease by administering to subject in need thereof, the device of the invention, wherein the plurality of antigens in the device are specific for the autoimmune disease, collecting a plurality of regulatory or suppressor T-cells trapped in the device, wherein the plurality of regulatory or suppressor T-cells are specific to the antigens, and administering the plurality of regulatory T-cells or suppressor T-cells or products derived therefrom into the subject, thereby treating the autoimmune disease.

Cell products that are useful in practicing the therapy of autoimmune diseases include, for example, antibodies and receptors which bind to autoreactive cells, regulatory proteins located in suppressor or regulatory T-cells, including nucleic acid sequences which encode such molecules.

In the therapeutic embodiments described above, cells may be formulated at total cell concentrations including from about $5\times10^2$ cells/ml to about $1\times10^9$ cells/ml. Preferred doses of T cells range from about $2\times10^6$ cells to about $9\times10^7$ cells.

Embodiments of the instant invention further relate to therapy of diseases by administering one or more of the aforementioned compositions. The composition may be a pharmaceutical composition, which is administered by any means that achieve their intended purpose. For example, administration may be by parenteral, subcutaneous, intravenous, intraarterial, intradermal, intramuscular, intraperitoneal, transdermal, transmucosal, intracerebral, intrathecal, or intraventricular routes. Alternatively, or concurrently, administration may be by the oral route. The pharmaceutical compositions may be administered parenterally by bolus injection or by gradual perfusion over time.

The dosage administered may be dependent upon the age, sex, health, and weight of the recipient, kind of concurrent treatment, if any, frequency of treatment, and the nature of the effect desired. The dose ranges for the administration of the pharmaceutical compositions may be large enough to produce the desired effect, whereby, for example, autoreactive T cells are depleted and/or the autoimmune disease is significantly prevented, suppressed, or treated. The doses may not be so large as to cause adverse side effects, such as unwanted cross reactions, generalized immunosuppression, anaphylactic reactions and the like.

Determination of Repertoire of Immune Cells Associated with a Disease

Embodiments disclosed herein further relate to methods for determining the repertoire of nucleic acids encoding one or more immune cell receptors, or a portion thereof, in a subject suffering from a disease. The methods comprise amplifying nucleic acids encoding one or more immune cell receptors obtained from cells trapped by the devices of the instant invention. Preferably, the immune cells are T-cells or B-cells and the immune cell receptors are T-cell receptors (TCR) and B-cell receptors (BCR), respectively. Methods for targeting and amplifying targeted nucleic acid constructs from whole cell lysates are known in the art. See, Maryanski et al., Immunity, Vol. 4, Pages 47-55, 1996, which is incorporated by reference.

In these embodiments, the subject is suffering from an autoimmune disease such as type I diabetes, Multiple Sclerosis, rheumatoid arthritis (RA), inflammatory bowel disease (IBD) or Crohn's Disease (CD), or and other gastrointestinal autoimmune conditions. The population of cells collected from the devices may be further selected with various antigens associated with the aforementioned diseases and repertoire of immune cells selected via antigen priming may be characterized based on the sequences of cell-surface receptors expressed therein. In one representative method, the immune cells are T-cells and are characterized based on the sequences of T-cell receptors involved in binding to the disease antigen, e.g., an antigen associated with T1D.

Trapping of Cells for Analysis of Pathogens and/or Various Strains Thereof

The immune system uses a variety of players for detecting and removing pathogens from the body. For example, pathogens may be taken up by macrophages, which digest and process them to present them on cell-surface major histocompatibility complex (MHC) molecules, allowing for lymphocytes to recognize them. Accordingly, embodiments of the instant invention provide for detecting and analyzing pathogens via analysis of the immune cells that are specific to the pathogens. The pathogen may be a bacterium, a virus, a fungus, or a combination thereof.

Thus, in accordance with the aforementioned embodiment, the instant invention provides for traps which recruit immune cells, e.g., T-cells, B-cells, macrophages or dendritic cells, which immune cells are specific for the pathogen of interest. In particular, the immune cells are T-cells or B-cells which bind to pathogenic antigens. Alternately, the immune cells are antigen presenting cells such as dendritic cells or macrophages. In these embodiments, the devices containing a plurality of antigens that are specific to a pathogen are administered into a subject for a period (e.g., 1 week to 3 weeks) and immune cells contained therein are analyzed for specificity and/or binding to the pathogenic antigen. The cells may be further divided into distinct sub-populations based on their reactivity to particular epitopes contained in the antigen. Optionally, the cells may be formulated into immune compositions for the therapy of pathogenic diseases. Preferably, the immune composition is a dendritic cell composition.

A representative list of pathogens and pathogenic antigens, including NCBI/GI accession numbers thereof, are provided in Table 6.

In a related embodiment, the instant invention provides for devices for trapping immune cells that are specific to new bacterial antigens. For example, MPB70 and MPB83 have been well-studied and generally well-understood in the context of mycobacteria. However, because they are less abundantly expressed in *M. tuberculosis* (more highly expressed in *Mycobacterium bovis*), their involvement in pathogenicity of *M. tuberculosis* is not well-understood. The devices of the instant invention may be implemented to identify new/key pathogenic antigens in related strains which can be specifically targeted by immune cells and/or their products. For example, devices containing MPB70 and MPB83 proteins derived from *Mycobacterium bovis* can be implanted into subjects to isolate a population of immune cells which can be tested for cross-reactivity to *M. tuberculosis*. The immune cells that cross-react can be typed for determining receptors and molecules involved in cross-reactivity. Thus, novel targets and therapeutic agents binding thereto can be identified.

TABLE 6

Various types of pathogens, exemplary forms of pathogenic antigens and their corresponding NCBI and GI accession numbers:

| Pathogen | Antigens | Accession Nos. of antigens |
| --- | --- | --- |
| *Mycobacterium bovis* | MPB70 | D38230.1 GI:1008918 |
| | MPB83 | EU683972.1 GI:188523816 |
| | MPB64 | |
| | MPB80 | |
| Human Papilloma virus (HPV) | E2 | AF115832.1 GI:5257208 |
| | E6 | KC190291.1 GI:425892430 |
| | E7 | JX896422.1 GI:414090986 |
| Human immunodeficiency virus | p17 | AJ294941.1 GI:10800847 |
| | Gag p24 | ACI05538.1 GI:206129896 |
| Methicillin-resistant *Staphylococcus aureus* | PBP2a | KF895401.1 GI:586616552 |

VIII. Kits

In certain embodiments, the present invention provides kits comprising, in one or separate compartments, the devices of the instant invention. The kits may further comprise additional ingredients, e.g., gelling agents, emollients, surfactants, humectants, viscosity enhancers, emulsifiers in one or more compartments. The kits may optionally comprise instructions for formulating the devices for diagnostic or therapeutic applications. The kits may also comprise instructions for using the components, either individually or together, in the therapy or diagnosis of various disorders and/or diseases.

In a related embodiment, the present invention provides kits comprising the devices of the invention along with reagents for selecting, culturing, expanding, sustaining, and/or transplanting the trapped cells of interest. Representative examples of cell selection kits, culture kits, expansion kits, transplantation kits for T-cells, B-cells and antigen presenting cells are known in the art. For example, where the target cells of interest are B-cells, such may be initially sorted using DYNABEADS, MACS-beads (Miltenyi Biosciences), maintained in ROSETTESEP culture media (Stem Cell Technologies) and expanded with CELLEXVIVO Human B Cell Expansion Kit (R&D Systems). The cells may be enriched in the sample by using centrifugation techniques known to those in the art including, but not limited to, FICOLL® gradients. Cells may also be enriched in the sample by using positive selection, negative selection, or a combination thereof for expression of gene products thereof.

This invention is further illustrated by the following examples which should not be construed as limiting. The entire contents of all references, patents and published patent applications cited throughout this application, as well as the Figures and the Sequence Listing, are hereby incorporated herein by reference.

EXAMPLES

Example 1: Device Fabrication and Characterization

In accordance with the aforementioned methods, polymeric scaffolds for the devices were engineered to sustain antigen presentation. In short, device fabrication was carried out as follows: Copolymers of lactide and glycolide (PLG) (Alkermes, Cambridge, Mass.) were utilized in a gas-foaming process to form PLG scaffolds. To physically adsorb antigen onto PLG polymer, a gas foaming particulate leaching was used to fabricate scaffolds to be used as traps. FIG. 1A shows a photomicrograph of the cross-sectional scanning electron microscope (SEM) images of a model device made with PLG (the picture on the right shows displays an enlarged view of the pores). Alternatively, other polymers such as alginate may be used as the structural element of the devices. The pores allow space for T cell infiltration and expansion. FIG. 1B shows that OVA-T cell traps are capable of releasing ovalbumin (OVA) protein (model antigen).

The devices were further implanted subcutaneously in the backs of mice for a period of 14 days. FIG. 1C is a bar graph showing the local cytokine concentration of MIP-la and RANTES at site of implantation. The values in B and C represent the average and standard deviation (n=5). It can be seen that compared to controls, local cytokine concentration for each cytokine was significantly higher at the site of implantation of the traps. Normally, antigen-specific T cells have the ability to enter into inflamed tissues presenting the corresponding antigen and proliferating upon T cell receptor (TCR)-antigen recognition. When T cell traps displaying antigens are administered subcutaneously, they promote local MIP-la and RANTES production, which are similar to sites of inflammation and autoimmune lesions. Traps contain an antigen (or mixture of antigens) that engages a specific TCR on the T cell to become sticky and remain in device. This antigen interaction also causes T cells to proliferate within the device, thereby enriching the local area with these cells.

Example 2: Implantation of Devices

Figure 2A:
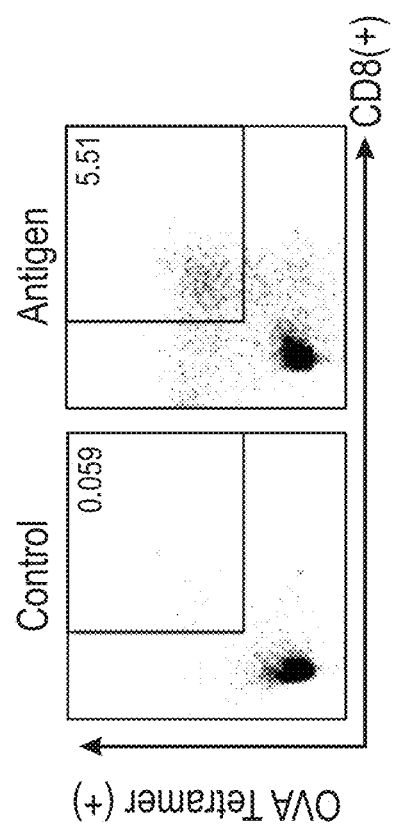
FIG. 2A is a series of fluorescence activated cell sorting (FACS) plots of cells isolated from control (Control) and ovalbumin (OVA; Antigen) loaded traps. Cells were stained with anti-CD8 and OVA class I tetramers. The gates represent the OVA-specific, CD8(+) T cells and numbers provide the percentage of positive cells. Traps were implanted into OT-1 mice for 14 days.

Traps loaded with the model antigen, ovalbumin (OVA), and control traps were implanted into OT-1 mice that have a pre-existing pool of OVA-specific T cells. After 14 days, the scaffolds were explanted and cells harvested and stained for CD8 and OVA tetramer. Traps containing OVA were enriched for OVA-specific T cells (FIG. 2A) and had approximately 5-8 fold more T cells relative to controls (FIG. 2B). When two different traps containing a unique antigen mix, either for OVA or melanoma antigens, were implanted into mice, T cells accumulated preferentially in traps loaded with the cognate antigen (FIG. 2C). OVA specific T cells accumulated significantly in OVA traps, whereas Trp2 (melanoma antigen) specific T cells accumulated significantly in melanoma traps (FIG. 2C and FIG. 2D). The OVA and melanoma specific cells were essentially absent in traps not containing the corresponding antigen (FIG. 2C and FIG. 2D).

Example 3: Trapping of T Cells During Diabetes Progression

Figure 3A:
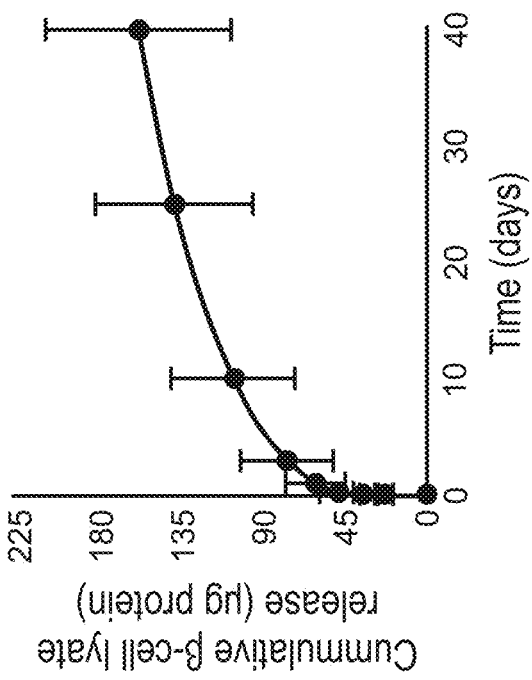
FIG. 3A is a line graph showing cumulative release of protein from Traps loaded with pancreatic beta cell lysate antigen.
Figure 3B:
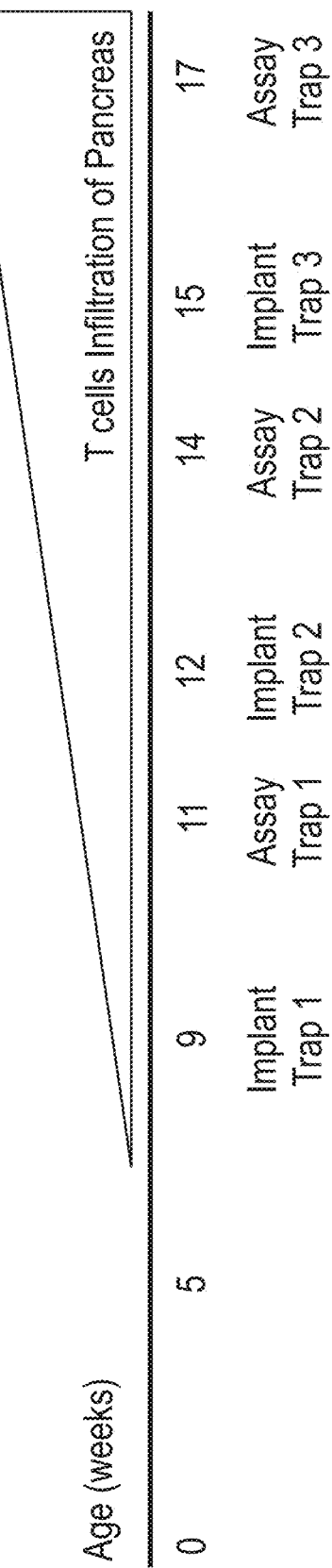
FIG. 3B is a schematic indicating the degree of T cell Infiltration in islets of NOD mice during implantation of T cell Traps. Traps were implanted when NOD mice were 9, 12, and 15 weeks old and assayed 2 weeks later.
Figure 3C:
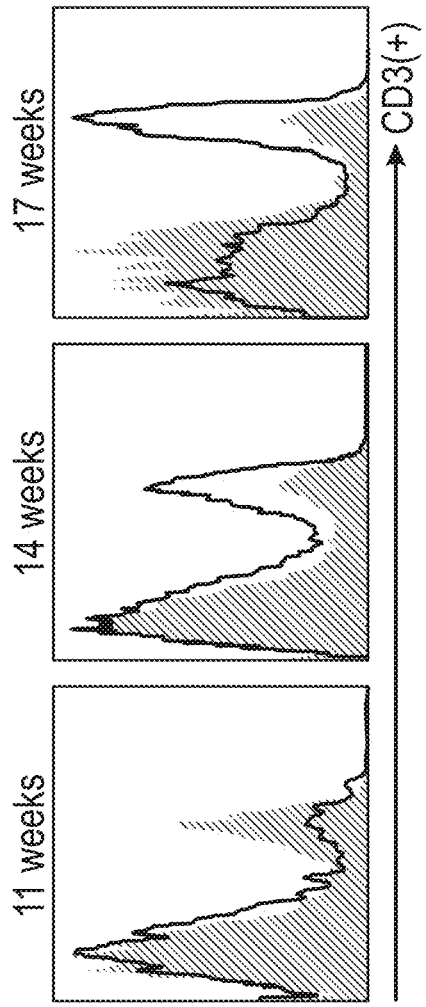
FIG. 3C is a series of FACS histograms displaying the levels of CD3(+) T cells harvested from controls (solid blue) and (3-cell traps (open red line) isolated from 11, 14 and 17 week old NOD mice.
Figure 3E:
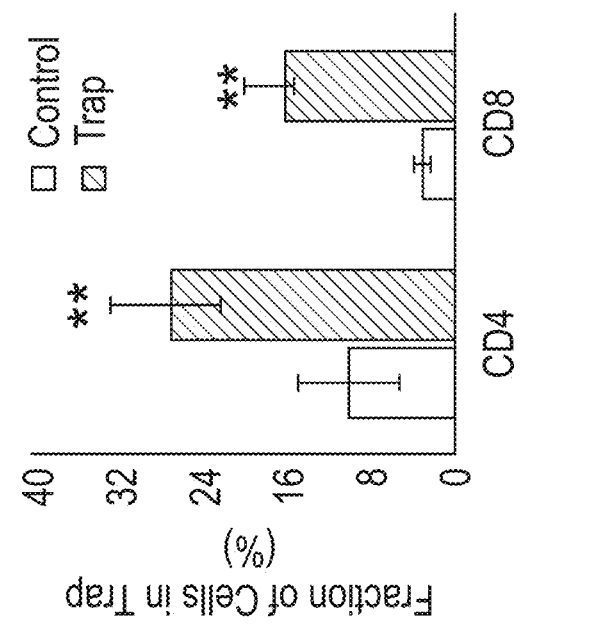
FIG. 3E is a bar graph showing the percentage of total cells isolated from traps and controls that are CD3(+)CD4(+) and CD3(+)CD8(+) T cells. The values in A, D and E represent the average and standard deviation (n=5). **P<0:01. These figures demonstrate T cell trapping during diabetes progression in non-obese diabetic mice.
Figure 3D:
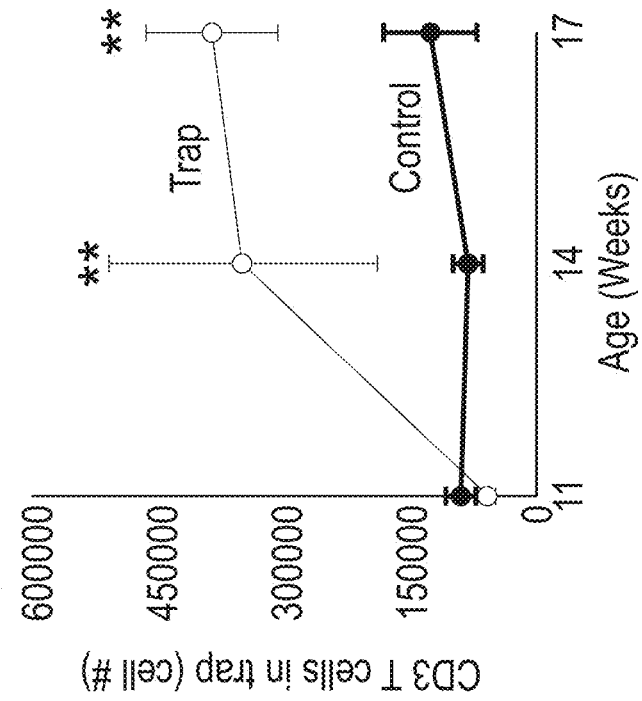
FIG. 3D is a line graph showing the total number of CD3(+) cells isolated from controls (Controls) and -cell loaded traps (Trap) explanted from NOD mice at 11, 14 and 17 weeks of age.

Antigen-specific trapping was demonstrated in an art-recognized mouse model for type 1 diabetes. Diabetic T cell traps were fabricated by loading PLG scaffolds with beta-cell lysate (FIG. 3A). These traps were then implanted into non-obese diabetic (NOD) mice at ages 9, 12, and 15 weeks for 2 weeks when they were assayed for T cell infiltration (FIG. 3B). In NOD mice, insulitis or T cell infiltration of islets increases predictably with age as illustrated in FIG. 3B. In particular, traps were found to significantly accumulate T cells relative to controls, and the infiltration correlated with insulitis in the pancreas (FIG. 3B and FIG. 3D). The total number of T cells in traps not only increased with diabetes progression, but the T cell populations were also enriched. There was a three to five fold difference in the number of T-cells in traps compared to controls.

Example 4: Characterization of Trapped T-Cells

Figure 4B:
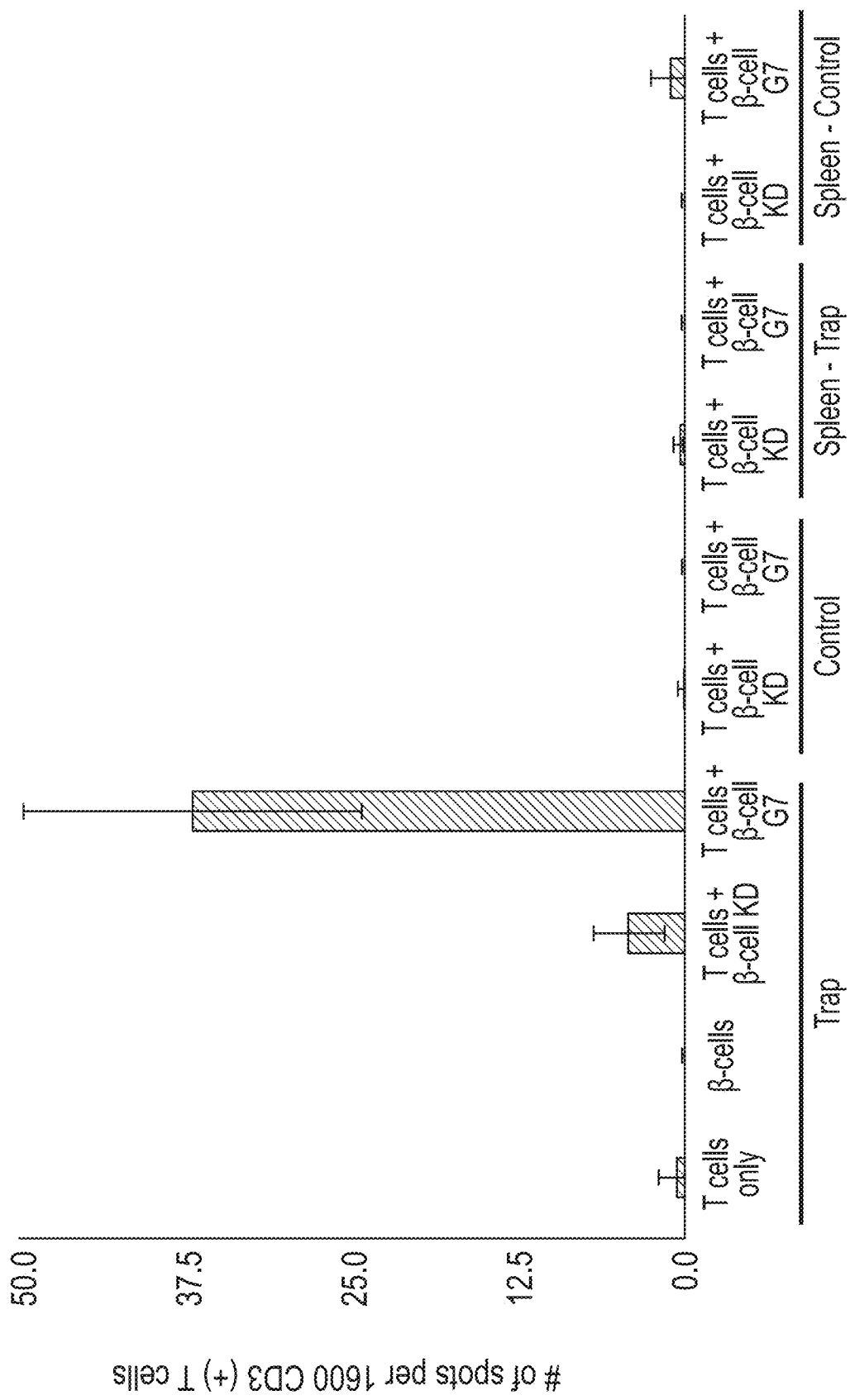
FIG. 4B is a line graph showing a comparison of the number of IL-2 positive spots (normalized to 1600 T cells) generated by T cells extracted from traps versus spleens. Spots were developed and quantified in wells containing beta cells cultured with T cells from antigen loaded traps (Trap), control scaffolds (Control), spleens of mice implanted with Traps (Spleen-Trap), or spleens of mice implanted with control scaffolds (Spleen-Control). Beta cell targets were modified to overexpress either MHC class I H2(Kd) ((3-cell I(D) or MHC class II I-A(g7) ((3-cell G7). T cells (T cells only) and Beta cells ((3-cells) were assayed alone as controls. Values in B represent the mean and standard deviation. These figures demonstrate that the traps are effective for enrichment of Beta Cell specific T cells.
Figure 6B:
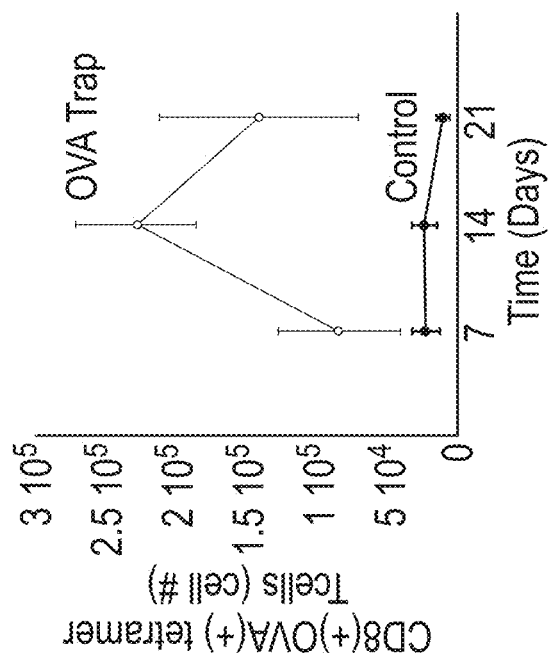
FIG. 6A-D show recruitment of cancer-specific T-cells in vivo.
Figure 6A:
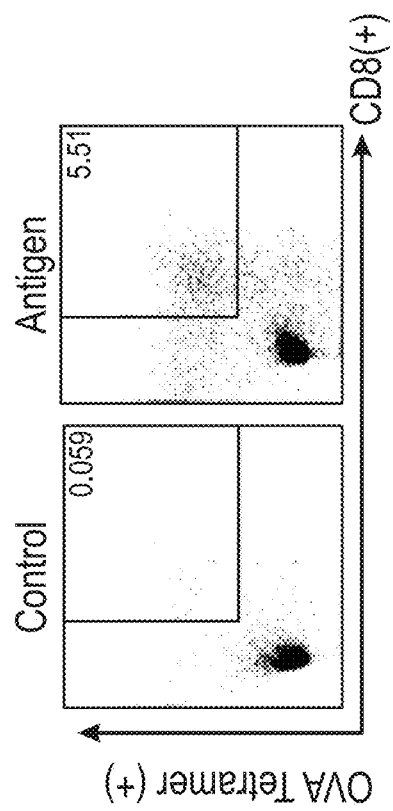
Figure 6D:
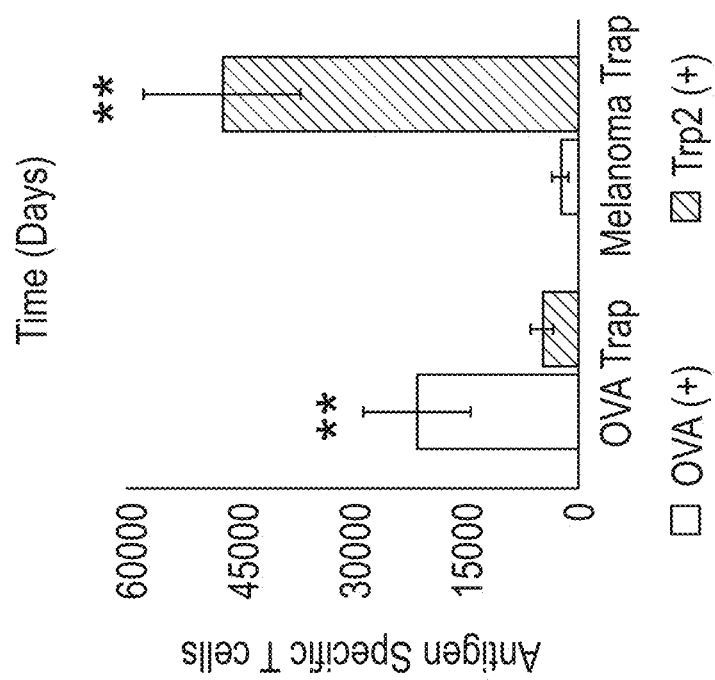
Figure 6C:
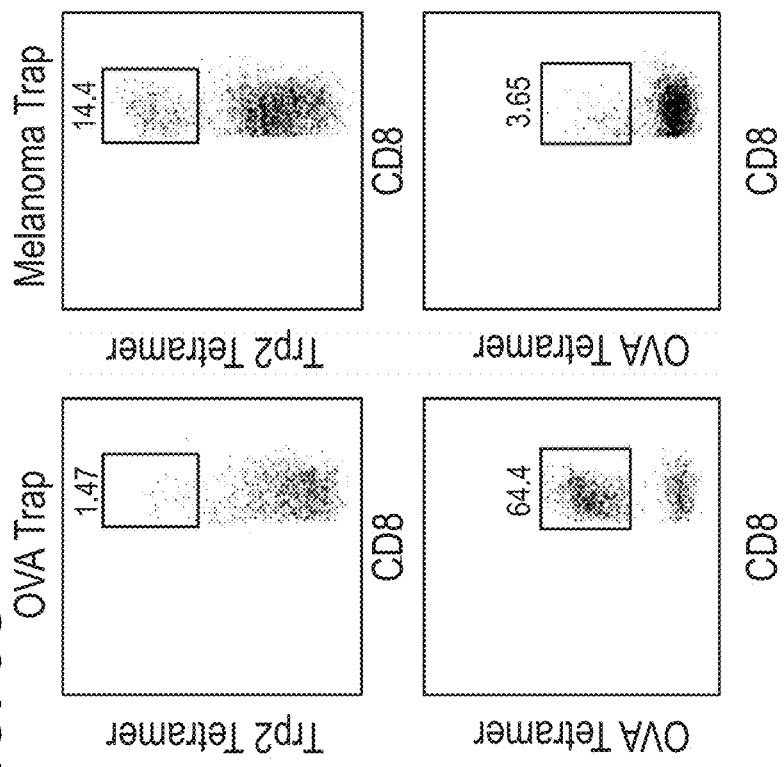
Figure 7:
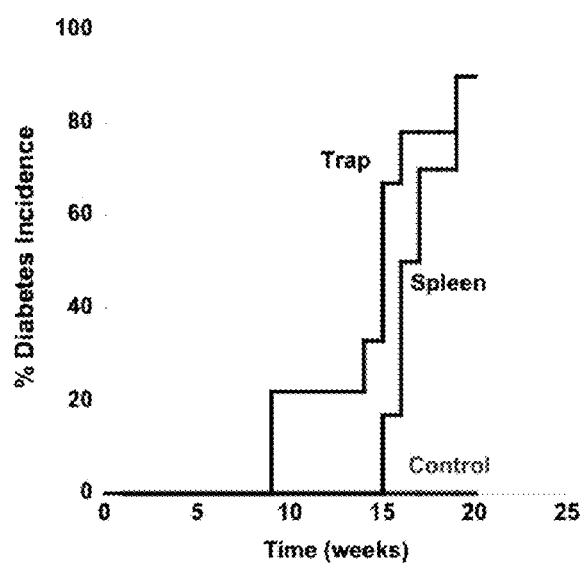
FIG. 7 shows the kinetics of diabetes incidence after transfer of cells from traps. Fifteen week old NOD mice were implanted with either blank PLG scaffolds (Control) or scaffolds containing beta-cell lysate (Traps). At 17 weeks $2 \times 10^6$ cells extracted from control and trap scaffolds along with splenocytes from untreated NOD mice (spleen) were intravenously injected into NOD-SCID mice. The plasma glucose levels in mice were monitored weekly and mice were considered diabetic after registering glucose levels higher than 250 mg/dL for two consecutive weeks (n=8 or 9).

T cells were harvested 14 days after implantation in NOD mice at ages 11, 14 and 17 weeks. Pancreatic beta cell targets were cultured with the harvested T cells. IL-2 secretion was measured using an ELISPOT assay. Results are shown in FIG. 4A. It was found that a significant subset of T cells isolated from traps (12% of T cells) was responsive to beta-cell targets in vitro as demonstrated by ELISPOT (FIG. 4A). In contrast, control traps were completely devoid of T cells responsive to pancreatic beta cells. The traps contained enriched levels of beta-cell specific T cells relative to control traps and spleens of mice, indicating that higher T cell numbers and enriched specificity could be obtained from traps relative to T cell levels in the blood. T cells in traps were analyzed and compared to T cells in spleens as a marker of blood levels. Diabetes-specific cells were identified in the traps were enriched by approximately 4000% relative to blood concentration (FIG. 4B).

Example 5: Trapping and Harvesting Cancer Specific T Cells

Porous scaffolds were loaded with antigens and other molecular patterns of the disease. One set of traps contained a unique mixture of OVA antigens, the other set contained a unique mixture of melanoma antigens. It was found that T cells that are specific to an antigen accumulated preferentially in traps loaded with the cognate antigen (FIG. 5C). More specifically, OVA specific T cells accumulated significantly in OVA traps whereas Trp2 (melanoma antigen) specific T cells accumulated significantly in melanoma traps (FIG. 5D). Conversely, the OVA and melanoma specific cells were absent from the traps which did not contain the corresponding antigen (FIG. 5C and FIG. 5D). These results show that antigen-specific T cells can be trapped and harvested based on the antigens that are provided in the scaffold.

Example 6: Transferring Functional T-Cells to Host

T cell traps and blank scaffolds were implanted subcutaneously into 15 week-old NOD mice for 14 days. Cells were then isolated from these scaffolds and $2 \times 10^6$ cells were transferred to NOD SCID mice via retro-orbital injection. Splenocytes from 17 week-old NOD mice were also injected into NOD-SCID recipients as a positive control. After cell transfer, the mice were monitored for the onset of diabetes by measuring blood glucose.

NOD-SCID mice receiving NOD derived splenocytes began to develop diabetes at 15 weeks after cell injection and 88% became diabetic by week 20 (FIG. 6). Trapped cells induced diabetes with faster kinetics as 20% of mice became diabetic by week 9 and 100% of mice were diabetic at 20 weeks. Cells extracted from control scaffolds completely failed to induce diabetes in SCID mice. These data indicate that Traps are able to specifically recruit functional, T-cells that can be transferred into the host.

Taken together, Examples 5 and 6 demonstrate that T cells can be generated and/or harvested in situ using porous scaffolds of the invention that are loaded with antigen(s) and molecular patterns of the disease. The results show that antigen-specific T cells are attracted and generated at these traps in vivo that can be harvested, similar to how they home and expand at primary sites of disease. These cells are generated in vivo and may also be expanded further via delivery of growth factors/cytokines from the trap. Surprisingly and unexpectedly, it was found that the functionality of trapped, disease-specific T cells is maintained after adoptive transfer into a host.

Example 7: Trapping of Cells for Clinical or Analytical Use

T cell traps, B cell traps, and/or dendritic cell traps are constructed using the aforementioned manufacturing processes. For example, T cell traps can utilize different chemokines/cytokines as shown in Table 1. Likewise, exemplary traps for dendritic cells/macrophages may utilize the cytokines/chemokines shown in Table 2. Similarly, B-cell traps may include the various cytokines/chemokines shown in Table 3. For each type of trap, additional agents, such as, for example, interleukins, growth factors, sequestering agents, adhesion receptors, or other compounds/molecules may be optionally employed. Table 4 provides a list of interleukins that may be optionally employed in the T-cell, B-cell, or DC/macrophage traps. Table 5 provides a list of T-cell adhesion receptors.

Loading with antigens is an effective homing agent to differentiate T cells from DCs. These immune cells are then analyzed to understand disease pathogenesis and to identify therapeutic targets such as antigens. Disease-causing T cells are currently inaccessible as they concentrate only in the lesions of autoimmunity. The trap technology described herein provide a means to collect these cells.

The devices are implanted in subjects for at least a day and up to 14 days or more as described above. Cells may proliferate within the device, and the device loaded with immune cells can be explanted anywhere from days 1-28, or longer, e.g., 30 days, 60 days, 3 months, 6 months, 9 months, 12 months, 18 months, 24 months, 36 months, 48 months or more. The devices may be monitored periodically.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A T cell trapping device, comprising
   a physiologically-compatible porous polymer scaffold, and
   a plurality of antigens,
   wherein the plurality of antigens attract and trap a plurality of T cells specific to the plurality of antigens in the device;
   and
   wherein the plurality of antigens engage a specific T-cell receptor on the plurality of T-cells causing the plurality of T-cells to remain in the device.

2. The device of claim 1, wherein the antigens are adsorbed onto the polymer scaffold or are encapsulated by the polymer scaffold.

3. The device of claim 1, wherein the device further comprises a T cell recruitment agent.

4. The device of claim 3, wherein the T cell recruitment agent
   comprises an agent selected from the group consisting of a CD3+ T-cell recruiting agent, a CD4+ T-cell recruiting agent, a CD8+ T cell recruiting agent, a CD8+ T cell recruiting agent, a regulatory T-cell (Treg) recruiting agent, a growth factor, a cytokine, an interleukin, an adhesion signaling molecule, an integrin signaling molecule, an interferon, a lymphokine, or a chemokine, or a fragment thereof, or a combination thereof.

5. The device of claim 1, wherein the device further comprises an agent which enhances infiltration of the immune cells into the device.

6. The device of claim 1, wherein the plurality of antigens are cancer antigens, non-self antigens, or self antigens.

7. The device of claim 6, wherein the cancer antigens are selected from the group consisting of MAGE-1, MAGE-2, MAGE-3, CEA, Tyrosinase, midkin, BAGE, CASP-8, β-catenin, β-catenin, γ-catenin, CA-125, CDK-1, CDK4, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf 112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Glil, Cav-1, cathepsin B, CD74, E-cadherin, EphA2/Eck, Fra-1/Fosl 1, GAGE-1, Ganglioside/GD2, GnT-V, γ1,6-N, Ki67, Ku70/80, PROX1, PSCA, SOX10, SOX11, Survivin, UPAR, WT-1, Dipeptidyl peptidase IV (DPPIV), adenosine deaminase-binding protein (AD Abp), cyclophilin b, Colorectal associated antigen (CRC)- C017-1A/GA733, T-cell receptor/CD3-zeta chain, GAGE-family of tumor antigens, RAGE, LAGE-I, NAG, GnT-V, RCAS1, α-fetoprotein, p120ctn, Pmel117, PRAME, brain glycogen phosphorylase, SSX—I, SSX-2 (HOM-MEL-40), SSX—I, SSX-4, SSX-5, SCP-I, CT-7, cdc27, *adenomatous polyposis coli* protein (APC), fodrin, P1A, Connexin 37, Ig-idiotype, p15, GM2, GD2 gangliosides, Smad family of tumor antigens, lmp-1, EBV-encoded nuclear antigen (EBNA)-I, UL16-binding protein-like transcript 1 (Multi), RAE-1 proteins, H60, MICA, MICB, and c-erbB-2, or an immunogenic peptide thereof, and combinations thereof.

8. The device of claim 6, wherein the non-self antigens are pathogenic antigens derived from a pathogen selected from the group consisting of a virus, a bacteria, a protozoan, a parasite, and a fungus.

9. The device of claim 6, wherein the plurality of antigens are derived from a lysate of a cell to which an autoimmune response is directed.

10. The device of claim 6, wherein the plurality of antigens are selected from the group consisting of a pancreatic beta cell antigen, a neuronal cell antigen, a bone or joint associated autoimmune disease associated antigen, or a gastrointestinal-disease associated antigen.

11. The device of claim 1, wherein the device further comprises an RGD peptide, a CpG oligonucleotide or a granulocyte-macrophage colony-stimulating factor (GM-CSF) cytokine, or a fragment thereof or a combination thereof.

12. The device of claim 2, wherein the T cell recruitment agent comprises a chemokine selected from the group consisting of CCL1, CCL2 (MCP-1), CCL-3, CCL-4, CCL-5 (RANTES), CCL-17, CCL-22, CXCL12 and XCL1, or a fragment thereof, or a combination thereof.

13. The device of claim 3, wherein the T cell recruitment agent comprises a chemokine selected from the group consisting of CCL2, CCL3, CCL5, CCL7, CCL8, CCL13, CCL17, and CCL22 or a fragment thereof, or a combination thereof.

14. The device of claim 3, wherein the T cell recruitment agent comprises a chemokine selected from the group consisting of CCL17 and CCL22, or a fragment thereof, or a combination thereof.

15. The device of claim 1, further comprising a plurality of adhesion receptors for T-cells selected from the group consisting of LFA-1, MAdCAM-1, VCAM-1, CD28 and CTLA-4 or a fragment thereof or a combination thereof.

16. The device of claim 1, wherein the device comprises about 10 µg to about 2.0 mg of the antigens; or about 0.1 µg to about 400 µg of the antigens per gram of dry weight of the scaffold.

17. The device of claim 1, wherein the device has a porosity of between about 40% to about 90%.

18. The device of claim 1, wherein the porous polymer scaffold comprises pores having a diameter of about 10 µm to about 500 µm.

19. The device of claim 1, wherein the porous polymer scaffold comprises a compound selected from the group consisting of polylactic acid (PLA), polyglycolic acid (PGA), poly(lactide-co-glycolide) (PLGA), alginate or a derivative thereof, gelatin, collagen, fibrin, hyaluronic acid (HA), agarose, a polysaccharide, a polyamino acid, a polypeptide, a polyester, a polyanhydride, a polyphosphazine, a polyvinyl alcohol (PVA), a polyalkylene oxide (PAO), a polyallyl amine (PAM), a polyacrylate, a modified styrene polymer, a pluronic polyol, a polyoxamer, a polyuronic acid, and a polyvinylpyrrolidone, a co-polymer thereof, and or a graft polymer thereof.

20. A pharmaceutical composition comprising the device of claim 1 and a pharmaceutically acceptable carrier.

21. A method of treating a disease in a subject in need thereof, comprising
  administering the device of claim 1 to a subject, wherein the plurality of antigens are specific for the disease;
  collecting a plurality of T cells trapped in the device, wherein the plurality of T cells are specific to the plurality of antigens; and
  administering the plurality of T cells into the subject, thereby treating the disease in the subject.

22. A method for obtaining T cells specific for an antigen, comprising
  administering the device of claim 1 to a subject; and
  harvesting T cells trapped in the device, thereby obtaining T cells specific for the antigen.

23. A method for determining whether a subject has an autoimmune disease, comprising
  administering the device of claim 1 into a subject, wherein the plurality of antigens are specific for the autoimmune disease;
  collecting T cells trapped in the device, wherein the T cells are specific to the autoimmune disease; and
  determining the number of T cells specific to the autoimmune disease trapped in the device, thereby determining whether a subject has an autoimmune disease.

24. A method for making the device of claim 1, comprising
  incubating a plurality of purified antigens with a physiologically compatible polymer to generate a polymer-antigen mixture;
  freezing, lyophilizing and mixing the polymer-antigen mixture with a porogen;
  compression molding the mixture to produce a disc;
  subjecting the disk to a high-pressure $CO_2$ environment and rapidly reducing the pressure to expand and fuse the polymer into an interconnected scaffold structure; and
  leaching the porogen from the scaffold structure by immersing the structure in water to generate a porous article, thereby making the device.

25. The device of claim 1, wherein the plurality of antigens are a plurality of melanoma antigens Trp2.

26. The device of claim 1, wherein the plurality of antigens are a cell lysate of a plurality of beta cells associated with type I diabetes.

27. The device of claim 1, wherein the plurality of antigens are a plurality of pancreatic beta cell antigens associated with type I diabetes.

* * * * *